(12) United States Patent
Judd et al.

(10) Patent No.: US 8,901,152 B2
(45) Date of Patent: Dec. 2, 2014

(54) INHIBITORS OF DIACYLGLYCEROL O-ACYLTRANSFERASE TYPE 1 ENZYME

(75) Inventors: Andrew S. Judd, Grayslake, IL (US); Mathew M. Mulhern, Lake Villa, IL (US); Rajesh R. Iyengar, Newton, MA (US); Philip R. Kym, Libertyville, IL (US); Andrew J. Souers, Evanston, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 13/549,651

(22) Filed: Jul. 16, 2012

(65) Prior Publication Data

US 2012/0277223 A1    Nov. 1, 2012

Related U.S. Application Data

(62) Division of application No. 12/112,635, filed on Apr. 30, 2008, now Pat. No. 8,242,139.

(60) Provisional application No. 60/914,963, filed on Apr. 30, 2007.

(51) Int. Cl.
| | |
|---|---|
| A61K 31/445 | (2006.01) |
| A61K 31/425 | (2006.01) |
| C07D 498/08 | (2006.01) |
| C07D 417/14 | (2006.01) |
| C07D 213/40 | (2006.01) |
| C07D 417/12 | (2006.01) |
| C07D 277/82 | (2006.01) |
| C07D 417/04 | (2006.01) |
| C07D 213/75 | (2006.01) |
| C07D 405/04 | (2006.01) |
| C07D 277/28 | (2006.01) |

(52) U.S. Cl.
CPC ............ *C07D 417/04* (2013.01); *C07D 498/08* (2013.01); *C07D 417/14* (2013.01); *C07D 213/40* (2013.01); *C07D 417/12* (2013.01); *C07D 277/82* (2013.01); *C07D 213/75* (2013.01); *C07D 405/04* (2013.01); *C07D 277/28* (2013.01)
USPC ............ 514/326; 514/365; 546/209; 548/205

(58) Field of Classification Search
None
See application file for complete search history.

(56) References Cited

U.S. PATENT DOCUMENTS

| | | |
|---|---|---|
| 5,859,041 A | 1/1999 | Liverton et al. |
| 2002/0049220 A1 | 4/2002 | Revesz et al. |
| 2004/0097552 A1 | 5/2004 | Duffy et al. |
| 2007/0129404 A1 | 6/2007 | Hagihara et al. |

FOREIGN PATENT DOCUMENTS

| | | |
|---|---|---|
| EP | 1679308 A1 | 7/2006 |
| EP | 1764360 | 3/2007 |
| JP | 2009539818 A | 11/2009 |
| WO | 0040576 A2 | 7/2000 |
| WO | 0063204 A2 | 10/2000 |
| WO | 2004089913 A1 | 10/2004 |
| WO | 2006026306 A1 | 3/2006 |
| WO | 2006137658 A1 | 12/2006 |
| WO | 2007126957 A2 | 11/2007 |
| WO | 2007144202 A1 | 12/2007 |

OTHER PUBLICATIONS

Guo T., et al., "Discovery and SAR of Biaryl Piperidine MCH1 Receptor Antagonists through Solid-phase Encoded Combinatorial Synthesis," Bioorganic and Medicinal Chemistry Letters, 2005, vol. 15 (16), pp. 3696-3700.
International Search Report for Application No. PCT/US2008/061951, mailed on Aug. 6, 2008, 4 pages.
Non-Final Office Action mailed Jul. 18, 2011, for U.S. Appl. No. 12/112,635 filed Apr. 30, 2008.
Notice of Allowance mailed Jan. 5, 2012, for U.S. Appl. No. 12/112,635, filed Apr. 30, 2008.
Notice of Allowance mailed Apr. 12, 2012, for U.S. Appl. No. 12/112,635, filed Apr. 30, 2008.
Notice of Allowance mailed Nov. 28, 2011, for U.S. Appl. No. 12/112,635, filed Apr. 30, 2008.
Office Action mailed Feb. 19, 2013 for European Application No. 08795827.8 filed Apr. 30, 2008.
Office Action mailed Jun. 11, 2013 for Japanese Application No. 2010506586 filed Apr. 30, 2008.
Pascal C., et al., "Synthesis of Biphenyls Mimicking the Structure of the Antimitotic Rhazinilam," The Journal of Organic Chemistry, 1998, vol. 63 (18), pp. 6414-6420.
Revesz L., et al., "Vicinal Bromostannanes as Novel Building Blocks for the Preparation of di- and Trisubstituted Imidazoles," Tetrahedron Letters, 1998, vol. 39, pp. 5171-5174.

*Primary Examiner* — Samantha Shterengarts
(74) *Attorney, Agent, or Firm* — Lisa V. Mueller; Michael Best & Friedrich LLP

(57) ABSTRACT

The present invention relates to compounds of formula (I):

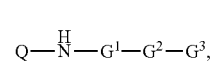

wherein Q, $G^1$, $G^2$, and $G^3$, are defined herein. Pharmaceutical compositions and methods for treating DGAT-1 related diseases or conditions are also disclosed.

15 Claims, No Drawings

INHIBITORS OF DIACYLGLYCEROL O-ACYLTRANSFERASE TYPE 1 ENZYME

This is a divisional of U.S. Pat. application Ser. No. 12/112,635, filed on Apr. 30, 2008, which claims priority to U.S. Provisional Patent Application No. 60/914,963, filed Apr. 30, 2007, the contents of all of which are herein fully incorporated by reference.

FIELD OF THE INVENTION

Compounds that are inhibitors of the diacylglycerol O-acyltransferase type 1 (DGAT-1) enzyme are disclosed. Methods of using such compounds to inhibit the activity of diacylglycerol O-acyltransferase type 1 and pharmaceutical compositions including such compounds are also encompassed.

BACKGROUND OF THE INVENTION

Triacylglycerides represent the major form of energy storage in eukaryotes, and disorders or imbalance in triacylglycerides metabolism are implicated in the pathogenesis and increased risk for obesity, insulin resistance, type II diabetes, nonalcoholic fatty liver disease and coronary heart disease (Lewis, et al., Endocrine Reviews 23:201, 2002). Storage of excess triacylglycerides in lean tissues, such as liver, muscle, and other peripheral tissues, leads to lipid-induced dysfunction in those tissues; thus, reducing fat accumulation in nonadipose sites appears to be of benefit in the treatment of lipotoxicity (Unger, R. H. Endocrinology, 144: 5159-5165, 2003). Accumulation of excess triacylglycerides in white adipose tissue (WAT) leads to obesity, a condition that is associated with decreased life span, type II diabetes, coronary artery disease, hypertension, stroke, and the development of some cancers (Grundy, S. M. Endocrine 13(2): 155-165, 2000). Obesity is a chronic disease that is highly prevalent in modern society and current pharmacological treatment options are limited, creating a heed to develop pharmaceutical agents for the treatment of obesity that are safe and effective.

Diacylglycerol O-acyltransfereases (DGATs) are membrane-bound enzymes that catalyze the terminal step of triacylglycerides biosynthesis. Two enzymes that display DGAT activity have been characterized: DGAT-1 (diacylglycerol O-acyltransferase type 1) (U.S. Pat. No. 6,100,077; Cases, et al., Proc. Nat. Acad. Sci. 95:13018-13023, 1998) and DGAT-2 (diacylglyerol O-acyltransferase type 2) (Cases, et al., J. Biol. Chem. 276:38870-38876, 2001). DGAT-1 and DGAT-2 share only 12% sequence identity. Significantly, DGAT-1 null mice are resistant to diet-induced obesity and have increased sensitivity to insulin and leptin (Smith, et al., Nature Genetics 25:87-90, 2000; Chen and Farese, Trends Cardiovasc Med. 10:188, 2000; Chen et al., J. Clin. Invest. 109:10049, 2002). DGAT-1 deficient mice are protected against hepatic steatosis, demonstrate increased energy expenditure, and decreased levels of tissue triacylglycerides. In addition to improved triacylglycerides metabolism, DGAT-1 deficient mice also have improved glucose metabolism, with lower glucose and insulin levels following a glucose load, in comparison to wild-type mice. Partial DGAT-1 deficiency in heterozygous DGAT-1+/− animals is sufficient to deliver an intermediate phenotype on body weight, adiposity, and insulin and glucose metabolism when compared to wild type and homozygous littermates (Chen and Farese, Arterioscler. Thromb. Vase. Biol. 25:482-486, 2005), and small molecule DGAT-1 inhibitors have been reported to induce weight loss in diet-induced obese (DIO) mice (US 2004/0224997). The phenotypes of DGAT-1 deficient mice, and the pharmacological activity reported with DGAT-1 inhibitors suggests that the discovery of small molecules that effectively block the conversion of diacylglycerol to triacylglycerides by inhibiting the DGAT-1 enzyme can have utility in the treatment of obesity and other diseases associated with triacylglycerides imbalance.

SUMMARY OF THE INVENTION

One aspect of the invention is directed towards compounds of formula (I), or a pharmaceutically acceptable salt, prodrug, salt of a prodrug, or a combination thereof,

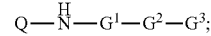

(I)

wherein $G^1$ is phenyl or monocyclic heteroaryl, each of which is optionally further substituted with 1, 2, 3, or 4 substituents as represented by T;

$G^2$ is phenyl or monocyclic heteroaryl, each of which is optionally further substituted with 1, 2, 3, or 4 substituents as represented by T;

T, at each occurrence, is independently selected from the group including, but not limited to, alkyl, alkenyl, alkynyl, halogen, —CN, —NO$_2$, —OR$^1$, —OC(O)(R$^2$), —N(R$^w$)(R$^1$), —N(R$^w$)C(O)(R$^1$), —N(R$^w$)—C(O)O(R$^1$), —N(R$^w$)—C(O)N(R$^w$)(R$^1$), —N(R$^w$)—S(O)$_2$(R$^2$), —C(O)O(R$^1$), —C(O)N(R$^w$)(R$^1$), —C(O)R$^1$, —SR$^1$, —S(O)R$^2$, —S(O)$_2$R$^2$, —S(O)$_2$N(R$^w$)(R$^1$), —(CR$^a$R$^b$)$_r$—CN, —(CR$^a$R$^b$)$_r$—NO$_2$, —(CR$^a$R$^b$)$_r$—OR$^1$, —(CR$^a$R$^b$)$_r$—OC(O)(R$^2$), —(CR$^a$R$^b$)$_r$—N(R$^w$)(R$^1$), —(CR$^a$R$^b$)$_r$—N(R$^w$)C(O)(R$^1$), —(CR$^a$R$^b$)$_r$N(R$^w$)—C(O)O(R$^1$), —(CR$^a$R$^b$)$_r$—N(R$^w$)—C(O)N(R$^w$)(R$^1$), —(CR$^a$R$^b$)$_r$—N(R$^w$)—S(O)$_2$(R$^2$), —(CR$^a$R$^b$)$_r$—C(O)O(R$^1$), —(CR$^a$R$^b$)$_r$—C(O)N(R$^w$)(R$^1$), —(CR$^a$R$^b$)$_r$—C(O)R$^1$, —(CR$^a$R$^b$)$_r$—SR$^1$, —(CR$^a$R$^b$)$_r$S(O)R$^2$, —(CR$^a$R$^b$)$_r$—S(O)$_2$R$^2$, —(CR$^a$R$^b$)$_r$—S(O)$_2$N(R$^w$)(R$^1$), and haloalkyl; or two of the adjacent substituents T, together with the carbon atoms to which they are attached, form a monocyclic ring selected from the group including, but not limited to, phenyl, heterocycle and heteroaryl, wherein each ring is optionally further substituted with 1, 2 or 3 substituents selected from the group including, but not limited to, oxo, alkyl, alkenyl, alkynyl, halogen, —CN, —NO$_2$, —OR$^1$, —OC(O)(R$^2$), —N(R$^w$)(R$^1$), —N(R$^w$)C(O)(R$^1$), —N(R$^w$)—C(O)O(R$^1$), —N(R$^w$)—C(O)N(R$^w$)(R$^1$), —N(R$^w$)—S(O)$_2$(R$^2$), —C(O)O(R$^1$), —C(O)N(R$^w$)(R$^1$), —C(O)R$^1$, —SR$^1$, —S(O)R$^2$, —S(O)$_2$R$^2$, —S(O)$_2$N(R$^w$)(R$^1$), —(CR$^a$R$^b$)$_r$—CN, —(CR$^a$R$^b$)$_r$—NO$_2$, —(CR$^g$R$^h$)$_r$OR$^1$, —(CR$^a$R$^b$)$_r$OC(O)(R$^2$), —(CR$^a$R$^b$)$_r$—N(R$^w$)(R$^1$), —(CR$^a$R$^b$)$_r$—N(R$^w$)C(O)(R$^1$), —(CR$^a$R$^b$)$_r$—N(R$^w$)—C(O)O(R$^1$), —(CR$^a$R$^b$)$_r$—N(R$^w$)—C(O)N(R$^w$)(R$^1$), —(CR$^a$R$^b$)$_r$—N(R$^w$)—S(O)$_2$(R$^2$), —(CR$^a$R$^b$)$_r$—C(O)O(R$^1$), —(CR$^a$R$^b$)$_r$—C(O)N(R$^w$)(R$^1$), —(CR$^a$R$^b$)$_r$—C(O)R$^1$, —(CR$^a$R$^b$)$_r$SR$^1$, —(CR$^a$R$^b$)$_r$—S(O)R$^2$, —(CR$^a$R$^b$)$_r$—S(O)$_2$R$^2$, —(CR$^a$R$^b$)$_r$—S(O)$_2$N(R$^w$)(R$^1$), and haloalkyl;

$G^3$ is formula (a) or formula (b)

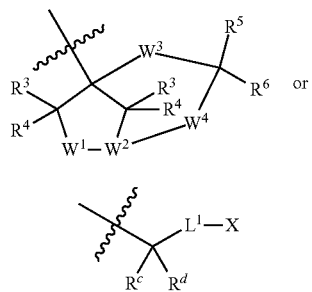

$W^1$ is —C($R^3$)($R^4$)— or —C($R^3$)($R^4$)—C($R^3$)($R^4$)—, and $W^2$ is —C($R^7$)— or N; or $W^1$ is N(H), N(alkyl), O, S(O), or S(O)$_2$, and $W^2$ is —C($R^7$)—;

$W^3$ is N(H), N(alkyl), or O;

$W^4$ is —C($R^3$)($R^4$)— or —C($R^3$)($R^4$)—C($R^3$)($R^4$)—;

$R^3$ and $R^4$, at each occurrence, are independently hydrogen or $C_{1-6}$ alkyl;

$R^5$ and $R^6$ are independently hydrogen or $C_{1-6}$ alkyl; or $R^5$ and $R^6$, together with the carbon to which they are attached, is C(=O);

$R^7$, at each occurrence, is independently hydrogen, $C_{1-6}$ alkyl or —C(O)OH;

$R^c$ and $R^d$, together with the carbon atom to which they are attached, is a 3- to 6-membered cycloalkyl or a monocyclic heterocycle of formula (c);

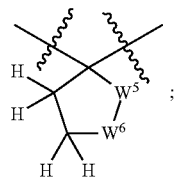

wherein 1, 2, 3, or 4 hydrogen atoms attached to the ring carbon of the cycloalkyl and the monocyclic heterocycle are optionally replaced with radicals selected from the group including, but not limited to, alkyl, halogen, —CN, haloalkyl, —C(O)C($R^8$), —C(O)N($R^8$)($R^9$), —(CR$^e$R$^f$)$_t$—C(O)O($R^8$), and —(CR$^e$R$^f$)$_t$—C(O)N($R^8$)($R^9$);

$W^5$ is —CH$_2$— or —CH$_2$—CH$_2$—;

$W^6$ is O, S, S(O), S(O)$_2$, N($R^x$), —C(O)N($R^y$)— or —N($R^y$)C(O)—; wherein $R^x$ is hydrogen, alkyl, haloalkyl, cycloalkyl, cycloalkenyl, aryl, heteroaryl, heterocycle, cycloalkylalkyl, cycloalkenylalkyl, arylalkyl, heteroarylalkyl, heterocyclealkyl, —C(O)O($R^z$), —C(O)$R^z$, or —C(O)N($R^w$)($R^m$);

$R^y$ and $R^m$, at each occurrence, are each independently hydrogen, alkyl, haloalkyl, aryl, cycloalkyl, cycloalkenyl, heteroaryl, heterocycle, arylalkyl, cycloalkylalkyl, cycloalkenylalkyl, heteroarylalkyl, or heterocyclealkyl;

$R^z$, at each occurrence, is independently alkyl, haloalkyl, aryl, cycloalkyl, cycloalkenyl, heteroaryl, heterocycle, arylalkyl, cycloalkylalkyl, cycloalkenylalkyl, heteroarylalkyl, or heterocyclealkyl;

$R^8$ and $R^9$, at each occurrence, are independently hydrogen, alkyl, aryl, cycloalkyl, cycloalkenyl, heteroaryl, heterocycle, haloalkyl, arylalkyl, cycloalkylalkyl, cycloalkenylalkyl, heteroarylalkyl, or heterocyclealkyl; or $R^8$ and $R^9$, together with the nitrogen atom to which they are attached, form a heterocycle ring, optionally further substituted with 1, 2 or 3 substituents selected from the group consisting of alkyl, halogen, and haloalkyl;

$L^1$ is O, N(H), or N(alkyl); and X is —(CR$^g$R$^h$)$_u$-tertrazolyl, heterocyclealkyl, heteroarylalkyl, hydrogen, alkyl, haloalkyl, —C(O)O($R^{10}$), —C(O)N($R^{10}$)($R^{11}$), —(CR$^g$R$^h$)$_u$—OR$^{10}$, —(CR$^g$R$^h$)$_u$N($R^{10}$)($R^{11}$), —(CR$^g$R$^h$)$_u$—CN, —(CR$^g$R$^h$)$_u$—C(O)O($R^{10}$), or —(CR$^g$R$^h$)$_u$—C(O)N($R^{10}$)($R^{11}$); or $L^1$ is —(CR$^p$R$^q$)$_s$— and X is —C(O)OH or tetrazolyl;

$R^{10}$ and $R^{11}$, at each occurrence, are independently hydrogen, alkyl, cycloalkyl, cycloalkenyl, heteroaryl, aryl, heterocycle, cycloalkylalkyl, cycloalkenylalkyl, heteroarylalkyl, arylalkyl, heterocyclealkyl, or haloalkyl; or $R^{10}$ and $R^{11}$, together with the nitrogen atom to which they are attached, form a heterocycle ring which is optionally further substituted with 1, 2, or 3 substituents selected from the group consisting of alkyl, halogen and haloalkyl;

Q is alkyl, alkenyl, alkynyl, haloalkyl, $G^4$, —$Y^1$—$Y^3$, or —$Y^1$—(CR$^j$R$^k$)$_v$—$Y^2$—$Y^4$; or Q is formula (d)

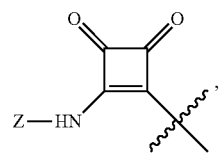

wherein

Z is alkyl, alkenyl, alkynyl, haloalkyl, $G^4$, —$Y^1$—$Y^3$, or —$Y^1$—(CR$^j$R$^k$)$_v$—$Y^2$—$Y^4$;

$G^4$ is cycloalkyl, cycloalkenyl, heterocycle, heteroaryl, aryl, cycloalkylalkyl, cycloalkenylalkyl, heterocyclealkyl, heteroarylalkyl, or arylalkyl;

$Y^1$, at each occurrence, is independently —C(O)—, —C(O)O—, —C(O)N($R^w$)—, —S(O)$_2$—, —S(O)$_2$—N($R^w$)—, wherein the right side of the —C(O)O—, —C(O)N($R^w$)—, and —S(O)$_2$—N($R^w$)— moieties are attached to $Y^3$ or (CR$^j$R$^k$)$_v$;

$Y^2$ at each occurrence is independently O, N($R^w$), or C(O);

$Y^3$ at each occurrence is independently alkyl, haloalkyl, cycloalkyl, cycloalkenyl, heterocycle, heteroaryl, aryl, cycloalkylalkyl, cycloalkenylalkyl, heterocyclealkyl, heteroarylalkyl or arylalkyl;

$Y^4$ at each occurrence is independently hydrogen, alkyl, haloalkyl, cycloalkyl, cycloalkenyl, heterocycle, heteroaryl, aryl, cycloalkylalkyl, cycloalkenylalkyl, heterocyclealkyl, heteroarylalkyl, or arylalkyl;

wherein the cycloalkenyl, cycloalkyl, heterocycle, heteroaryl, aryl, the aryl moiety of the arylalkyl, the heteroaryl moiety of the heteroarylalkyl, the cycloalkyl moiety of the cycloalkylalkyl, the heterocycle moiety of the heterocyclealkylalkyl, and the cycloalkenyl moiety of the cycloalkenylalkyl as represented by X, $G^4$, $Y^3$, $Y^4$, $R^x$, $R^y$, $R^z$, $R^m$, $R^8$, $R^9$, $R^{10}$, and $R^{11}$, are each optionally further substituted with 1, 2, 3, 4 or 5 substituents selected from the group consisting of alkyl, alkenyl, alkynyl, halogen, oxo, ethylenedioxy, methylenedioxy, —CN, —NO$_2$, —OR$^1$, —OC(O)($R^2$), —N($R^w$)($R^1$), —N($R^w$)C(O)($R^1$), —N($R^w$)—C(O)O($R^1$), —N($R^w$)—C(O)N($R^w$)($R^1$), —N($R^w$)—S(O)$_2$($R^2$), —C(O)O($R^1$), —C(O)N($R^w$)($R^1$), —N($R^w$)—S(O)$_2$($R^2$), —C(O)O($R^1$), —C(O)N($R^w$)($R^1$), —C(O)($R^1$), —SR$^1$, —S(O)$R^2$, —S(O)$_2$$R^2$, —S(O)$_2$N($R^w$)($R^1$), haloalkyl, —(CR$^a$R$^b$)$_r$—CN, —(CR$^a$R$^b$)$_r$—NO$_2$, —(CR$^a$R$^b$)$_r$—OR$^1$, —(CR$^a$R$^b$)$_r$—OC(O)(R$^2$), —(CR$^a$R$^b$)$_r$—N(R$^w$)(R$^1$), —(CR$^a$R$^b$)$_r$—N(R$^w$)C(O)(R$^1$), —(CR$^a$R$^b$)$_r$—N(R$^w$)—C(O)O(R$^1$), —(CR$^a$R$^b$)$_r$N(R$^w$)—C(O)N(R$^w$)(R$^1$), —(CR$^a$R$^b$)$_r$—N(R$^w$)—S(O)$_2$(R$^2$), —(CR$^a$R$^b$)$_r$C(O)O(R$^1$), —(CR$^a$R$^b$)$_r$—C(O)N(R$^w$)(R$^1$), —(CR$^a$R$^b$)$_r$—C(O)R$^1$, —(CR$^a$R$^b$)$_r$—SR$^1$, —(CR$^a$R$^b$)$_r$—S(O)R$^2$, —(CR$^a$R$^b$)$_r$—S(O)$_2$R$^2$, —(CR$^a$R$^b$)$_r$—S(O)$_2$N(R$^w$)(R$^1$), and haloalkyl;

R$^a$, R$^b$, R$^e$, R$^f$, R$^g$, R$^h$, R$^j$, R$^k$, R$^p$, and R$^q$, at each occurrence, are independently hydrogen, halogen, alkyl, or haloalkyl;

R$^1$ and R$^w$, at each occurrence, are independently hydrogen, alkyl, or haloalkyl;

R$^2$, at each occurrence, is independently alkyl or haloalkyl; and r, s, t, u, and v, at each occurrence, is independently 1, 2, 3, 4, 5 or 6.

Another aspect of the invention provides methods of treating various diseases or conditions in a subject, preferably a human, wherein the methods include administering to the subject in need thereof, a therapeutically or prophylactically effective amount of a compound of the invention as disclosed herein, or a pharmaceutically acceptable salt thereof, or a pharmaceutical composition including a compound of the invention or a pharmaceutically acceptable salt thereof, and a pharmaceutically acceptable carrier. In another aspect, the invention provides methods of preventing or treating a disease or condition related to elevated lipid levels, such as plasma lipid levels, especially elevated triacylglycerides levels, in a subject, especially human, afflicted with such elevated levels, including administering to the subject a therapeutically or prophylactically effective amount of a compound, a pharmaceutically acceptable salt thereof, or a pharmaceutical composition including the same, as disclosed herein. The invention also relates to compounds having therapeutic ability to reduce lipid levels in a subject (for example, mammal), especially triacylglycerides levels. Accordingly, the compounds and compositions of the invention, alone or together with one or more pharmaceutical agents selected from the group consisting of DPPIV inhibitor, incretin mimetic, metformin, fenofibrate, rimonabant, sibutramine, orlistat, nicotinic acid, and a statin, are useful for the preparation of a medicament for treating or preventing diseases and disorders described herein, particularly, for treating of preventing type 2 diabetes, obesity, elevated plasma triglycerides, metabolic syndrome, nonalcoholic steatohepatitis, and non-alcoholic fatty liver disease. Compounds of the invention or pharmaceutically acceptable salt thereof, or compositions thereof, alone or together with one or more pharmaceutical agents as described herein, are also useful for the presparation of a medicament for reducing lipid levels in a subject (e.g. mammal, including human), especially triglycerides levels. A further aspect of the invention provides pharmaceutical compositions including one or more compounds of the invention as disclosed herein or a pharmaceutically acceptable salt thereof, and a pharmaceutically acceptable carrier.

DETAILED DESCRIPTION OF THE INVENTION

For a variable that occurs more than one time in any substituent or in the compound of the invention or any other formulae herein, its definition on each occurrence is independent of its definition at every other occurrence. Combinations of substituents are permissible only if such combinations result in stable compounds. Stable compounds are compounds, which can be isolated in a useful degree of purity from a reaction mixture.

As used in the specification and the appended claims, unless specified to the contrary, the following terms have the meaning indicated:

The term "alkenyl" as used herein, means a straight or branched hydrocarbon chain containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkyl" as used herein, means a straight or branched, saturated hydrocarbon chain containing from 1 to 10 carbon atoms. The term "lower alkyl" or "$C_{1-6}$ alkyl" means a straight or branched chain hydrocarbon containing 1 to 6 carbon atoms. The term "$C_{1-3}$ alkyl" means a straight or branched chain hydrocarbon containing 1 to 3 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylene" denotes a divalent group derived from a straight or branched chain hydrocarbon of from 1 to 10 carbon atoms. Representative examples of alkylene include, but are not limited to, —CH$_2$—, —CH$_2$CH$_2$—, —CH$_2$CH$_2$CH$_2$—, —CH$_2$CH$_2$CH$_2$CH$_2$—, and —CH$_2$CH(CH$_3$)CH$_2$—.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "aryl" as used herein, means phenyl or a bicyclic aryl. The bicyclic aryl is naphthyl, or a phenyl fused to a monocyclic cycloalkyl, or a phenyl fused to a monocyclic cycloalkenyl. The phenyl and the bicyclic aryl groups of the present invention are unsubstituted or substituted. The bicyclic aryl is attached to the parent molecular moiety through any carbon atom contained within the bicyclic aryl. Representative examples of the aryl groups include, but are not limited to, bicyclo[4.2.0]octa-1,3,5-trien-7-yl, dihydroindenyl, indenyl, naphthyl, dihydronaphthalenyl, and 5,6,7,8-tetrahydronaphthalenyl.

The term "arylalkyl" as used herein, means an aryl group, as defined herein, appended to the parent molecular moiety through an alkyl group, as defined herein. Representative examples of arylalkyl include, but are not limited to, benzyl, 2-phenylethyl and 3-phenylpropyl.

The term "cycloalkyl" or "cycloalkane" as used herein, means a monocyclic, a bicyclic or a tricyclic cycloalkyl. The monocyclic cycloalkyl is a hydrocarbon ring system containing three to eight carbon atoms, zero heteroatoms and zero double bonds. Examples of monocyclic ring systems include cyclopropyl, cyclobutyl, cyclopentyl, cyclohexyl, cycloheptyl, and cyclooctyl. The bicyclic cycloalkyl is a monocyclic cycloalkyl fused to a monocyclic cycloalkyl ring, or a bridged monocyclic cycloalkyl in which two non-adjacent carbon atoms of the monocyclic ring are linked by an alkylene bridge containing one, two, three, or four carbon atoms. Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Tricyclic cycloalkyls are exemplified by a bicyclic cycloalkyl fused to a monocyclic, cycloalkyl, or a bridged bicyclic cycloalkyl in which two non-adjacent carbon atoms of the bicyclic ring system are linked by an alkylene bridge of between one and four carbon atoms. Representative examples of tricyclic-ring systems include, but are not, limited to, tricyclo[3.3.1.0$^{3,7}$]nonane and tricyclo[3.3.1.1$^{3,7}$]decane (adamantane). The monocyclic, bicyclic, and tricyclic cycloalkyls cart be attached to the parent molecular moiety through any substitutable atom contained within the rings and can be unsubstituted or substituted.

The term "cycloalkylalkyl" as used herein, means a cycloalkyl group, as defined herein, appended to the parent molecular moiety through an alkyl group, as defined herein. Representative, examples of cycloalkylalkyl include, but are not limited to, cyclopropylmethyl, 2-cyclobutylethyl, cyclopentylmethyl and cyclohexylmethyl.

The term "cycloalkenyl" of "cycloalkene" as used herein, means a monocyclic of a bicyclic hydrocarbon ring system. The monocyclic cycloalkenyl has four-, five-, six-, seven- or eight carbon atoms and zero heteroatom. The four-membered ring systems have one double bond, the five-pr six-membered ring systems have one or two double bonds, and the seven- or eight-membered ring systems have one, two or three double bonds. The monocyclic cycloalkenyl can be attached to the parent molecular moiety through any substitutable atom contained within the monocyclic cycloalkenyl. Representative examples of monocyclic cycloalkenyl groups include, but are not limited to cyclobutenyl, cyclopentenyl, cyclohexenyl, cycloheptenyl and cyclooctenyl. The bicyclic cycloalkenyl is a monocyclic cycloalkenyl fused to a monocyclic cycloalkyl group, or a monocyclic cycloalkenyl fused to a monocyclic cycloalkenyl group. The monocyclic or bicyclic cycloalkenyl ring can contain one or two alkylene bridges, each including one, two, three, or four carbon atoms and each linking two adjacent or non-adjacent carbon atoms of the monocyclic or bicyclic ring system. The cycloalkenyl of the present invention can be attached to the parent molecular moiety through any substitutable atom contained within the ring system. Representative examples of the bicyclic cycloalkenyl groups include, but are not limited to, 4,5,6,7-tetrahydro-3aH-indene, octahydronaphthalenyl and 1,6-dihydro-pentalene. The monocyclic and bicyclic cycloalkenyl groups of the present invention can be unsubstituted or substituted.

The term "cycloalkenylalkyl" as used herein, means a cycloalkenyl group, as defined herein, appended to the parent molecular moiety through an alkyl group, as defined herein.

The term "ethylenedioxy" as used herein, means a —O—(CH$_2$)$_2$—O— group wherein the oxygen atoms of the ethylenedioxy group are attached to two adjacent carbon atoms of a phenyl or naphthyl moiety, forming a six membered ring with the two adjacent carbon atoms of the phenyl or naphthyl moiety that it is attached to.

The term "halo" or "halogen" as used herein, means Cl, Br, I or F.

The term "haloalkyl" as used herein, means an alkyl group, as defined herein, in which one, two, three, four, five or six hydrogen atoms are replaced by halogen. Representative examples of haloalkyl include, but are not limited to, chloromethyl, 2-fluoroethyl, trifluoromethyl, difluoromethyl, pentafluoroethyl, and 2-chloro-3-fluoropentyl.

The term "heterocycle" or "heterocyclic" as used herein, means a monocyclic heterocycle, a bicyclic, or a tricyclic heterocycle. The monocyclic heterocycle is a three-, four-, five-, six- or seven-membered ring containing at least one heteroatom independently selected from the group including, but not limited to, O, N, and S. The three- or four-membered ring contains zero or one double bond, and one heteroatom selected from the group including, but not limited to, O, N and S. The five-membered ring contains zero or one double bond and one, two or three heteroatoms selected from the group including, but not limited to, O, N and S. The six-membered ring contains zero, one or two double bonds and one, two or three heteroatoms selected from the group including, but not limited to, O, N and S. The seven-membered ring contains zero, one, two, or three double bonds and one, two or three heteroatoms selected from the group including, but not limited to, O, N and S. Representative examples of monocyclic heterocycles include, but are hot limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl (including piperidin-1-yl), pyranyl, pyrazolinyl, pyrazolidinyl, pyrrolinyl, pyrrolidinyl, tetrahydrofuranyl, tetrahydropyranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused, to a monocyclic cycloalkenyl, a monocyclic heterocycle fused to a monocyclic heterocycle, or a bridged monocyclic heterocycle ring system in which two non adjacent atoms of the ring are linked by an alkylene bridge containing one, two, three; or four carbon atoms. Representative examples of bicyclic heterocycles include, but are hot limited to, benzopyranyl, benzothiopyranyl, 2,3-dihydrobenzofuranyl, 2,3-dihydrobenzothienyl, and 2,3-dihydro-1H-indolyl. Tricyclic heterocycles are exemplified by a bicyclic heterocycle fused to a phenyl group, or a bicyclic heterocycle fused to a monocyclic cycloalkyl, of a bicyclic heterocycle fused to a monocyclic cycloalkenyl, or a bicyclic heterocycle fused to a monocyclic heterocycle, or a bridged bicyclic heterocycle in which two non adjacent atoms of the bicyclic ring are linked by an alkylene bridge including, but not limited to, one, two, three, or four carbon atoms. Examples of tricyclic heterocycle are, but not limited to, oxaadamantane and aza-admantane. The monocyclic, bicyclic, and tricyclic heterocycles are connected to the parent molecular moiety through any carbon atom or any nitrogen atom contained within the monocyclic, bicyclic, and tricyclic heterocycle rings, and can be unsubstituted or substituted.

the term "heterocyclealkyl" as used herein, means a heterocycle, as defined herein, appended to the parent molecular moiety through an alkyl group, as defined herein.

The term "heteroaryl" as used herein, means a monocyclic heteroaryl, or a bicyclic heteroaryl. The monocyclic heteroaryl is a five- or six-membered ring. The five-membered ring contains two double bonds. The five-membered ring can contain one heteroatom selected from O or S; or one, two, or three nitrogen atoms and optionally one additional heteroatom selected from oxygen or sulfur; or four nitrogen atoms. The six-membered ring contains three double bonds and one, two, three or four nitrogen atoms. Representative examples of monocyclic heteroaryl include, but are not limited to, furanyl, imidazolyl, isoxazolyl, isothiazolyl, oxadiazolyl, 1,3-oxazolyl (including 1,3-oxazol-2-yl), pyridinyl (including pyridin-3-yl, pyridin-2-yl), pyridazinyl, pyrimidinyl, pyrazinyl, pyrazolyl, pyrrolyl, tetrazolyl, thiadiazolyl, 1,3-thiazolyl (including 1,3-thiazol-2-yl), thienyl, triazolyl, and triazinyl. The bicyclic heteroaryl includes of a monocyclic heteroaryl fused to a phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Representative examples of bicyclic heteroaryl groups include, but not limited to, benzofuranyl, benzothienyl, benzoxazolyl (including 1,3-benzoxazol-2-yl), benzimidazolyl, benzoxadiazolyl, benzothiazolyl (including 1,3-benzothiazol-2-yl), 6,7-dihydro-1,3-benzothiazolyl, imidazo[1,2-a]pyridinyl, indazolyl, indolyl, isoindolyl, isoquinolinyl, naphthyridinyl, pyridoimidazolyl, quinolinyl, thiazolo[5,4-b]pyridin-2-yl, thiazolo[5,4-d]pyrimidin-2-yl, and 5,6,7,8-tetrahydroquinolin-5-yl. The monocyclic and bicyclic heteroaryl groups of the present invention can be substituted or unsubstituted, and are connected to the parent molecular moiety through any carbon atom or any nitrogen atom contained within the ring system.

The term "heteroarylalkyl" as used herein, means a heteroaryl, as defined herein, appended to the parent molecular moiety through an alkyl group, as defined herein.

The term "heteroatom" as used herein, means a nitrogen, oxygen or sulfur atom.

The term "methylenedioxy" as used herein, means a —O—(CH$_2$)—O— group wherein the oxygen atoms of the methylenedioxy group are attached to two adjacent carbon atoms of the phenyl or naphthyl ring, forming a five membered ring with the two adjacent carbon atoms of the phenyl or naphthyl moiety that it is attached to.

The term "oxo" as used herein, means a =O group.

"Mammal" includes humans and domestic animals, such as cats, dogs, swine, cattle, horses, and the like.

Compounds of the invention have the formula (I) as described above.

Particular values of variable groups in compounds of formula (I) are as follows. Such values can be used where appropriate with any of the other values, definitions, claims or embodiments defined hereinbefore or hereinafter.

In compounds of formula (I), $G^1$ is phenyl or monocyclic heteroaryl (for example, pyridinyl, pyrimidinyl, pyrazinyl, pyridazinyl, 1,3-thiazolyl, 1,3-oxazolyl, and the like), each of which is optionally further substituted with 1, 2, 3 or 4 substituents as represented by T, and T is as defined in the summary section.

In one embodiment, $G^1$ is phenyl optionally further substituted as disclosed hereinabove.

In another embodiment, $G^1$ is a monocyclic heteroaryl, optionally further substituted as described hereinabove. For example, $G^1$ is pyridinyl, unsubstituted or further substituted as described in the summary section.

$G^2$ is phenyl or monocyclic heteroaryl (for example, pyridinyl, pyrimidinyl, pyrazinyl, pyridazinyl, 1,3-thiazolyl, 1,3-oxazolyl, and the like), each of which is optionally further substituted with 1, 2, 3 or 4 substituents as represented by T, and T is as defined in the summary section.

In one embodiment, $G^2$ is phenyl, optionally further substituted as disclosed hereinabove.

In another embodiment, $G^2$ is a monocyclic heteroaryl, optionally further substituted as described hereinabove. Particular examples of $G^2$ are 1,3-thiazolyl, 1,3-oxazolyl and pyridinyl, each of which is optionally further substituted as disclosed in the summary.

Examples of the optional substituents of $G^1$ and $G^2$, as represented by T include, but are not limited to, halogen, and $C_{1-6}$ alkyl such as methyl, ethyl, and the like.

$G^3$ is formula (a) or formula (b), wherein $W^1$, $W^2$, $W^3$, $W^4$, $R^3$, $R^4$, $R^5$, $R^6$, $R^c$, $R^d$, $L^1$ and X are as defined in the summary section.

In one embodiment, $G^3$ is formula (a), wherein $W^1$, $W^2$, $W^3$, $W^4$, $R^3$, $R^4$, $R^5$, and $R^6$ are as disclosed in the summary section. For example, $G^3$ is formula (a), wherein $W^1$ is —C($R^3$)($R^4$)— or —C($R^3$)($R^4$)—C($R^3$)($R^4$)—, and $W^2$ is N, and $W^3$, $W^4$, $R^3$, $R^4$, $R^5$, and $R^6$ are as disclosed in the summary section. Other examples of $G^3$ as formula (a) include, those wherein $W^1$ is —C($R^3$)($R^4$)— or —C($R^3$)($R^4$)—C($R^3$)($R^4$)—, and $W^2$ is —C($R^7$)—, and $W^3$, $W^4$, $R^3$, $R^4$, $R^5$, $R^6$, and $R^7$ are as disclosed in the summary section. $R^3$, $R^4$, $R^5$, and $R^6$, for example, are hydrogen.

In another embodiment, $G^3$ is formula (b), wherein $R^c$, $R^d$, $L^1$ and X are as defined in the summary section.

In yet another embodiment, $G^3$ is formula (b) wherein $L^1$ is O, N(H) or N(alkyl), and X is —(CR$^g$R$^h$)$_u$-tertrazolyl, heterocyclealkyl, heteroarylalkyl, hydrogen, alkyl, haloalkyl, —C(O)O(R$^{10}$), —C(O)N(R$^{10}$)(R$^{11}$), —(CR$^g$R$^h$)$_u$—OR$^{10}$, —(CR$^g$R$^h$)$_u$—N(R$^{10}$)(R$^{11}$), —(CR$^g$R$^h$)$_u$—CN, —(CR$^g$R$^h$)$_u$—C(O)O(R$^{10}$), or —(CR$^g$R$^h$)$_u$—C(O)N(R$^{10}$)(R$^{11}$), wherein $R^{10}$, $R^{11}$, $R^g$, $R^h$, and u are as defined in the summary. Examples of X include, but are not limited to, hydrogen, $C_{1-6}$ alkyl (for example, methyl, ethyl, and the like), and —(CR$^g$R$^h$)$_u$—C(O)O(R$^{10}$) wherein $R^g$, $R^h$, u, and $R^{10}$ are as defined in the summary. In one embodiment, $R^{10}$ is hydrogen, and $R^g$ and $R^h$, at each occurrence, are each independently selected from the group including, but not limited to, hydrogen and $C_{1-6}$ alkyl (for example, methyl, ethyl, and the like). In brie embodiment, u is 1or 2. Particularly, u is 1.

In yet another embodiment, $G^3$ is formula (b) wherein $L^1$ is —(CR$^p$R$^q$)$_s$— and X is —C(O)OH or tetrazolyl, wherein $R^p$, $R^q$, and s are as defined in the summary. In one embodiment, X is —C(O)OH. Examples of $R^p$ and $R^q$ include hydrogen and alkyl (for example, methyl, ethyl, and the like). In one embodiment, $R^p$ and $R^q$ are hydrogen and s is 1.

In one embodiment, $R^c$ and $R^d$, together with the carbon atom to which they are attached, is a 3-6 membered cycloalkyl (for example, cyclobutyl, cyclopentyl, and the like), wherein 1, 2, 3 of 4 hydrogen atoms attached to the ring carbon of the cycloalkyl are optionally replaced as disclosed in the summary section. For example, one of the hydrogen atom attached to the ring carbon atom is optionally replaced by —C(O)OH.

In yet another embodiment, $R^c$ and $R^d$, together with the carbon atom to which they are attached, is a monocyclic heterocycle of formula (c) as described in the summary. For example, $R^c$ and $R^d$, together with the carbon atom to which they are attached, is a monocyclic heterocycle of formula (c) wherein $W^5$ is —CH$_2$— or —CH$_2$—CH$_2$— and $W^6$ is O or N($R^x$); wherein $R^x$ is as defined in the summary. For example, $R^x$ is $C_{1-6}$ alkyl (for example, methyl, ethyl, and the like), or —C(O)O($C_{1-6}$ alkyl).

Q is alkyl, alkenyl, alkynyl, haloalkyl, $G^4$, —Y$^1$—Y$^3$, —Y$^1$—(CR$^j$R$^k$)$_v$—Y$^2$—Y$^4$, or formula (d) wherein $G^4$, Y$^1$, Y$^3$, $R^j$, $R^k$, v, Y$^2$, Y$^4$, and Z are as defined in the summary section. For example, Q is $G^4$, —Y$^1$—Y$^3$, —Y$^1$—(CR$^j$R$^k$)$_v$—Y$^2$—Y$^4$, or formula (d) wherein $G^4$, Y$^1$, Y$^3$, $R^j$, $R^k$, v, Y$^2$, Y$^4$, and Z are as defined in the summary section.

In one embodiment, Q is $G^4$ wherein $G^4$ is as disclosed in the summary. For example, $G^4$ is aryl (for example, phenyl) of heteroaryl (for example, 1,3-benzoxazolyl, 1,3-benzothiazolyl), each of which is optionally further substituted as described in the summary section. Examples of the optional substituents of $G^4$ include, but are not limited to, $C_{1-6}$ alkyl (for example, methyl, ethyl, and the like), halogen, haloalkyl (for example, trifluoromethyl), or —OR$^1$ wherein $R^1$ is C1-6 alkyl or haloalkyl (e.g. trifluoromethyl).

In another embodiment, Q is —Y$^1$—Y$^3$ wherein —Y$^1$ and Y$^3$ are as defined in the summary. For example, Y$^1$ is —C(O)—, —C(O)O—, or —C(O)N(R$^w$)— wherein the right side of the —C(O)O— and —C(O)N(R$^w$)— moieties are attached to Y$^3$, and R$^w$ is as defined in the summary. Examples of Y$^3$ include, but are not limited to, aryl (for example, phenyl, bicyclo[4.2.0]octa-1,3,5-trien-7-yl, and the like), heterocycle (for example, piperidinyl), cycloalkyl (for example, cyclobutyl, cyclopentyl, cyclohexyl, and the like) and arylalkyl (for example, benzyl) wherein each of the aryl, heterocycle, cycloalkyl and the aryl moiety of the arylalkyl is independently optionally further substituted as described in the summary. Examples of the optional substituents include, but are not limited to, $C_{1-6}$ alkyl (for example, methyl, and the like), halogen and haloalkyl (for example, trifluoromethyl). In certain embodiments, $R^w$ is hydrogen.

In another embodiment, Q is formula (d) wherein Z is as defined in the summary. For example, Z is $G^4$ wherein $G^4$ is as defined in the summary. In one embodiment, $G^4$ is aryl (for example, phenyl), unsubstituted or further substituted as disclosed in the summary. In another embodiment, $G^4$ is heteroaryl, unsubstituted or further substituted as disclosed in the summary. Examples of the optional substituents include, but are not limited to, halogen, $C_{1-6}$ alkyl (for example, methyl), and haloalkyl (for example, trifluoromethyl).

It is appreciated that the present invention contemplates compounds of formula (I) with combinations of the above embodiments, including particular, more particular and preferred embodiments.

Accordingly, one aspect of the invention relates to compounds of formula (II) of pharmaceutically acceptable salts, prodrugs, salts of prodrugs, or a combination thereof,

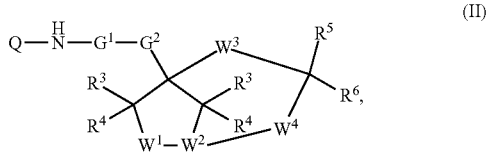

(II)

wherein Q, $G^1$, $G^2$, $R^3$, $R^4$, $R^5$, $R^6$, $W^1$, $W^2$, $W^3$, and $W^4$ are as disclosed in the summary. For example, $W^1$ is —C($R^3$)($R^4$)— or —C($R^3$)($R^4$)—C($R^3$)($R^4$)—, $W^2$ is N, and Q, $G^1$, $G^2$, $W^3$, $W^4$, $R^3$, $R^4$, $R^5$, and $R^6$ are as disclosed in the summary section. For example, $R^3$, $R^4$, $R^5$, and $R^6$ are hydrogen. $W^3$, $W^4$, $G^1$, $G^2$ and Q have the meanings as disclosed hereinabove. $G^1$ and $G^2$ are each independently phenyl or monocyclic heteroaryl, optionally substituted as described in the summary. Examples of $G^1$ include, but not limited to, phenyl and pyridinyl, each of which is independently unsubstituted or further substituted as described in the summary section. Examples of $G^2$ include, but are not limited to, phenyl, pyridinyl, 1,3-thiazolyl, and 1,3-oxazolyl, each of which is optionally further substituted with 1, 2, 3 or 4 substituents as represented by T, and T is as defined in the summary section. Examples of the optional substituents of $G^1$ and $G^2$, as represented by T include, but are not limited to, halogen, and $C_{1-6}$ alkyl such as methyl, ethyl, and the like. Examples of Q include $G^4$, —$Y^1$—$Y^3$, —$Y^1$—(C$R^j R^k$)$_v$—$Y^2$—$Y^4$, or formula (d) wherein $G^4$, $Y^1$, $Y^3$, $R^j$, $R^k$, v, $Y^2$, $Y^4$, and Z have the meanings as disclosed hereinabove. In certain embodiments, $W^1$ is $CH_2$, $W^2$ is N, $W^3$ is O and $W^4$ is $CH_2$.

Other examples of compounds of formula (II) include those wherein $W^1$ is —C($R^3$)($R^4$)— or —C($R^3$)($R^4$)—C($R^3$)($R^4$)—, $W^2$ is —C($R^7$)—, and $W^3$, $W^4$, $R^3$, $R^4$, $R^5$, $R^6$, and $R^7$ are as disclosed in the summary section. In one embodiment, $R^7$ is —C(O)OH. $R^3$, $R^4$, $R^5$, and $R^6$ are, for example, hydrogen. $W^3$, $W^4$, $G^1$, $G^2$ and Q have the meanings as disclosed hereinabove. $G^1$ and $G^2$ are each independently phenyl or monocyclic heteroaryl, optionally substituted as described in the summary. Examples of $G^1$ include, but not limited to, phenyl and pyridinyl, each of which is independently unsubstituted or further substituted as described in the summary section. Examples of $G^2$ include, but are not limited to, phenyl, pyridinyl, 1,3-thiazolyl, and 1,3-oxazolyl, each of which is optionally further substituted with 1, 2, 3 or 4 substituents as represented by T, and T is as defined in the summary section. Examples of the optional substituents of $G^1$ and $G^2$, as represented by T include, but are not limited to, halogen, and $C_{1-6}$ alkyl such as methyl, ethyl, and the like. Examples of Q include $G^4$, —$Y^1$—$Y^3$, —$Y^1$—(C$R^j R^k$)$_v$—$Y^2$—$Y^4$, or formula (d) wherein $G^4$, $Y^1$, $Y^3$, $R^j$, $R^k$, v, $Y^2$, $Y^4$, and Z have the meanings as disclosed hereinabove.

Another aspect of the invention relates to compounds of formula (III), of pharmaceutically acceptable salts, prodrugs, salts of prodrugs, or a combination thereof,

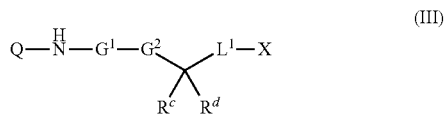

(III)

wherein Q, $G^1$, $G^2$, $R^c$, $R^d$, $L^1$ and X have the meanings as disclosed hereinabove.

Yet another aspect of the invention relates to compounds of formula (III), or pharmaceutically acceptable salts, salts of prodrugs, or a combination thereof, wherein $L^1$ is O, and Q, $G^1$, $G^2$, $R^c$, $R^d$, and X have the meanings as disclosed hereinabove. Examples of X include, but are not limited to, hydrogen, alkyl such as $C_{1-6}$ alkyl (for example, methyl, ethyl, and the like), and —(C$R^g R^h$)$_u$—C(O)O($R^{10}$) wherein $R^g$, $R^h$, u, and $R^{10}$ are as defined in the summary. In one embodiment, X is —(C$R^g R^h$)$_u$—C(O)O($R^{10}$). $R^g$ and $R^h$, at each occurrence, are each independently selected from the group including, but not limited to, hydrogen and $C_{1-6}$ alkyl (for example, methyl, ethyl, and the like). In one embodiment, u is 1 or 2. Particularly, u is 1. In another embodiment, X is hydrogen or $C_{1-6}$ alkyl (for example, methyl, ethyl, and the like). $G^1$ and $G^2$ are each independently aryl or monocyclic heteroaryl, optionally further substituted as described in the summary. Examples of $G^1$ include, but are not limited to, phenyl and pyridinyl, each of which is independently unsubstituted or further substituted as described in the summary section. Examples of $G^2$ include, but are not limited to, phenyl, pyridinyl, 1,3-thiazolyl, and 1,3-oxazolyl, each of which is optionally further substituted with 1, 2, 3 of 4 substituents as represented by T, and T is as defined in the summary section and in the Detailed Description. Examples of Q include $G^4$, —$Y^1$—$Y^3$, —$Y^1$—(C$R^j R^k$)$_v$—$Y^2$—$Y^4$, or formula (d) wherein $G^4$, $Y^1$, $Y^3$, $R^j$, $R^k$, v, $Y^2$, $Y^4$, and Z have the meanings as disclosed hereinabove.

Of this group of compounds of formula (III), examples of a subgroup include those wherein $R^c$ and $R^d$, together with the carbon atom to which they are attached, is a 3-6 membered cycloalkyl (for example, cyclobutyl, cyclopentyl, and the like) wherein 1, 2, 3, or 4 hydrogen atoms attached to the ring carbon of the cycloalkyl ring are optionally replaced with radicals as disclosed in the summary. For example, one of the hydrogen atom attached to the ring carbon of the cycloalkyl ring is optionally replaced by —C(O)OH.

Of this group of compounds of formula (III), examples of another subgroup include those wherein $R^c$ and $R^d$, together with the carbon atom to which they are attached, is a monocyclic heterocycle of formula (c) wherein 1, 2, 3, or 4 hydrogen atoms attached to the ring carbon of the monocyclic heterocycle ring are optionally replaced with radicals, and the radicals, $W^5$ and $W^6$ are as disclosed in the summary. For example, $R^c$ and $R^d$, together with the carbon atom to which they are attached, is a monocyclic heterocycle of formula (c) wherein $W^5$ is —$CH_2$— or —$CH_2$—$CH_2$— and $W^6$ is O or $N(R^x)$, wherein $R^x$ is as defined, in the summary. For example, $R^x$ is $C_{1-6}$ alkyl (for example, methyl, ethyl, and the like) or —C(O)O($C_{1-6}$ alkyl).

Yet another aspect of the invention relates to compounds of formula (III), or pharmaceutically acceptable salts, prodrugs, salts of prodrugs, or a combination thereof, wherein $L^1$ is N(H) or N(alkyl), and Q, $G^1$, $G^2$, $R^c$, $R^d$, and X have the meanings as disclosed hereinabove. Examples of X include, but are hot limited to, hydrogen, alkyl such as $C_{1-6}$ alkyl (for example, methyl, ethyl, and the like), and —$(CR^gR^h)_u$—C(O)O($R^{10}$) wherein $R^g$, $R^h$, u, and $R^{10}$ are as defined in the summary. In one embodiment, X is —$(CR^gR^h)_u$—C(O)O($R^{10}$). $R^g$ and $R^h$, at each occurrence, are each independently selected from the group including, but not limited to, hydrogen and $C_{1-6}$ alkyl (for example, methyl, ethyl, and the like). In one embodiment, u is 1 or 2. Particularly, u is 1. In another embodiment, X is hydrogen or $C_{1-6}$ alkyl (for example, methyl, ethyl, and the like). $G^1$ and $G^2$ are each independently aryl or monocyclic heteroaryl, optionally further substituted as described in the summary. Examples of $G^1$ include, but are not limited to, phenyl and pyridinyl, each of which is independently unsubstituted or further substituted as described in the summary section. Examples of $G^2$ include, but are hot limited to, phenyl, pyridinyl, 1,3-thiazolyl, and 1,3-oxazolyl, each of which is optionally further substituted with 1, 2, 3 or 4 substituents as represented by T, and T is as defined in the summary section. Examples of Q include $G^4$, —$Y^1$—$Y^3$, —$Y^1$—$(CR^jR^k)_v$—$Y^2$—$Y^4$, or formula (d) wherein $G^4$, $Y^1$, $Y^3$, $R^j$, $R^k$, v, $Y^2$, $Y^4$, and Z have the meanings as disclosed hereinabove.

Of this group of compounds of formula (III), examples of a subgroup include those wherein $R^c$ and $R^d$, together with the carbon atom to which they are attached, is a 3-6 membered cycloalkyl (for example, cyclobutyl, cyclopentyl, and the like) wherein 1, 2, 3, or 4 hydrogen atoms attached to the ring carbon of the cycloalkyl ring are optionally replaced with radicals, as disclosed in the summary. For example, one of the hydrogen atom attached to the ring carbon of the cycloalkyl ring is optionally replaced by —C(O)OH.

Of this group of compounds of formula (III), examples of another subgroup include those wherein $R^c$ and $R^d$, together with the carbon atom to which they are attached, is a monocyclic heterocycle of formula (c) wherein 1, 2, 3, or 4 hydrogen atoms attached to the ring carbon of the monocyclic heterocycle ring are optionally replaced with radicals, and the radicals, $W^5$ and $W^6$ are as disclosed in the summary. For example, $R^c$ and $R^d$, together with the carbon atom to which they are attached, is a monocyclic heterocycle of formula (c) wherein $W^5$ is —$CH_2$— or —$CH_2$—$CH_2$— and $W^6$ is O or $N(R^x)$; wherein $R^x$ is as defined in the summary. For example, $R^x$ is $C_{1-6}$ alkyl (for example, methyl, ethyl, and the like), or —C(O)O($C_{1-6}$ alkyl).

A further aspect of the invention relates to compounds of formula (III), or pharmaceutically acceptable salts, prodrugs, salts of prodrugs, or a combination thereof, wherein $L^1$ is —$(CR^pR^q)_s$—, and Q, $G^1$, $G^2$, $R^c$, $R^d$, $R^p$, $R^q$, s, and X have the meanings as disclosed hereinabove. In one embodiment, X is —C(O)OH. $R^p$ and $R^q$, at each occurrence, are each independently selected from the group including, but not limited to, hydrogen and $C_{1-6}$ alkyl (for example, methyl, ethyl, and the like). In one embodiment, s is 1. $G^1$ and $G^2$ are each independently aryl or monocyclic heteroaryl, optionally further substituted as described in the summary. Examples of $G^1$ include, but are not limited to, phenyl and pyridinyl, each of which is independently unsubstituted or further substituted as described in the summary section. Examples of $G^2$ include, but are not limited to, phenyl, pyridinyl, 1,3-thiazolyl, and 1,3-oxazolyl, each of which is optionally further substituted with 1, 2, 3 or 4 substituents as represented by T, and T is as defined in the summary section. Examples of Q include $G^4$, —$Y^1$—$Y^3$, —$Y^1$—$(CR^jR^k)_y$—$Y^2$—$Y^4$, or formula (d) wherein $G^4$, $Y^1$, $Y^3$, $R^j$, $R^k$, y, $Y^2$, $Y^4$, and Z have the meanings as disclosed hereinabove.

Of this group of compounds of formula (III), examples of a subgroup include those wherein $R^c$ and $R^d$, together with the carbon atom to which they are attached, is a 3-6 membered cycloalkyl (for example, cyclobutyl, cyclopentyl, and the like) wherein 1, 2, 3, or 4 hydrogen atoms attached to the ring carbon of the cycloalkyl ring are optionally replaced with radicals, as disclosed in the summary. For example, one of the hydrogen atom attached to the ring carbon of the cycloalkyl ring is optionally replaced by —C(O)OH.

Of this group of compounds of formula (III), examples of another subgroup include those wherein $R^c$ and $R^d$, together with the carbon atom to which they are attached, is a heterocycle of formula (c) wherein 1, 2, 3, or 4 hydrogen atoms attached to the ring carbon of the monocyclic heterocycle, are optionally replaced with radicals, and the radicals, $W^5$ and $W^6$ are as disclosed in the summary. For example, $R^c$ and $R^d$, together with the carbon atom to which they are attached, is a monocyclic heterocycle of formula (c) wherein $W^5$ is —$CH_2$— or —$CH_2$—$CH_2$— and $W^6$ is O or $N(R^x)$; wherein $R^x$ is as defined in the summary. For example, $R^x$ is $C_{1-6}$ alkyl (for example, methyl, ethyl, and the like), or —C(O)O($C_{1-6}$ alkyl).

Exemplary compounds of the present invention include, but are not limited to the following:

N-[2-fluoro-5-(trifluoromethyl)phenyl]-N'-{4-[2-(4-hydroxytetrahydro-2H-pyran-4-yl)-1,3-thiazol-5-yl]phenyl}urea;

N-{4-[2-(1-ethyl-4-hydroxypiperidin-4-yl)-1,3-thiazol-5-yl]phenyl}-N'-[2-fluoro-5-(trifluoromethyl)phenyl]urea;

4-(5-{4-[(5,7-dimethyl-1,3-benzoxazol-2-yl)amino]-3-fluorophenyl}-1,3-thiazol-2-yl)tetrahydro-2H-pyran-4-ol;

4-(5-{4-[(7-methyl-1,3-benzoxazol-2-yl)amino]phenyl}-1,3-thiazol-2-yl)tetrahydro-2H-pyran-4-ol;

4-(5-{2-chloro-4-[(7-chloro-1,3-benzoxazol-2-yl)amino]phenyl}-1,3-thiazol-2-yl)tetrahydro-2H-pyran-4-ol;

4-(5-{4-[(7-chloro-1,3-benzoxazol-2-yl)amino]-2-methylphenyl}-1,3-thiazol-2-yl)tetrahydro-2H-pyran-4-ol;

N-[2-fluoro-5-(trifluoromethyl)phenyl]-N'-{6-[2-(4-hydroxytetrahydro-2H-pyran-4-yl)-1,3-thiazol-5-yl]pyridin-3-yl}urea;

N-{4-[2-(1-ethyl-4-hydroxypiperidin-4-yl)-1,3-thiazol-5-yl]-2-fluorophenyl}-N'-[2-fluoro-5-(trifluoromethyl)phenyl]urea;

N-(2,5-difluorophenyl)-N'-{4-[2-(1-ethyl-4-hydroxypiperidin-4-yl)-1,3-thiazol-5-yl]-2-fluorophenyl}urea;

N-[2-fluoro-5-(trifluoromethyl)phenyl]-N'-{6-[2-(1-hydroxycyclopentyl)-1,3-thiazol-5-yl]pyridin-3-yl}urea;

phenyl 4-[2-(4-hydroxytetrahydro-2H-pyran-4-yl)-1,3-thiazol-5-yl]phenylcarbamate;

N-{4-[2-(4-hydroxytetrahydro-2H-pyran-4-yl)-1,3-thiazol-5-yl]phenyl}piperidine-1-carboxamide;

tert-butyl 3-(5-{4-[({[2-fluoro-5-(trifluoromethyl)phenyl]amino}carbonyl)amino]phenyl}-1,3-thiazol-2-yl)-3-hydroxypyrrolidine-1-carboxylate;

N-[2-fluoro-5-(trifluoromethyl)phenyl]-N'-{4-[2-(3-hydroxypyrrolidin-3-yl)-1,3-thiazol-5-yl]phenyl}urea;

N-[2-fluoro-5-(trifluoromethyl)phenyl]-N'-{4-[2-(3-hydroxy-1-methylpyrrolidin-3-yl)-1,3-thiazol-5-yl]phenyl}urea;

N-{4-[2-(1-ethyl-3-hydroxypyrrolidin-3-yl)-1,3-thiazol-5-yl]phenyl}-N'-[2-fluoro-5-(trifluoromethyl)phenyl]urea;

N-[2-fluoro-5-(trifluoromethyl)phenyl]-N'-{4-[2-(1-hydroxycyclopentyl)-1,3-thiazol-5-yl]phenyl}urea;

N-{4-[2-(1-hydroxycyclobutyl)-1,3-thiazol-5-yl]phenyl}-N'-[3-(trifluormethyl)phenyl]urea;

N-[2-fluoro-5-(trifluoromethyl)phenyl]-N'-{4-[2-(1-hydroxycyclobutyl)-1,3-thiazol-5-yl]phenyl}urea;

N-{4-[2-(1-hydroxycyclobutyl)-1,3-thiazol-5-yl]phenyl}-N'-[3-(trifluoromethyl)phenyl]urea;

(±)-Cis-3-hydroxy-3-{4'-[({[3-(trifluoromethyl)phenyl]amino}carbonyl)amino]-1,1'-biphenyl-4-yl}cyclopentanecarboxylic acid;

N-[2-fluoro-5-(trifluoromethyl)phenyl]-N'-{4-[2-(1-methoxycyclopentyl)-1,3-thiazol-5-yl]phenyl}urea;

{[1-(5-{4-[({[2-fluoro-5-(trifluoromethyl)phenyl]amino}carbonyl)amino]phenyl}-1,3-thiazol-2-yl)cyclopentyl]oxy}acetic acid;

{[1-(5-{4-[(bicyclo[4.2.0]octa-1,3,5-trien-7-ylcarbonyl)amino]phenyl}-1,3-thiazol-2-yl)cyclobutyl]oxy}acetic acid;

({1-[5-(4-{[(2-fluorophenyl)acetyl]amino}phenyl)-1,3-thiazol-2-yl]cyclobutyl}oxy)acetic acid;

{[1-(5-{4-[(anilinocarbonyl)amino]phenyl}-1,3-thiazol-2-yl)cyclopentyl]oxy}acetic acid;

{[1-(5-{4-[(anilinocarbonyl)amino]phenyl}-1,3-thiazol-2-yl)cyclobutyl]oxy}acentic acid;

{[1-(5-{6-[(anilinocarbonyl)amino]pyridin-3-yl}-1,3-thiazol-2-yl)cyclopentyl]oxy}acetic acid;

{[1-(5-{6-[({[3-(trifluoromethyl)phenyl]amino}carbonyl)amino]pyridin-3-yl}-1,3-thiazol-2-yl)cyclopentyl]oxy}acetic acid;

{[1-(4-{6-[(anilinocarbonyl)amino]pyridin-3-yl}phenyl)cyclopentyl]oxy}acetic acid;

(±)-Cis-3-(4'-{[(2-fluorophenyl)acetyl]amino}-1,1'-biphenyl-4-yl)-3-hydroxycyclopentanecarboxylic acid;

[(1-{5-[4-({2-[(4-chlorophenyl)amino]-3,4-dioxocyclobut-1-en-1-yl}amino)phenyl]-1,3-thiazol-2-yl}cyclobutyl)oxy]acetic acid;

{[1-(5-{4-[(anilinocarbonyl)amino]phenyl}-4-methyl-1,3-thiazol-2-yl)cyclopentyl]oxy}acetic acid;

{[1-(4-methyl-5-{4-[({[3-(trifluoromethyl)phenyl]amino}carbonyl)amino]phenyl}-1,3-thiazol-2-yl)cyclopentyl]oxy}acetic acid;

{[1-(5-{6-[(anilinocarbonyl)amino]pyridin-3-yl}-4-methyl-1,3-thiazol-2-yl)cyclopethyl]oxy}acetic acid;

{[1-(4-methyl-5-{6-[({[3-(trifluoromethyl)phenyl]amino}carbonyl)amino]pyridin-3-yl}-1,3-thiazol-2-yl)cyclopentyl]oxy}acetic acid;

{[1-(5-{6-[({[2-fluoro-5-(trifluoromethyl)phenyl]amino}carbonyl)amino]pyridin-3-yl}-1,3-thiazol-2-yl)cyclopentyl]oxy}acetic acid;

2-{[1-(5-{6-[({[3-(trifluoromethyl)phenyl]amino}carbonyl)amino]pyridin-3-yl}-1,3-thiazol-2-yl)cyclopentyl]oxy}propanoic acid;

2-{[1-(5-{6-[(anilinocarbonyl)amino]pyridin-3-yl}-1,3-thiazol-2-yl)cyclopentyl]oxy}propanoic acid;

{[1-(5-{4-[(7-methyl-1,3-benzoxazol-2-yl)amino]phenyl}-1,3-thiazol-2-yl)cyclopentyl]oxy}acetic acid;

N-{4-[2-(4-hydroxytetrahydro-2H-pyran-4-yl)-1,3-thiazol-5-yl]phenyl}-2-[3-(trifluoromethyl)phenyl]acetamide;

2-(2,4-difluorophenyl)-N-{4-[2-(4-hydroxytetrahydro-2H-pyran-4-yl)-1,3-thiazol-5-yl]phenyl}acetamide;

2-(2,5-difluorophenyl)-N-{4-[2-(4-hydroxytetrahydro-2H-pyran-4-yl)-1,3-thiazol-5-yl]phenyl}acetamide;

[(1-{5-[4-(benzoylamino)phenyl]-1,3-thiazol-2-yl}cyclobutyl)oxy]acetic acid;

({1-[5-(4-{[(3-fluorophenyl)acetyl]amino}phenyl)-1,3-thiazol-2-yl]cyclobutyl}oxy)acetic acid;

({1-[5-(4-{[4-(trifluoromethyl)benzoyl]amino}phenyl)-1,3-thiazol-2-yl]cyclobutyl}oxy)acetic acid;

[(1-{5-[4-({[2-fluoro-5-(trifluoromethyl)phenyl]acetyl}amino)phenyl]-1,3-thiazol-2-yl}cyclobutyl)oxy]acetic acid;

{[1-(5-{6-[({[3-(trifluoromethyl)phenyl]amino}carbonyl)amino]pyridin-3-yl}-1,3-oxazol-2-yl)cyclopentyl]oxy}acetic acid;

({1-[5-(4-{[(2,5-difluorophenyl)acetyl]amino}phenyl)-1,3-thiazol-2-yl]cyclobutyl}oxy)acetic acid;

({-1-[5-(4-{[(3,5-difluorophenyl)acetyl]amino}phenyl)-1,3-thiazol-2-yl]cyclobutyl}oxy)acetic acid;

({-1-[5-(4-{[(3,4-difluorophenyl)acetyl]amino}phenyl)-1,3-thiazol-2-yl]cyclobutyl}oxy)acetic acid;

{[1-(4-{6-[({[3-(trifluoromethyl)phenyl]amino}carbonyl)amino]pyridin-3-yl}phenyl)cyclopentyl]oxy}acetic acid;

2-(1-(2-fluoro-4-(6-(3-(3-(trifluoromethyl)phenyl)ureido)pyridin-3-yl)phenyl)cyclopentyloxy)acetic acid;

1-(5-(4-(4-oxa-1-azabicyclo[3.2.1]octan-5-yl)phenyl)pyridin-2-yl)-3-phenylurea;

2-(1-(3-fluoro-4-(6-(3-(3-(trifluoromethyl)phenyl)ureido)pyridin-3-yl)phenyl)cyclopentyloxy)acetic acid;

2-(1-(3-fluoro-4-(6-(3-(3-(trifluoromethyl)phenyl)ureido)pyridin-3-yl)phenyl)cyclobutoxy)acetic acid;

[(1-{5-[4-({[(2-fluorphenyl)amino]carbonyl}amino)phenyl]pyridin-2-yl}cyclopentyl)oxy]acetic acid;

[1-(4-{6-[({[3-(trifluoromethyl)phenyl]amino}carbonyl)amino]pyridin-3-yl}phenyl)cyclopentyl]acetic acid;

(1-{4-[6-({[(2-fluorophenyl)amino]carbonyl}amino)pyridin-3-yl]phenyl}cyclopentyl)acetic acid;

{[1-(2-fluoro-4-{6-[({[3-(trifluormethyl)phenyl]amino}carbonyl)amino]pyridin-3-yl}phenyl)cyclobutyl]oxy}acetic acid;

[(1-{2-fluoro-4-[6-({[3-(trifluoromethyl)phenyl]acetyl}amino)pyridin-3-yl]phenyl}cyclobutyl)oxy]acetic acid; and {[1-(3-fluoro-4'-{[6-(trifluoromethoxy)-1,3-benzothiazol-2-yl]amino}-1,1'-biphenyl-4-yl)cyclobutyl]oxy}acetic acid;

or a pharmaceutically acceptable salt, prodrug, or salt of a prodrug thereof.

Compounds disclosed herein can contain asymmetrically substituted carbon or sulfur atoms, and accordingly can exist in, and be isolated in, single stereoisomers (e.g. single enantiomer or single diastereomer), mixtures of stereoisomers (e.g. any mixture of enantiomers or diastereomers) or facemic mixtures thereof. Individual optically-active forms of the compounds can be prepared for example, by synthesis from optically-active starting materials, by chiral synthesis, by enzymatic resolution, by biotransformation, or by chromatographic separation. It is to be understood that the present invention encompasses any racemic, optically-active, stereoisomers form, or mixtures of various proportions thereof, which form possesses properties useful in the inhibition of DGAT-1 activity. Where the stereochemistry of the chiral centers present in the chemical structures illustrated herein is not specified, the chemical structure is intended to encompass compounds containing either stereoisomer of each chiral center present in the compound.

Geometric isomers can exist in the present compounds. The invention contemplates the various geometric isomers and mixtures thereof resulting from the disposal of substituents around a carbon-carbon double bond, a cycloalkyl group, or a heterocycloalkyl group. Substituents around a carbon-carbon double bond are designated as being of Z or E configuration and substituents around a cycloalkyl or heterocycloalkyl are designated as being of cis or trans configuration.

Within the present invention it is to be understood that compounds disclosed herein can exhibit the phenomenon of tautomerism and that the formulae drawings within this specification can represent only one of the possible tautomeric forms. It is to be understood that the invention encompasses any tautomeric form and is not to be limited merely to any one tautomeric form utilized within the naming of the compounds or formulae drawings.

Synthetic Methods

This invention is intended to encompass compounds of the invention when prepared by synthetic processes or by metabolic processes. Preparation of the compounds of the invention by metabolic processes include those occurring in the human or animal body (in vivo) or processes occurring in vitro.

The synthesis of compounds of formula (I), (II), or (III), wherein the groups $R^c$, $R^d$, $R^g$, $R^h$, $R^3$, $R^4$, $R^{10}$, $G^1$, $G^2$, $G^3$, Q, $W^1$, $W^3$, X, and u, have the meanings as set forth in the summary section unless otherwise noted, is exemplified in Schemes 1-8.

As used in the descriptions of the schemes and the examples, certain abbreviations are intended to have the following meanings: DMSO for dimethylsulfoxide, RP-HPLC for preparative reverse phase high pressure liquid chromatography, Boc for tert-butoxycarbonyl, and OTs for p-tolylsulfonate.

Compounds of the invention were named by ACD/ChemSketch version 5.06 (developed by Advanced Chemistry Development, Inc., Toronto, ON, Canada) or were given names consistent with ACD nomenclature.

Compounds of general formula (I) can be prepared using the general procedures as outlined in Scheme 1.

Scheme 1

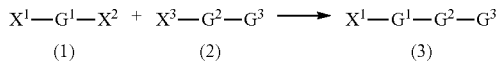

As illustrated in Scheme 1, compounds of formula (3) wherein $X^1$ is $NH_2$, $N(H)(P_g)$, $NO_2$ of $N(H)(Q)$ wherein $P_g$ is a nitrogen protecting group, can be prepared by palladium mediated coupling reaction between compounds of formula (1) and compounds of formula (2) wherein one of $X^2$ and $X^3$ is halogen, triflate or tosylate and the other is trialkyl(tin), boronic acid or boronic ester, for example, 1,3,2-dioxaborolan-2-yl of formula (4) wherein each $X^4$ is same or different and each is $C_{1-6}$ alkyl,

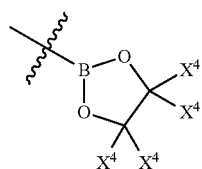

(4)

Appropriate reaction conditions and suitable values of $X^1$, $X^2$ and $X^3$ can readily be chosen for these reactions. For example, compounds of formula (1) wherein $X^2$ is halogen can be treated with compounds of formula (2) wherein $X^3$ is of formula (4) and $X^4$ is methyl, in the presence of a base such as potassium iodide, triethylamine, cesium carbonate, sodium carbonate, potassium phosphate, potassium fluoride, or cesium fluoride, a palladium catalyst such as tetrakis(triphenylphosphine)palladium(0), 1,1'-bis(di-tertbutylphosphino) ferrocene palladiumdichloride, or a palladium source modified with an appropriate ligand. Examples of palladium sources include, but are not limited to, tris(dibenzylideneacetone)dipalladium(0) and its chloroform adduct. Appropriate ligands include, but are not limited to, 2-dicyclohexylphosphino-2',6'-dimethoxybiphenyl and 2-dicyclohexylphosphino-2',6'-diisopropoxybiphenyl. The reaction is generally carried out at a temperature from about 60° C. to about 120° C., in an organic solvent such toluene, dioxane, N,N-dimethylsulfoxide, N,N-dimethyl acetamide, dimethylsulfoxide, dimethoxyethane, dimethylsulfoxide, isopropanol, ethanol, water, or mixture thereof, and optionally in a microwave Oven.

Intermediates of formula, (1) or (2) are either commercially available, known in the literature, or can be prepared by modifying reaction conditions known in the literature.

Alternatively, compounds of formula (3) can be prepared by treating (1) and (2) wherein one of $X^2$ and $X^3$ is hydrogen and the other is a displaceable functional group such as halogen, triflate or tosylate. The reaction can be carried out by first lithiating the compound containing an acidic hydrogen, employing a base such as n-butyllithium, at about −78° C., in a solvent such as tetrahydrofuran. The resulting lithiated species can then be treated with zinc halides such as zinc chloride at about −78° C., followed by treatment with compounds containing the displaceable functional group, in the presence of a palladium catalyst such as tetrakis(triphenylphosphine) palladium(0). The latter reaction is generally conducted at about 40° C. to about 100° C.

Intermediates of formula (2) wherein $X^3$ is hydrogen or halogen, $G^3$ is formula (b) and $L^1$ is O, can be prepared, for example by (a) reacting an aryl of heteroaryl group containing an acidic hydrogen, with a strong base such as n-butyllithium, or (b) by reacting an aryl halide or heteroaryl halide with an alkyllithium or alkyl Grignard reagent and (c) treating the resulting anion from step (a) or (b) with a ketone of formula (5), as shown in Scheme 2. The reaction is generally conducted at about −78° C., in an organic solvent such as tetrahydrofuran. Compounds of formula (7) wherein $X^5$ is as defined for X in formula (I), other than hydrogen, can be prepared by treating compounds of formula (6) with a base such as sodium hydride, followed by treatment with a halide such as alkyl halide or one of formula $X^6$—$(CR^gR^h)_u$—$C(O)O(R^{10})$ wherein $X^6$ is halogen. The reaction can be conducted in an organic solvent such as N,N-dimethylformamide, and at a temperature of about 0° C. to about room temperature.

Reduction of the nitro group that is attached to $G^1$ in formula (1) or (3) can be accomplished by standard means such as, iron/acetic acid or iron/ammonium chloride to provide the corresponding —$NH_2$ compound.

Derivatization of the —$NH_2$ that is attached to $G^1$ in formula (1) or (3), to the corresponding carbamates, amides, ureas, secondary amines, sulfonamides, or sulfonyl ureas, can be can be achieved by employing methodologies or modifications thereof known in the art. For example, the amides can be obtained by carrying out a coupling reaction with appropriate carboxylic acids under standard coupling reaction conditions. Displacement of appropriate halides with the primary amino group that is attached to $G^1$, provides secondary amines of formula (1) or (3). Reaction of the primary amino group with a suitable haloformate in the presence of a base provides the corresponding carbamates. Treatment of the primary amines with an appropriate isocyanate provides the corresponding urea.

Scheme 2

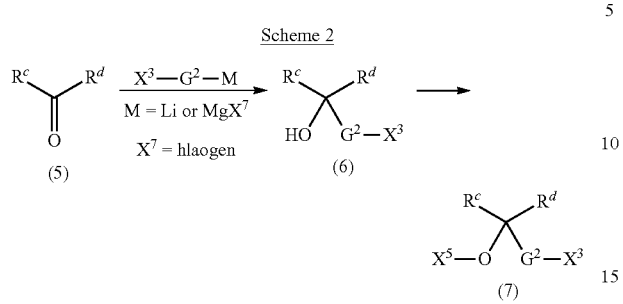

Compounds of formula (6) or (7) wherein $G^2$ is phenyl or monocyclic heteroaryl having one or more hydrogen atoms on the ring, can be halogenated using general procedures known by one skilled in the art. For example, iodides of formula (2) wherein $X^3$ is iodine, can be prepared by treating compounds of formula (6) with n-butyllithium at about −78° C., followed by dropwise addition of iodine solution.

Alternatively, compounds of formula (2) wherein $X^3$ is hydrogen, halogen, triflate, of tosylate, $G^3$ is formula (b), $L^1$ is O, and $R^c$ and $R^d$, together with the carbon atom to which they are attached is a cyclopentyl can be prepared by general procedures as shown in Scheme 3.

Scheme 3

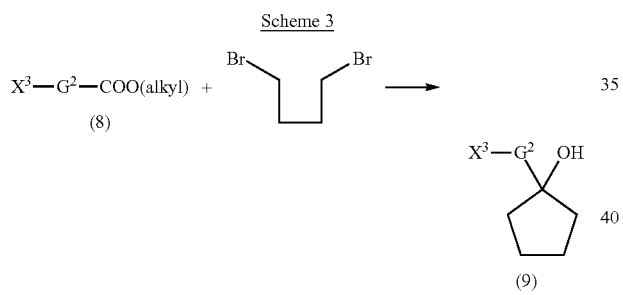

For example, esters of formula (8) when treated with 1,4-dibromobutane in the presence of magnesium and an organic solvent such as, tetrahydrofuran, at about 0° C., provide compounds of formula (9).

Intermediates of formula (2) wherein $X^3$ is hydrogen or halogen, and $G^3$ is formula (b) wherein $L^1$ is —$CH_2$— and X is —C(O)OH can be prepared as shown in Scheme 4.

Scheme 4

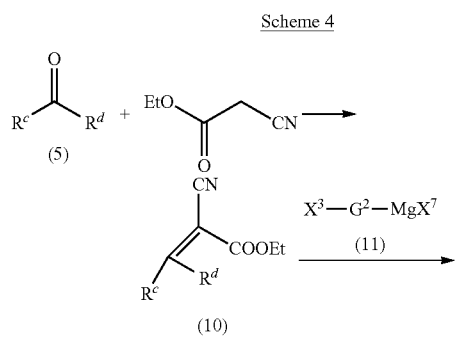

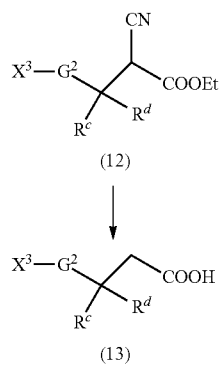

As shown in Scheme 4, ketones of formula (5) can be treated with ethyl cyanoacetate in the presence of hexamethyldisilazane to provide compounds of formula (10). Treatment of compounds of formula (10) with Grignard reagents of formula (11) wherein $X^3$ is hydrogen or halogen and $X^7$ is halogen, in the presence of a copper(I) salt such as, but not limited to Cu(I)I, Cu(I)Br, and Cu(I)CN, in a solvent such as tetrahydrofuran, at a temperature from about 0° C. to about room temperature provides compounds of formula (12). Compounds of formula (12) when treated with a base such as sodium or potassium hydroxide in a solvent such as ethylene glycol, at a temperature from about 100° C. to about 200° C., affords acids of formula (13).

Compounds of general formula (I) wherein G is of formula (b) and $L^1$ is N(H) or N(alkyl) can be prepared using general procedures as outlined in Scheme 5.

Scheme 5

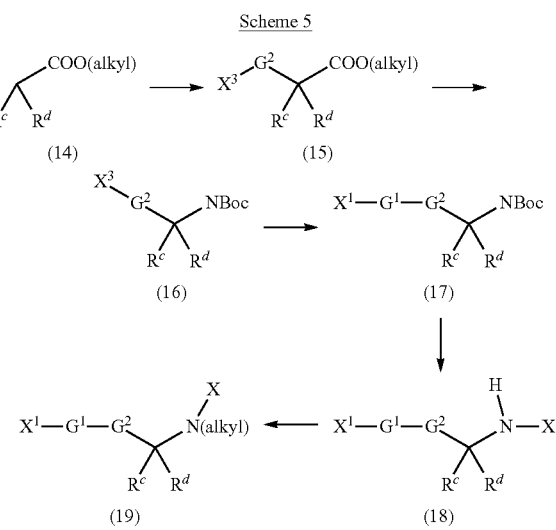

Esters of formula (14) can be converted to compounds of formula (15) by treatment with halides of formula $X^3$-$G^2$-$X^8$ wherein $X^8$ is halogen and $X^3$ is hydrogen or halogen, provided that $X^8$ is the more reactive halogen, in the presence of triphenylphosphine, a base such as lithium dicyclohexane amide, and a palladium catalyst such as bis(dibenzylideneacetone)palladium(0). Esters of formula (15) can be transformed to amines of formula (16) by (a) saponification with a base such as sodium hydroxide to provide the corresponding acid, (b) optionally converting the acid to acid chloride (c) converting the acid or the acid chloride to the corresponding azide by treating the acid with diphenylphosphoryl azide at elevated temperature or treating the acid chloride with sodium azide at ambient temperature, in the presence of a base, and (d) heating the acyl azide from step (c) with tert-butanol. Coupling of compounds of formula (16) with (1) using reaction conditions as described in Scheme 1 results in compounds of formula (17). Removal of the Boc group can be accomplished by treatment with an acid such as trifluoroacetic acid. The resulting primary amine can undergo reductive amination with an aldehyde of formula XCHO using reaction conditions known in the art to provide compounds of formula (18). For example, transformation can be carried out in the presence of a reducing agent such as sodium triacetoxyborohydride and an acid such as acetic acid, in a solvent such as tetrahydrofuran. The reaction can be carried out at about room temperature to about 50° C., optionally in the presence of molecular sieves, silica gel of under Dean-Stark conditions. Compounds of formula (19) can be obtained from (18) by treating with an appropriate aldehyde using the aforementioned reductive amination conditions.

Intermediates of formula (2) wherein $G^3$ is formula (a), wherein $R^5$ and $R^6$ are hydrogen, $W^1$ is —C($R^3$)($R^4$)— or —C($R^3$)($R^4$)—C($R^3$)($R^4$)—, $W^2$ is —C($R^7$)— or N, $R^7$ is —C(O)OH, and $W^4$ is —CH$_2$—, can be prepared using general procedures as illustrated in Scheme 6.

presence of a base such as sodium hydride, in a solvent such as N,N-dimethylformamide. Compounds of formula (21) wherein E is C(H)COOH can be methylated to compounds of formula (21) wherein E is C(H)COO(CH$_3$) by treatment with trimethylsilyl diazomethane. Selective reduction of (21) with a mild reducing agent such as sodium borohydride, followed by treatment with tosyl chloride in the presence of a base such as 4-dimethylaminopyridine results in Compounds of formula (22) wherein E is N(Boc) or C(H)COO(CH$_3$). Compounds of formula (22) wherein E is N(Boc) can be converted to compounds of formula (23) wherein E is N(H) by treatment of an acid such as trifluoroacetic acid. In the presence of a base such as potassium carbonate, sodium hydride or an amide base such as lithium diisopropyl amide, compounds of formula (22) wherein E is N(H) or C(H)COO(CH$_3$), undergo a ring closure to provide compounds of formula (23) wherein E is N or C—COO(CH$_3$). Saponification of the ester functional group can be carried out at different stages of the synthetic route, for example, after the ring closure, or after coupling of (23) with (1), or after the derivatization of the amine attached to $G^1$, by treatment with a base such as sodium hydroxide.

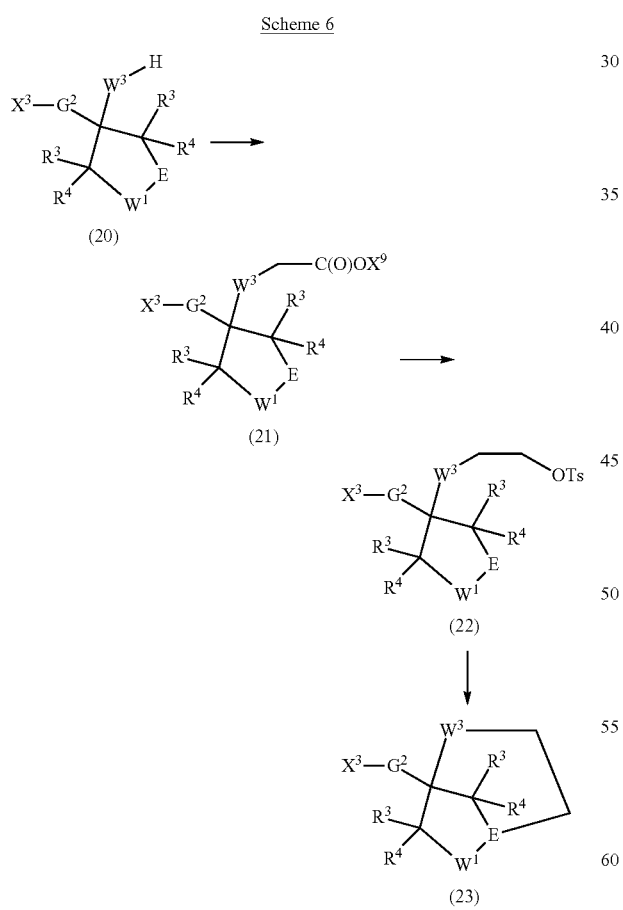

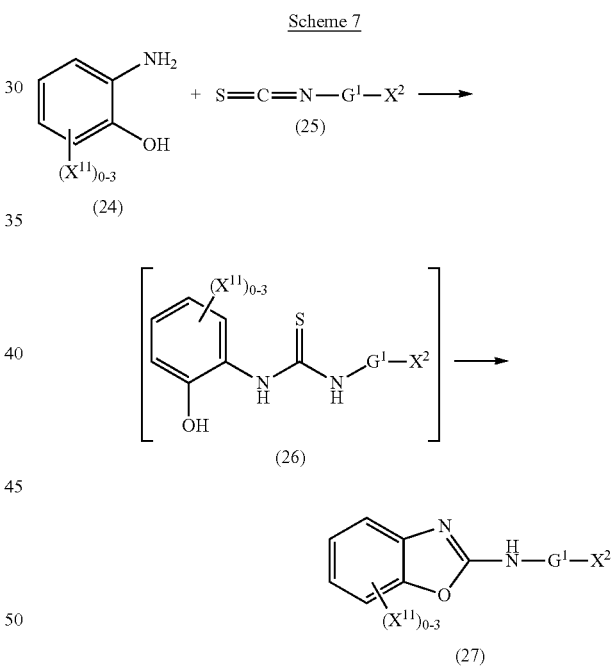

Compounds of formula (20) wherein E is N(Boc) or C(H)COOH can be transformed to compounds of formula (21) wherein $X^9$ is hydrogen or alkyl by reacting (20) with halides of formula $X^9$OC(O)CH$_2$X$^{10}$ wherein $X^{10}$ is halogen, in the Intermediates of formula (1) wherein $X^1$ is —N(H)Q and Q is unsubstituted or substituted benzoxazolyl, can be, prepared as shown in Scheme 7. Amino phenols of formula (24) wherein $X^{11}$ represents substituents of Q as defined in formula (I) can be treated with a thioisocyanate of formula (25) wherein $X^2$ is hydrogen or halogen to provide thiourea intermediates of formula (26). The reaction is generally conducted in an inert organic solvent such as tetrahydrofuran, at a temperature of about −10° C. to about 50° C., preferably at about room temperature. The thiourea intermediates, with or without isolation, when treated with lithium hydroxide/hydrogen peroxide provide benzoxazoles of formula (27).

Scheme 8

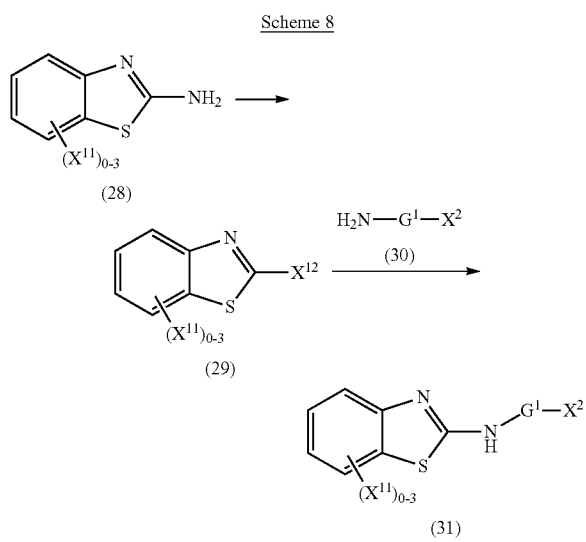

Intermediates of formula (1) wherein $X^1$ is —N(H)Q and Q is unsubstituted or substituted benzothiazolyl, can be prepared as shown in Scheme 8. Halides of formula (29) wherein $X^{12}$ is chlorine or bromine, and $X^{11}$ represents substituents of Q as defined in formula (I), can be prepared from commercially available 2-aminobenzothiazole of formula (28) by (a) treatment of (28) with tert-butyl nitrite and (b) displacement of the diazonium salt formed in step (a) with cuprous chloride or bromide. Displacement of the halide of (29) with an appropriate amine of formula (30) under analogous; reaction conditions known in the art provides compounds of formula (31).

Preparation of the boronic esters of formulae (27) and (31) wherein $X^2$ is formula (4) from the corresponding halides is accomplished by reaction with a boronic ester reagent such as pinnacol borane, in the presence of a base such as potassium acetate, a palladium catalyst such as [1,1'-bis(diphenylphosphino)ferrocene]dichloropalladium(II), and in a solvent such as dioxane, N,N-dimethylformamide, toluene, or mixtures thereof, at an elevated temperature.

It wall be appreciated that the synthetic schemes and specific examples as illustrated in the synthetic examples section are illustrative and are not to be read as limiting the scope of the invention as it is defined in the appended claims. All alternatives, modifications, and equivalents of the synthetic methods and specific examples are included within the scope of the claims.

Optimal reaction conditions and reaction times for each individual step can vary depending on the particular reactants employed and substituents present in the reactants used. Unless otherwise specified, solvents, temperatures and other reaction conditions can be readily selected by one of ordinary skill in the art. Specific procedures are provided in the Synthetic Examples section. Reactions can be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or can be prepared, by one skilled in the art from Commercially available materials using methods described in the chemical literature.

Routine experimentations, including appropriate manipulation of the reaction conditions, reagents and sequence of the synthetic route, protection of any chemical functionality that can not be compatible with the reaction conditions, and deprotection at suitable point in the reaction sequence of the method are included in the scope of the invention. Suitable protecting groups and the methods for protecting and deprotecting different substituents using such suitable protecting groups are well known to those skilled in the art; examples of which can be found in T. Greene and P. Wuts, Protecting Groups in Chemical Synthesis ($3^{rd}$ ed), John Wiley & Sons, NY (1999), which is incorporated herein by reference in its entirety. Synthesis of the compounds of the invention Can be accomplished by methods analogous to those described in the synthetic, schemes described hereinabove and in specific examples.

Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic/examples section.

When an optically active form of a compound of the invention is required, it can be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound of the invention is required, it can be obtained by carrying out one of the above procedures using a pure geometric isomer as a starting material, or by resolution of a mixture of the geometric isomers of the compound of intermediates using a standard procedure such as chromatographic separation.

Biological Data

Inhibition of DGAT-1

The identification of the compounds of the invention as DGAT-1 inhibitors was readily achieved using a high throughput screening FlashPlate assay. In this assay, recombinant human DGAT-1 containing an N-terminal $His_6$-epitope tag was produced in the baculovirus expression system. Insect cells (e.g., Sf9 or High Five) were infected for 24 to 72 hours and, collected by Centrifugation. Cell pellets were resuspended in homogenization buffer [250 mM sucrose, 10 mM tris-HCl (pH 7.4), 1 mM EDTA] and lysed using a homogenization apparatus, such as a Microfluidizer (single pass, 4° C.). Cell debris was removed by centrifugation at 10,000×g for 30 min, and microsomal membranes were collected by ultracentrifugation at 100,000×g for 30 min.

DGAT-1 activity was determined as follows: Assay buffer [20 mM HEPES (pH 7.5), 2 mM $MgCl_2$, 0.04% BSA] containing 50 μM of enzyme substrate (didecanoyl glycerol) and 7.5 μM radiolabeled acyl-CoA substrate.[1-$^{14}$C]decanoyl-CoA) was added to each well of a phospholipid FlashPlate (PerkinElmer Life Sciences). A small aliquot of membrane (1 μg/well) was added to start the reaction, which was allowed to proceed for 60 min. The reaction was terminated upon the addition of an equal volume (100 μL) of isopropanol. The plates were sealed, incubated overnight and counted the next morning on a TopCount Scintillation Plate Reader (PerkinElmer Life Science). DGAT-1 catalyzes the transfer of the radiolabel-led decanoyl group onto the sn-3 position of didecanoyl glycerol. The resultant radiolabeled tridecanoyl glycerol (tricaprin) preferentially binds to the hydrophobic coating on the phospholipid FlashPlate. The proximity of the radiolabeled product to the solid scintillant incorporated into the bottom of the FlashPlate induced fluor release from the scintillant, which was measured in the TopCount Plate Reader. Various concentrations (e.g. 0.0001 µM, 0.001 µM, 0.01 µM, 0.1 µM, 1.0 µM, 10.0 µM) of the representative compounds of the invention were added to individual wells prior to the addition of membranes. The potencies of DGAT-1 inhibition for the compounds of the present invention were determined by calculating the $IC_{50}$ values defined as the inhibitor concentration from the sigmoidal dose response curve at which the enzyme activity was inhibited 50%. Compounds of the present invention were effective in inhibiting DGAT-1 activity and thus are useful as therapeutic agents for treating conditions and diseases that are associated with DGAT-1 activity.

TABLE 1

DGAT-1 Inhibition of compounds of the present invention ($IC_{50}$ nM)

| | | | | | |
|---|---|---|---|---|---|
| 3 | 3 | 4 | 4 | 5 | 5 |
| 7 | 7 | 7 | 8 | 8 | 8 |
| 8 | 9 | 11 | 15 | 16 | 19 |
| 24 | 38 | 46 | 49 | 52 | 75 |
| 93 | 105 | 106 | 113 | 133 | 279 |
| 294 | 311 | 429 | 440 | 492 | 494 |
| 501 | 568 | 608 | 677 | 853 | 1030 |
| 1120 | 1160 | 1170 | 1270 | 1340 | 1790 |
| 1830 | 2160 | 3310 | 3510 | 4060 | 4160 |
| 4200 | 5530 | 3.5 | 8.5 | | |

Evaluation of Compound Efficacy on the Reduction of Chylomicron Excursion in DIO or CD1 Mice The purpose of this protocol was to determine the effect of acute administration of a compound on the chylomicron excursion induced by a corn oil bolus in either lean mice (CD1 mice, Jackson Laboratories) or mice made obese by spontaneous ad libitum consumption of a high-fat diet (Buhman, K. K. et al., *J Biol Chem.* 2002, 277, 25474-25479). Diet-induced obesity (DIO) in rodents mimics key aspects of human obesity and metabolic syndrome. DIO mice used in this study have been shown to be hyperinsulinemic and insulin resistant, hyperleptinemic and leptin resistant, and have marked visceral obesity (for review on DIO mice see Collins et al., Physiol. Behav. 81:243-248, 2004).

Representative compounds of the invention were typically dosed at 0.03 mg/kg, 0.3 mg/kg, 3 mg/kg, or 10 mg/kg p.o as a formulation in 1% Tween 80 in water one hour prior to the administration of corn oil bolus. One hour after the bolus was administered, plasma samples were taken and analyzed for triglycerides. The compounds were considered to be active if drug treatment resulted in >30% reduction in plasma triglycerides in drug treated animals (measured one hour after the administration of corn oil bolus) relative to vehicle-treated control animals. In this model, representative compounds produced significant reductions in plasma triglycerides, relative to vehicle-treated control animals.

Compounds of the present invention and the pharmaceutically acceptable salts are useful as therapeutic agents. Accordingly, an embodiment of this invention includes a method of treating the various conditions in a subject in need thereof (including mammals) which includes administering to the subject an amount of the compound of formula (I), (II), or (III), or a pharmaceutically acceptable salt, prodrug, or salt of a prodrug thereof, that is effective in treating the target condition, or a pharmaceutical composition including the same.

Another aspect of the present invention provides a method of treating, delay of prevention of various conditions in a patient (such as mammal, preferably human) that are mediated by DGAT-1, which includes administering to the patient a compound of formula (I), (II), or (III), or a pharmaceutically acceptable salt, prodrug, salt of a prodrug thereof, or a pharmaceutical composition including the same.

Another aspect of the present invention provides methods for the prevention, delay or treatment of obesity and inducing weight loss in an individual which includes administering to the individual a compound of the invention, or its pharmaceutically acceptable salt, prodrug, salt of a prodrug thereof, of a pharmaceutical composition including the same. Yet another aspect of the invention provides a method for preventing weight gain in an individual by administering at least one compound of the invention, or its pharmaceutically acceptable salt, prodrug, salt of a prodrug, or a combination thereof, in an amount that is sufficient to prevent weight gain.

The present invention also relates to the use of the compounds of this invention for the treatment of obesity-related diseases including associated dyslipidemia and other obesity- and overweight-related complications such as, for example, cholesterol gallstones, gallbladder disease, gout, cancer (e.g., colon, rectum, prostate, breast, ovary, endometrium, cervix, gallbladder, and bile duct), menstrual abnormalities, infertility, polycystic ovaries, osteoarthritis, and sleep apnea, as well as for a number of other pharmaceutical uses associated therewith, such as the regulation of appetite and food intake, dyslipidemia, hypertriglyceridemia, metabolic syndrome or Syndrome X, type 2 diabetes (non-insulin-dependent diabetes), atherosclerotic diseases such as heart failure, hyperlipidemia, hypercholesteremia, low HDL levels, hypertension, cardiovascular disease (including atherosclerosis, coronary heart disease, coronary artery disease, and hypertension), cerebrovascular disease such as stroke, and peripheral vessel disease. The compounds of this invention can also be useful for treating physiological disorders related to, for example, regulation of insulin sensitivity, inflammatory response, liver steatosis, elevated liver triacylglycerides, non-alcoholic fatty liver disease, non-alcoholic steatohepatitis, plasma triacylglycerides, HDL, LDL and Cholesterol levels and the like. Metabolic syndrome is characterized by a group of metabolic risk factors in one person. Such factors include, but are hot limited to, abdominal obesity, atherogenic dyslipidemia (blood fat disorders such as high triglycerides, low HDL Cholesterol and high LDL Cholesterol), elevated blood pressure, insulin resistance (or glucose intolerance), prothrombotic state (e.g. high fibrinogen or plasminogen activator inhibitor-1 in the blood), and proinflammatory state (e.g. elevated C-reactive protein in the blood). In one embodiment, the present invention provides methods of treating the above listed disorders wherein the methods include the step of administering to a subject in need thereof one or more of the compound of the invention, of pharmaceutically acceptable salt thereof, or a pharmaceutical composition including the same. The compounds of this invention, of pharmaceutical acceptable salts thereof, or pharmaceutical compositions including the same, are also useful in lowering plasma triglycerides level. Thus, in one embodiment, the present invention provides a method for lowering plasma triglycerides in a subject (including mammal) in need thereof, wherein the method includes the step of administering to the subject in need thereof one or more of the compound of invention, or pharmaceutically acceptable salt thereof, or a pharmaceutical composition including the same.

The term "treatment" or "treating" includes any process, action, application, therapy, or the like, wherein a subject, including human, is provided medical aid with the object of improving the subject's condition, directly or indirectly, or slowing the progression of a condition or disorder in the subject.

Compounds of the invention, or pharmaceutically acceptable salts, prodrugs, salts of prodrugs, or combination thereof, can be administered alone or in combination (i.e. co-administered) with one or more additional pharmaceutical agents. Combination therapy includes administration of a single pharmaceutical dosage formulation containing one or more of the compounds of invention, or pharmaceutically acceptable salts, prodrug, salts of prodrugs thereof, and one or more additional pharmaceutical agents, as well as administration of the compounds of invention, or pharmaceutically acceptable salts, prodrug, salts of prodrugs thereof, and each additional pharmaceutical agent, in its own separate pharmaceutical dosage formulation. For example, a compound of formula (I), (II), or (III), or a pharmaceutically acceptable salts, prodrugs, salts of prodrugs thereof, and one or more additional pharmaceutical agents, can be administered to the patient together, in a single oral dosage composition having a fixed ratio of each active ingredient, such as a tablet or capsule; or each agent can be administered in separate oral dosage formulations.

Where separate dosage formulations are used, compounds of the invention (or pharmaceutical salts, prodrugs, of salts of prodrugs thereof) and one or more additional pharmaceutical agents can be administered at essentially the same time (e.g., concurrently) or at separately staggered times (e.g., sequentially).

For example, the compounds of the invention (or pharmaceutical salts, prodrugs, or salts of prodrugs thereof) can be used in combination with one of more of the following pharmaceutical agents, including, but not limited to, anti-obesity drugs including β3 agonists such as CL-316,243; CB-1 antagonists and/or inverse agonists (for example, rimonabant); neuropeptide Y5 inhibitors; appetite suppressants, such as, for example, sibutramine (Meridia); MCHr1 antagonists and lipase inhibitors, such as, for example, orlistat (Xenical), and a drug compound that modulates digestion and/or metabolism such as drugs that modulate thermogenesis; lipolysis, gut motility, fat absorption, and satiety.

In addition, compounds of the invention (or pharmaceutical salts, prodrugs, or salts of prodrugs thereof) can be administered in combination with one or more of the following pharmaceutical agents including PPAR ligands (agonists, antagonists), insulin secretagogues (for example, sulfonylurea drugs and non-sulfonylurea secretagogues), α-glucosidase inhibitors, insulin sensitizers, hepatic glucose output lowering Compounds, and insulin and insulin derivatives. Such agents can be administered prior to, concurrently with, or following administration of the compounds of the invention. Insulin and insulin derivatives include both long and short acting forms and formulations of insulin. PPAR ligands can include agonists and/or antagonists of any of the PPAR receptors or combinations thereof. For example, PPAR ligands can include ligands of PPAR-α, PPAR-γ, PPAR-δ or any combination of two or three of the receptors of PPAR. PPAR ligands include, for example, rosiglitazone, troglitazone, and pioglitazone. Sulfonylurea drugs include, for example, glyburide, glimepiride, chlorpropamide, tolbutamide, and glipizide, α-glucosidase inhibitors include acarbose, miglitol, and voglibose. Insulin sensitizers include PPAR-γ agonists such as the glitazones (e.g., troglitazone, pioglitazone, englitazone, MCC-555, rosiglitazone, and the like) and other thiazolidinedione and non-thiazolidinedione compounds; biguanides such as metformin and phenformin; protein tyrosine phosphatase-1B (PP-1B) inhibitors; dipeptidyl peptidase IV (DPP-IV) inhibitors (for example, sitagliptin), and 11beta-HSD inhibitors. Hepatic glucose output lowering compounds include glucagon antagonists and metformin, such as Glucophage and Glucophage XR. Insulin secretogogues include sulfonylurea and non-sulfonylurea drugs. GLP-1, GIP, PACAP, secretin, and derivatives thereof; nateglinide, meglitinide, repaglinide, glibenclamide, glimepiride, chlorpropamide, glipizide. GLP-1 includes derivatives of GLP-1 with longer half-lives than native GLP-1, such as, for example, fatty-acid derivatized GLP-1 and exendin.

Compounds of the invention (or pharmaceutical salts, prodrugs, or salts of prodrugs thereof) can also be used in methods of the invention in combination with one, or more pharmaceutical agents including, but are not limited to, HMG-CoA reductase inhibitors, nicotinic acid (for example, Niaspan), fatty acid lowering compounds (e.g., acipimox); lipid lowering drugs (e.g., stanol esters, sterol glycosides such as tiqueside, and azetidinones such as ezetimibe), ACAT inhibitors (such as avasimibe), bile acid sequestrants, bile acid reuptake inhibitors, microsomal triacylglycerides transport inhibitors, and fibric acid derivatives. HMG-CoA reductase inhibitors include, for example, statin such as lovastatin, simvastatin, pravastatin, fluvastatin, atorvastatin, rivastatin, itavastatin, cerivastatin, and ZD-4522. Fibric acid derivatives include, for example, clofibrate, fenofibrate, bezafibrate, ciprofibrate, beclofibrate, etofibrate, and gemfibrozil. Sequestrants include, for example, cholestyramine, colestipol, and dialkylaminoalkyl derivatives of across-linked dextran.

Compounds of the invention (or pharmaceutical salts, prodrugs, of salts of prodrugs thereof) can also be used in combination with anti-hypertensive drugs, such as, for example, β-blockers and ACE inhibitors. Examples of additional anti-hypertensive agents for use in combination with the compounds of the present invention include calcium channel blockers (L-type and T-type; e.g., diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors, ACE inhibitors (e.g., captopril, zofenopril, fosinopril, enalapril, ceranopril, cilazopril, delapril, pehtbpril, quinapril, ramipril, lisinopril), AT-1 receptor antagonists (e.g., losartan, irbesartan, valsartan), ET receptor antagonists (e.g., sitaxsentan, atrsentan, neutral endopeptidase (NEP) inhibitors, vasopeptidase inhibitors (dual NEP-ACE inhibitors) (e.g., omapatrilat and gemopatrilat), and nitrates.

The compounds of this invention can also be co-administered with an incretin mimetic such as, but not limited to, exenatide.

The compounds of this invention (or pharmaceutical salts, prodrugs, or salts of prodrugs thereof) can be utilized to achieve the desired pharmacological effect by administration to a subject in need thereof in an appropriately formulated pharmaceutical composition; A subject, for example, can be a mammal, including human, in need of treatment for a particular condition or disease. Therefore the present invention includes pharmaceutical compositions which are included of a therapeutically effective amount of a compound (or pharmaceutical salts, prodrugs, or salts of prodrugs thereof) identified by the methods described herein, in combination with a pharmaceutically acceptable carrier. The compounds identified by the methods described herein can be administered with a pharmaceutically acceptable carrier using any effective conventional dosage unit forms, for example, immediate and timed release preparations, orally, parenterally, topically, or the like.

The pharmaceutical compositions can be formulated for oral administration in solid or liquid form, for parenteral injection or for rectal administration.

The term "pharmaceutically acceptable carrier" as used herein, means a non-toxic, solid, semi-solid or liquid filler, diluent, encapsulating material, or formulation auxiliary of any type. Examples of therapeutically suitable excipients include sugars; cellulose and derivatives thereof; oils; glycols; solutions; buffering, coloring, releasing, coating, sweetening, flavoring, and perfuming agents; and the like. These therapeutic compositions can be administered parenterally, intracisternally, orally, rectally, intraveneously, or intraperitoneally.

Liquid dosage forms for oral administration of the present compounds include formulations of the same as emulsions, microemulsions, solutions, suspensions, syrups, and elixirs. In addition to the compounds, the liquid dosage forms can contain diluents and/or solubilizing or emulsifying agents. Besides inert diluents, the oral compositions can include wetting, emulsifying, sweetening, flavoring, and perfuming agents.

Injectable preparations of the present compounds include sterile, injectable, aqueous and oleaginous solutions, suspensions or emulsions, any of which can be optionally formulated with parenterally suitable diluents, dispersing, wetting, or suspending agents. These injectable preparations can be sterilized by filtration through a bacterial-retaining filter or formulated with sterilizing agents that dissolve or disperse in the injectable media.

Inhibition of DGAT-1 by the compounds of the present invention can be delayed by using a liquid suspension of crystalline or amorphous material with poor water solubility. The rate of absorption of the compounds depends upon their rate; of dissolution, which, in turn, depends on their crystallinity. Delayed absorption of a parenterally administered compound can be accomplished by dissolving or suspending the compound in oil. Injectable depot forms of the compounds can also be prepared by microencapsulating the same in biodegradable polymers. Depending upon the ratio of compound to polymer and the nature of the polymer employed, the rate of release can be controlled. Depot injectable formulations are also prepared by entrapping the compounds in liposomes of microemulsions that are compatible with body tissues.

Solid dosage forms for oral administration of the present compounds include capsules, tablets, pills, powders, and granules. In such forms, the compound is mixed with at least one inert, therapeutically suitable excipient such as a carrier, filler, extender, disintegrating agent, solution retarding agent, wetting agent absorbent, or lubricant. With capsules, tablets, and pills, the excipient can also contain buffering agents. Suppositories for rectal administration can be prepared by mixing the compounds with a suitable non-irritating excipient that is solid at ordinary temperature but fluid in the rectum.

The present compounds can be micro-encapsulated with one or more of the excipients discussed previously. The solid dosage forms of tablets, dragees, capsules, pills, and granules can be prepared with coatings and shells such as enteric and release-controlling. In these forms, the compounds can be mixed with at least one inert diluent and can optionally include tableting lubricants and aids. Capsules can also optionally contain opacifying agents that delay release of the Compounds in a desired part of the intestinal tract.

Transdermal patches have the added advantage of providing controlled delivery of the present compounds to the body. Such dosage forms are prepared by dissolving or dispensing the compounds in the proper medium. Absorption enhancers Can also be used to increase the flux of the compounds across the skin, and the rate of absorption can be controlled by providing a rate controlling membrane or by dispersing the compounds in a polymer matrix or gel.

The compounds of the invention can be used in the form of pharmaceutically acceptable salts, esters, or amides derived from inorganic of organic acids. The term "pharmaceutically acceptable salts, esters and amides," as used herein, include salts, zwitterions, esters and amides of compounds of disclosed herein which are, within the scope of sound medical judgment, suitable for use in contact, with the tissues of humans and lower animals without undue toxicity, irritation, allergic response, and the like, are commensurate with a reasonable benefit/risk ratio, and are effective for their intended use.

Pharmaceutically acceptable salts are well-known in the art. The salts can be prepared during the final isolation and purification of the compounds or separately by reacting an amino group of the compounds with a suitable acid. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, malate, maleate, methanesulfonate, napthlyenesulfonate, nicotinate, oxalate, pamoate, pectinate, persulfate 3-phenylpropionate, picrate, oxalate, pivalate, propionate, succinate, tartrate, trichloroacetic, trifluoracetic, glufamate, para-toluenesulfonate, undecanoate, hydrochloric, hydrobromic, sulfuric, phosphoric, and the like. The amino groups of the compounds can also be quaternized with alkyl chlorides, bromides, and iodides such as methyl, ethyl, propyl, isopropyl, butyl, lauryl, myristyl, stearyl, and the like.

Basic addition salts can be prepared during the final isolation and purification of the present compounds by reaction of a carboxyl group with a suitable base such as the hydroxide, carbonate, or bicarbonate of a metal cation such as lithium, sodium; potassium, calcium, magnesium, or aluminum, or an organic primary, secondary, or tertiary amine. Quaternary amine salts derived from methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine, ethylenediamine, ethanolamine, diethanolamine, piperidine, piperazine, and the like, are contemplated as being within the scope of the present invention.

The term "pharmaceutically acceptable ester," as used herein, refers to esters of compounds of the invention which hydrolyze in vivo and include those that break down readily in the human body to leave the parent compound or a salt thereof. Examples of pharmaceutically acceptable, non-toxic esters of the invention include $C_{1-6}$ alkyl esters and $C_{5-7}$ cycloalkyl esters, although $C_{1-4}$ alkyl esters are preferred. Esters of the compounds of the invention can be prepared according to conventional methods. Pharmaceutically acceptable esters can be appended onto hydroxy groups by reaction of the compound that contains the hydroxy group with acid and an alkylcarboxylic acid such as acetic acid, or with acid and an arylcarboxylic acid such as benzoic acid. In the case of compounds containing carboxylic acid groups, the pharmaceutically acceptable esters are prepared from Compounds containing the carboxylic acid groups by reaction of the compound with base, such as triethylamine and an alkyl halide, alkyl triflate, for example with methyl iodide, benzyl iodide, cyclopentyl iodide. They also can be prepared by reaction of the compound with an acid such as hydrochloric acid and an alkylcarboxylic acid such as acetic acid, or with acid and an arylcarboxylic acid such as benzoic acid.

The term "pharmaceutically acceptable amide," as used herein, refers to non-toxic amides of the invention derived from ammonia, primary $C_{1-6}$ alkyl amines and secondary $C_{1-6}$ dialkyl amines. In the case of secondary amines, the amine can also be in the form of a 5- or 6-membered heterocycle containing one nitrogen atom. Amides derived from ammonia, $C_{1-3}$ alkyl primary amides and $C_{1-2}$ dialkyl secondary amides are preferred. Amides of the Compounds of the invention, can be prepared according to conventional methods. Pharmaceutically acceptable amides can be prepared from compounds containing primary or secondary amine groups by reaction of the compound that contains the amino group with an alkyl anhydride, aryl anhydride; acyl halide, or aroyl halide. In the case of compounds containing carboxylic acid groups, the pharmaceutically acceptable esters are prepared from compounds containing the carboxylic acid groups by reaction of the compound with base such as triethylamine, a dehydrating agent such as dicyclohexyl carbodiimide of carbonyl diimidazole, and an alkyl amine, dialkylamine, for example with methylamine, diethylamine, piperidine. They also can be prepared by reaction of the compound with an acid such as sulfuric acid and an alkylcarboxylic acid such as acetic acid, or with, acid and an arylcarboxylic acid such as benzoic acid under dehydrating conditions as with molecular sieves added. The composition can contain a Compound of the invention in the form of a pharmaceutically acceptable prodrug.

The term "pharmaceutically acceptable prodrug" or "prodrug" as used herein, represents those prodrugs of the compounds of the invention which are, within the scope of sound medical judgment, suitable for use in contact with the tissues of humans and lower animals without undue toxicity, irritation, allergic response, and the like, commensurate with a reasonable benefit/risk ratio, and effective for their intended use. Prodrugs of the invention can be rapidly transformed in vivo to a parent compound of the invention, for example, by hydrolysis in blood. A thorough discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987).

Disorders that can be treated or prevented in a patient by administering to the patient, a therapeutically effective amount of compound (or pharmaceutical salts, prodrugs, or salts of prodrugs thereof) of the present invention in such an amount and for such time as is necessary to achieve the desired result. The term "therapeutically effective amount," refers to a sufficient amount of a compound of the invention to effectively ameliorate disorders by inhibiting DGAT-1 at a reasonable benefit/risk ratio applicable to any medical treatment. The specific therapeutically effective dose level for any particular patient can depend upon a variety of factors including the disorder being treated and the severity of the disorder; the activity of the compound employed; the specific composition employed; the age, body weight, general health, sex, and diet of the patient; the time of administration, route of administration, rate of excretion; the duration of the treatment; and drugs used in combination or coincidental therapy.

The total daily dose of the compounds of the present invention necessary to inhibit the action of DGAT-1 in single or divided doses can be in amounts, for example, from about 0.01 to 50 mg/kg body weight. In a more preferred range, compounds of the present invention inhibit the action of DGAT-1 in a single or divided doses from about 0.05 to 25 mg/kg body weight. Single dose compositions can contain such amounts or submultiple doses thereof of the compounds of the present invention to make up the daily dose. In general, treatment regimens include administration to a patient in need of such treatment from about 1 mg to about 1000 mg of the compounds per day in single or multiple doses.

The compounds identified by the methods described herein can be administered as the sole pharmaceutical agent or in combination with one or more other pharmaceutical agents where the combination causes no unacceptable adverse effects. For example, the compounds of this invention can be combined with anti-obesity, or with known antidiabetic or other indication agents, and the like. Thus, the presents invention also includes pharmaceutical compositions which are made of a therapeutically effective amount of a compound identified by the methods described herein, or a pharmaceutically acceptable salt thereof, a pharmaceutically acceptable carrier, and one or more pharmaceutical agents as disclosed hereinabove.

The compounds and processes of the present invention are better understood by reference to the following examples, which are intended as an illustration of and hot a limitation upon the scope of the invention. Further, all citations herein are incorporated by reference.

EXAMPLES

Example 1

N-[2-fluoro-5-(trifluoromethyl)phenyl]-N'-{4-[2-(4-hydroxytetrahydro-2H-pyran-4-yl)-1,3-thiazol-5-yl]phenyl}urea Example 1A 1-(2-fluoro-5-(trifluoromethyl)phenyl)-3-(4-(4,4,5,5-tetramethyl-1,3,2-dioxaborolan-2-yl)phenyl)urea To an ambient solution of 4-(4,4,5,5-tetramethyl-1,3,2-dioxaborolan-2-yl)aniline (2.0 g, 9.13 mmol) in tetrahydrofuran (30 mL) was added 2-fluoro-5-trifluoromethylphenyl isocyanate (1.32 mL, 9.13 mmol). After 1 h, the mixture was concentrated under reduced pressure to afford the title compound as a white solid. MS (ESI) m/z 425 [M+H]$^+$.

Example 1B 4-(5-iodothiazol-2-yl)tetrahydro-2H-pyran-4-ol

To a cold (−78° C.) solution of thiazole (2.0 mL, 28.2 mmol) in tetrahydrofuran (140 mL) was added n-butyllithium (11.4 mL, 28.2 mmol, 2.48 M in hexane) dropwise. After 15 minutes, dihydro-2H-pyran-4(3H)-one (2.59 mL, 28.2 mmol) was added in a single portion. After 30 minutes, n-butyllithium (11.4 mL, 28.2 mmol, 2.48 M in hexane) was added dropwise. The reaction was allowed to stir for an additional 20 minutes, after which a solution of iodine (7.24 g, 28.2 mmol) in tetrahydrofuran (15 mL) was added dropwise. The reaction was then quenched by the addition of saturated aqueous $Na_2S_2O_3$ and ethyl acetate (100 mL) and allowed to warm to ambient temperature. The layers were separated, and the aqueous was extracted with additional ethyl acetate (2×100 mL). The combined organics were dried with anhydrous $Na_2SO_4$, filtered, and concentrated to give a dark solid. Trituration of the residue with dichloromethane gave the title compound as a beije solid. MS (ESI) m/z 312 [M+H]$^+$.

Example 1C

N-[2-fluoro-5-(trifluoromethyl)phenyl]-N'-{4-[2-(4-hydroxytetrahydro-2H-pyran-4-yl)-1,3-thiazol-5-yl]phenyl}urea A solution of Example 1B (183 mg, 0.59 mmol), Example 1A (250 mg, 0.59 mmol), CsF (269 mg, 1.77 mmol), and tetrakis(triphenylphosphine)palladium(0) (69 mg, 0.06 mmol) in a solvent mixture of dimethoxyethane (1 mL) and methanol (1 mL) was heated to 90° C. for 16 h. The reaction was cooled to ambient temperature and diluted with ethyl acetate (2 mL) and H$_2$O (1 mL). The layers were separated, and the organic was dried with anhydrous Na$_2$SO$_4$, filtered, and concentrated to give a solid. The residue was purified via RP-HPLC (preparative reversed-phase high pressure liquid chromatography) using a Zofbax SB-C18 7M 21.2×250 mm column with UV detection analyzed at 220 and 254 nM (preparative method: water with 0.1% trifluoroacetic acid and CH$_3$CN with 0.1% trifluoroacetic acid gradient 5-95% CH$_3$CN over 30 minutes at 15 mL/min.) to provide the title compound as a white solid. $^1$H NMR (300 MHz, DMSO-d$_6$) δ ppm 1.69 (br d, J=12.2 Hz, 2 H), 2.07-2.17 (m, 2 H), 3.70-3.76 (m, 4 H), 6.16 (s, 1 H), 7.37-7.42 (m, 1 H), 7.51-7.54 (m, 3 H), 7.59 (m, 2H), 8.00 (s, 1 H), 8.61 (m, 1 H), 8.94 (m, 1 H), 9.35 (s, 1 H); MS (ESI) m/z 482 [M+H]$^+$.

Example 2

N-{4-[2-(1-ethyl-4-hydroxypiperidin-4-yl)-1,3-thiazol-5-yl]phenyl}-N'-[2-fluoro-5-(trifluoromethyl)phenyl]urea

Example 2A 1-ethyl-4-(5-iodothiazol-2-yl)piperidin-4-ol

Example 2A was prepared according to the procedure described for Example 1A, substituting 1-ethylpiperidin-4-one for dihydro-2H-pyran-4(3H)-one, MS (ESI) m/z 338 [M+H]$^+$.

Example 2B

N-{4-[2-(1-ethyl-4-hydroxypiperidin-4-yl)-1,3-thiazol-5-yl]phenyl}-N'-[2-fluoro-5-(trifluoromethyl)phenyl]urea The trifluoroacetic acid salt of the title compound was prepared according to the procedure described for Example 1C, substituting Example 2A for Example 1B. $^1$H NMR (300 MHz, DMSO-d$_6$) δ ppm 1.06 (t, J=7.1 Hz, 3 H), 1.78 (br d, J=11.5 Hz, 2 H), 2.12 (br t, J=10.9 Hz, 2 H), 2.69-2.87 (m, 2 H), 3.30-3.44 (m, 4 H), 6.00 (s, 1 H), 7.38-7.43 (m, 1 H), 7.48-7.54 (m, 3 H), 7.58 (m, 2 H), 7.99 (s, 1 H), 8.61 (m, 1 H), 8.93 (m, 1 H), 9.32 (s, 1 H); MS (ESI) m/z 509 [M+H]$^+$.

Example 3

4-(5-{4-[(5,7-dimethyl-1,3-benzoxazol-2-yl)amino]-3-fluorophenyl}-1,3-thiazol-2-yl)tetrahydro-2H-pyran-4-ol

Example 3A

N-(4-bromo-2-fluorophenyl)-5,7-dimethylbenzo[d]oxazol-2-amine

An ambient solution of 2-amino-4,6-dimethylphenol (0.85 g, 6.2 mmol) and 2-fluoro-4-bromophenyl isothiocyanate (1.44 g, 6.20 mmol) in tetrahydrofuran (20 mL) was stirred for 16 h. The reaction was cooled (0° C.), and LiOH.H$_2$O (0.521 g, 12.41 mmol) was added, followed by the dropwise addition of 30% H$_2$O$_2$ (3.41 mL, 31.0 mmol) over 15 minutes. The reaction was warmed to room temperature and stirred for 16 h. The reaction was then quenched by the addition of 20% aqueous sodium sulfite; solution (50 mL) and ethyl acetate (75 mL). The layers were separated, and the aqueous was extracted with additional ethyl acetate (2×75 mL). The combined organics were dried with anhydrous Na$_2$SO$_4$, filtered and concentrated under reduced pressure. The residue was purified by chromatography on SiO$_2$ gel, eluting with 25% ethyl acetate in hexane, to give the title compound. MS (ESI) m/z 335 [M+H]$^+$.

Example 3B

N-(2-fluoro-4-(4,4,5,5-tetramethyl-1,3,2-dioxaborolan-2-yl)phenyl)-5,7-dimethylbenzo[d]oxazol-2-amine A mixture of Example 3A (2.34 g, 6.98 mmol), 4,4,4',4',5,5,5',5'-octamethyl-2,2'-bi(1,3,2-dioxaborolane) (2.13 g, 8.38 mmol), potassium acetate (2.06 g, 21.0 mmol) and [1,1'-bis(diphenylphosphino)ferrocene]dichloropalladium(II) complex with CH$_2$Cl$_2$ (0.171 g, 0.209 mmol) in dioxane (30 mL) was heated to 95° C. for 24 h. The reaction was cooled to room temperature and diluted; with brine (100 mL) and ethyl acetate (100 mL). The layers, were separated, and the aqueous was extracted with additional ethyl acetate (2×75 mL). The combined organics were dried with anhydrous Na$_2$SO$_4$, filtered and concentrated under reduced pressure. The residue was purified by chromatography on SiO$_2$ gel, eluting with 25% ethyl acetate in hexane, to give the title compound. MS (ESI) m/z 383 [M+H]$^+$.

Example 3C 4-(5-{4-[(5,7-dimethyl-1,3-benzoxazol-2-yl)amino]-3-fluorophenyl}-1,3-thiazol-2-yl)tetrahydro-2H-pyran-4-ol A solution of Example 3B (0.062 g, 0.161 mmol), Example 1B (0.050 g, 0.161 mmol), CsF (0.073 g, 0.482 mmol), and tetrakis(triphenylphosphine)palladium(0) (0.019 g, 0.0161 mmol) in a solvent mixture of dimethoxyethane/methanol (1/1, 1 mL) was heated to 90° C. for 1.6 h. The reaction was cooled to room temperature and partitioned between H$_2$O (2 mL) and ethyl acetate (2 mL). The layers were separated, and the aqueous was extracted with additional ethyl acetate (2×2 mL). The combined organics were dried with anhydrous Na$_2$SO$_4$, filtered, and concentrated under reduced pressure. The residue was purified by RP-HPLC (preparative reversed-phase high pressure liquid chromatography) using a Zorbax SB-C18 7M 21.2×250 mm column with UV detection analyzed at 220 and 254 nM (preparative method: water with 0.1% trifluoroacetic acid and $CH_3CN$ with 0.1% trifluoroacetic acid gradient 5-95% $CH_3CN$ over 30 minutes at 15 mL/min.) to provide the title compound as a white solid. $^1H$ NMR (300 MHz, DMSO-$d_6$) δ ppm 1.69 (d, J=12.6 Hz, 2 H), 2.08-2.20 (m, 2 H), 2.34 (s, 3 H), 2.39 (s, 3 H), 3.64-3.87 (m, 4 H), 6.20 (s, 1 H), 6.80 (s, 1 H), 7.08 (s, 1 H), 7.51 (m, 1 H), 7.65 (m, 1 H), 8.10 (s, 1 H), 834 (m, 1 H), 10.50 (s, 1 H); MS (ESI) m/z 440[M+H]$^+$.

Example 4

4-(5-{4-[(7-methyl-1,3-benzoxazol-2-yl)amino]phenyl}-1,3-thiazol-2-yl)tetrahydro-2H-pyran-4-ol Example 4A N-(4-bromophenyl)-7-methylbenzo[d]oxazol-2-amine An ambient solution of 2-amino-6-methylphenol (0.74 g, 6.0 mmol) and 4-bromophenyl isothiocyanate (1.28 g, 6.0 mmol) in tetrahydrofuran (20 mL) was stirred for 16 h. The reaction was cooled (0° C.), and LiOH.$H_2O$ (0.521 g, 12.41 mmol) was added, followed by the dropwise addition of 30% $H_2O_2$ (3.41 mL, 31.0 mmol) over 15 minutes. The reaction was warmed to room temperature and stirred for 16 h. The reaction was then quenched by the addition of 20% aqueous sodium sulfite solution (50 mL) and ethyl acetate (75 mL). The layers were separated, and the aqueous was extracted with additional ethyl acetate (2×75 mL). The combined organics were dried with anhydrous $Na_2SO_4$, filtered and concentrated under reduced pressure. The residue was purified by chromatography on $SiO_2$ gel, eluting with 25% ethyl acetate in hexane, to give the title compound. MS (ESI) m/z 303 [M+H]$^+$.

Example 4B 7-methyl-N-(4-(4,4,5,5-tetramethyl-1,3,2-dioxaborolan-2-yl)phenyl)benzo[d]oxazol-2-amine Example 4B was prepared according to the procedure described for Example 3B, substituting Example 4A for Example 3A. MS (ESI) m/z 351 [M+H]$^+$.

Example 4C 4-(5-{4-[(7-methyl-1,3-benzoxazol-2-yl)amino]phenyl}-1,3-thiazol-2-yl)tetrahydro-2H-pyran-4-ol Example 4C was prepared according to the procedure described for Example 3C, substituting Example 4C for Example 3B. $^1H$ NMR (300 MHz, DMSO-$d_6$) δ ppm 1.69 (d, J=12.2 Hz, 2 H), 2.04-2.20 (m, 2 H), 2.44 (s, 3 H), 3.66-3.81 (m, 4 H), 6.14 (s, 1 H), 6.98 (m, 1 H), 7.13 (m, 1 H), 7.30 (m, 1 H), 7.60-7.71 (m, 2 H), 7.76-7.87 (m, 2 H), 7.99 (s, 1 H), 10.83 (s, 1 H); MS (ESI) m/z 408 [M+H]$^+$.

Example 5

4-(5-{2-chloro-4-[(7-chloro-1,3-benzoxazol-2-yl)amino]phenyl}-1,3-thiazol-2-yl)tetrahydro-2H-pyran-4-ol Example 5A N-(4-bromo-3-chlorophenyl)-7-chlorobenzo[d]oxazol-2-amine An ambient solution of 2-amino-6-chlorophenol (0.86 g, 6.0 mmol) and 3-chloro-4-bromophenyl isothiocyanate (1.49 g, 6.0 mmol) in tetrahydrofuran (20 mL) was stirred for 16 h. The reaction was cooled (0° C.), and LiOH.$H_2O$ (0.521 g, 12.41 mmol) was added, followed by the drop wise addition of 30% $H_2O_2$ (3.41 mL, 31.0 mmol) over 15 minutes. The reaction was warmed to room temperature and stirred for 16 h. The reaction was then quenched by the addition of 20% aqueous sodium sulfite solution (50 mL) and ethyl acetate (75 mL). The layers were separated, and the aqueous was extracted with additional ethyl acetate (2×75 mL). The combined organics were dried with anhydrous $Na_2SO_4$, filtered and concentrated under reduced pressure. The residue was purified by chromatography on $SiO_2$ gel, eluting with 25% ethyl acetate in hexane, to give the title compound. MS (ESI) m/z 359 [M+H]$^+$.

Example 5B 7-chloro-N-(3-chloro-4-(4,4,5,5-tetramethyl-1,3,2-dioxaborolan-2-yl)phenyl)benzo[d]oxazol-2-amine Example 5B was prepared according to the procedure described for compound 3B, substituting Example 5A for Example 3A. MS (ESI) m/z 405 [M+H]$^+$.

Example 5C 4-(5-{2-chloro-4-[(7-chloro-1,3-benzoxazol-2-yl)amino]phenyl}-1,3-thiazol-2-yl)tetrahydro-2H-pyran-4-ol Example 5C was prepared according to the procedure described for Example 3C, substituting Example 5B for Example 3B. $^1H$ NMR (300 MHz, DMSO-$d_6$) δ ppm 1.70 (d, J=12.2 Hz, 2 H), 2.04-2.21 (m, 2 H), 3.65-3.84 (m, 4 H), 6.23 (s, 1 H), 7.24-7.29 (m, 2 H), 7.51 (m, 1 H), 7.67-7.72 (m, 2 H), 7.95 (s, 1 H), 8.09 (s, 1 H), 11.36 (s, 1 H); MS (ESI) m/z 462 [M+H]$^+$.

Example 6

4-(5-{4-[(7-chloro-1,3-benzoxazol-2-yl)amino]-2-methylphenyl}-1,3-thiazol-2-yl)tetrahydro-2H-pyran-4-ol Example 6A N-(4-bromo-3-methylphenyl)-7-chlorobenzo[d]oxazol-2-amine Example 6A was prepared according to the procedure described for Example 5A, substituting 3-methyl-4-bromophenyl isothiocyanate for 3-chloro-4-bromophenyl isothiocyanate. MS (ESI) m/z 339 [M+H]$^+$.

Example 6B 7-chloro-N-(3-methyl-4-(4,4,5,5-tetramethyl-1,3,2-dioxaborolan-2-yl)phenyl)benzo[d]oxazol-2-amine Example 6B was prepared according to the procedure described for Example 3B, substituting Example 6A for Example 3A. MS (ESI) m/z 385 [M+H]$^+$.

Example 6C

4-(5-{4-[(7-chloro-1,3-benzoxazol-2-yl)amino]-2-methylphenyl}-1,3-thiazol-2-yl)tetrahydro-2H-pyran-4-ol Example 6C was prepared according to the procedure described for Example 3C, substituting Example 6B for Example 3B. $^1$H NMR (300 MHz, DMSO-d$_6$) δ ppm 1.71 (d, J=12.2 Hz, 2 H), 2.06-2.22 (m, 2 H), 2.40 (s, 3 H), 3.65-3.84 (m, 4 H), 6.17 (s, 1 H), 7.16-7.33 (m, 2 H), 7.37-7.53 (m, 2 H), 7.62-7.76 (m, 3 H), 11.09 (s, 1 H); MS (ESI) m/z 519 [M+H]$^+$.

Example 7

N-[2-fluoro-5-(trifluoromethyl)phenyl]-N'-{6-[2-(4-hydroxytetrahydro-2H-pyran-4-yl)-1,3-thiazol-5-yl]pyridin-3-yl}urea

Example 7A

4-(5-(5-nitropyridin-2-yl)thiazol-2-yl)tetrahydro-2H-pyran-4-ol

To a cold (−78° C.) solution of thiazole (0.382 mL, 5.41 mmol) in tetrahydrofuran (30 mL) was added n-butyllithium (3.38 mL, 5.41 mmol, 1.6 M in hexane) dropwise. After 15 minutes, dihydro-2H-pyran-4(3H)-one (0.49 mL, 5.41 mmol) was added in a single portion. After 30 minutes, n-butyllithium (3.38 mL, 5.41 mmol, 1.6 M in hexane) was added dropwise. The reaction was allowed to stir for an additional 20 minutes, after which ZnCl$_2$ (10.8 mL, 10.8 mmol, 1 M in diethyl ether) was added. The cooling bath was removed, and the reaction warmed to room temperature. 2-Bromo-5-nitropyridine (1.10 g, 5.41 mmol) and tetrakis(triphenylphosphine)palladium(0) (0.623 g, 0.54 mmol) were added, and the reaction heated to 55° C. for 16 h. The reaction was cooled to ambient temperature and quenched by the addition of saturated NH$_4$Cl (30 mL) and ethyl acetate (30 mL). The layers were separated, and the aqueous was extracted with additional ethyl acetate (2×30 mL). The combined organics were dried with anhydrous Na$_2$SO$_4$, filtered, and concentrated under reduced pressure. The residue was purified by chromatography on SiO$_2$, eluting with a gradient of 10% ethyl acetate in hexane to 35% ethyl acetate in hexane; to give the title product. MS (ESI) m/z 308 [M+H]$^+$.

Example 7B

4-(5-(5-aminopyridin-2-yl)thiazol-2-yl)tetrahydro-2H-pyran-4-ol

To a solution of Example 7A (0.106 g, 0.344 mmol) in a solvent mixture of methanol (2 mL) and acetic acid (2 mL) was added Zn powder (0.067 g, 1.03 mmol). The reaction was heated to 50° C. for 5 h, and was then cooled to room temperature. The reaction was quenched by the addition of saturated aqueous NaHCO$_3$ (5 mL) and ethyl acetate (5 mL). The layers were separated, and the aqueous was extracted with additional ethyl acetate (2×5 mL). The combined organics were dried with anhydrous Na$_2$SO$_4$, filtered, and concentrated under reduced pressure to yield the title compound which was used without further purification. MS (ESI) m/z 278 [M+H]$^+$.

Example 7C

N-[2-fluoro-5-(trifluoromethyl)phenyl]-N'-{6-[2-(4-hydroxytetrahydro-2H-pyran-4-yl)-1,3-thiazol-5-yl]pyridin-3-yl}urea To a solution of Example 7B (0.042 mg, 0.151 mmol) in tetrahydrofuran (1 mL) was added 2-fluoro-5-trifluoromethylphenyl isocyanate (0.022 mL, 0.151 mmol). After 1 h, the mixture was concentrated under reduced pressure. The residue was purified by RP-HPLC (preparative reversed-phase high pressure liquid chromatography) using a Zorbax SB-C18 7M 21.2×250 mm column with UV detection analyzed at 220 and 254 nM (preparative method: water with 0.1% trifluoroacetic acid and CH$_3$CN with 0.1% trifluoroacetic acid gradient 5-95% CH$_3$CN over 30 minutes at 15 mL/min) to provide the title compound as a white solid. $^1$H NMR (300 MHz, DMSO-d$_6$) δ ppm 1.68 (br d, J=12.9 Hz, 2 H), 2.07-2.17 (m, 2 H), 3.68-3.80 (m, 4 H), 6.15 (s, 1 H), 7.40-7.45 (m, 1 H), 7.52 (m, 1 H), 7.89 (m, 1 H), 8.08 (m, 1 H), 8.25 (s, 1 H), 8.55-8.60 (m, 2 H), 9.10 (s, 1 H), 9.40 (s, 1 H); MS (ESI) m/z 483 [M+H]$^+$.

Example 8

N-{4-[2-(1-ethyl-4-hydroxypiperidin-4-yl)-1,3-thiazol-5-yl]-2-fluorophenyl}-N'-[2-fluoro-5-(trifluoromethyl)phenyl]urea

Example 8A tert-butyl 4-(2-(1-ethyl-4-hydroxypiperidin-4-yl)thiazol-5-yl)-2-fluorophenylcarbamate A solution of Example 2A (0.33 g, 0.98 mmol), 4-(tert-butoxycarbonylamino)-3-fluorophenylboronic acid (0.25 g, 0.98 mmol), CsF (0.46 g, 3.0 mmol), and tetrakis(triphenylphosphine)palladium(0) (0.12 g, 0.098 mmol) in a solvent mixture of dimethoxyethane (2 mL) and methanol (1 mL) was heated to 90° C. for 16 h. The reaction was cooled to ambient temperature and diluted with ethyl acetate (5 mL) and H$_2$O (5 mL). The layers were separated, and the organic was washed with 10% aqueous HCl (3×15 mL). 2N NaOH was added to the combined acidic aqueous layers until pH=8. The aqueous layer was extracted with ethyl acetate (3×15 mL). The extracts were then dried with anhydrous Na$_2$SO$_4$, filtered, and concentrated under reduced pressure to give the title product as a solid. MS (ESI) m/z 422 [M+H]$^+$.

Example 8B

4-(5-(4-amino-3-fluorophenyl)thiazol-2-yl)-1-ethylpiperidin-4-ol

To an ambient solution of Example 8A (0.20 g, 0.48 mmol) in dichloromethane (2 mL) was added trifluoroacetic acid (2 mL). The reaction was stirred for 2 h, and was then concentrated under reduced pressure. The residue was partitioned between saturated aqueous NaHCO$_3$ (5 mL) and ethyl acetate (5 mL). The layers were separated, and the aqueous was extracted with additional ethyl acetate (2×5 mL). The combined organics were dried with anhydrous Na$_2$SO$_4$, filtered, and concentrated under reduced pressure to yield the title compound, which was used without further purification. MS (ESI) m/z 322 [M+H]$^+$.

Example 8C

N-{4-[2-(1-ethyl-4-hydroxypiperidin-4-yl)-1,3-thiazol-5-yl]-2-fluorophenyl}-N'-[2-fluoro-5-(trifluoromethyl)phenyl]urea To an ambient solution of Example 8B (0.02 g, 0.062 mmol) in tetrahydrofuran (1 mL) was added 2-fluoro-5-trifluoromethylphenylioscyanate (0.010 g, 0.065 mmol). After 1 h, the mixture was concentrated under reduced pressure. The residue was purified by RP-HPLC (preparative reversed-phase high pressure liquid chromatography) using a Zofbax SB-C18 7M 21.2×250 mm column with UV detection analyzed at 220 and 254 nM (preparative method: water with 0.1% trifluoroacetic acid and $CH_3CN$ with 0.1% trifluoroacetic acid gradient 5-95% $CH_3CN$ over 30 minutes at 15 mL/min). The fractions containing the desired product were diluted with saturated aqueous $NaHCO_3$ and extracted with ethyl acetate. The organic layer was dried with anhydrous $Na_2SO_4$, filtered and concentrated under reduced pressure to give the title compound as a white solid. $^1$H NMR (300 MHz, DMSO-$d_6$) δ ppm 1.01 (t, J=7.1 Hz, 3 H), 1.73 (br d, J=11.9 Hz, 2 H), 2.08 (dt, J=11.9 and 3.7 Hz, 2 H), 2.25-2.37 (m, 4 H), 2.64-2.73 (m, 2 H), 6.15 (s, 1 H), 7.33-7.52 (m, 3 H), 7.61 (m, 1 H), 8.05 (s, 1 H), 8.24 (m, 1 H), 8.64 (m, 1 H), 8.90 (s, 1 H), 9.34 (s, 1 H); MS (ESI) m/z 527 [M+H]$^+$.

Example 9

N-(2,5-difluorophenyl)-N'-{4-[2-(1-ethyl-4-hydroxypiperidin-4-yl)-1,3-thiazol-5-yl]-2-fluorophenyl}urea The title compound was prepared according to the procedure described for Example 8C, substituting 2,5-difluorophenylisocyanate for 2-fluoro-5-trifluoromethylphenylisocyanate. $^1$H NMR (300 MHz, DMSO-$d_6$) δ ppm 1.03 (t, J=7.1 Hz, 3 H), 1.73 (br d, J=11.9 Hz, 2 H), 2.08 (dt, J=11.9 and 3.7 Hz, 2 H), 2.33-2.44 (m, 4 H), 2.71-2.76 (m, 2 H), 6.85 (s, 1 H), 7.21-7.29 (m, 1 H), 7.36-7.44 (m, 2 H), 7.63-7.69 (m, 1 H), 8.02-8.07 (m, 1 H), 8.10 (s, 1 H), 8.22 (m, 1 H), 8.90 (s, 1 H), 9.30 (s, 1 H); MS (ESI) m/z 477 [M+H]$^+$.

Example 10

N-[2-fluoro-5-(trifluoromethyl)phenyl]-N'-{6-[2-(1-hydroxycyclopentyl)-1,3-thiazol-5-yl]pyridin-3-yl}urea

Example 10A 1-(5-Iodo-thiazol-2-yl)-cyclopentanol

Example 10A was prepared according to the procedure described for Example 1B, substituting cyclopentanone for dihydro-2H-pyran-4(3H)-one. MS (ESI) m/z 296 [M+H]$^+$.

Example 10B 1-(5-(5-nitropyridin-2-yl)thiazol-2-yl)cyclopentanol

Example 10B was prepared according to the procedure described for Example 7A, substituting cyclopentanone for dihydro-2H-pyran-4(3H)-one. MS (ESI) m/z 292 [M+H]$^+$.

Example 10C 1-(5-(5-aminopyridin-2-yl)thiazol-2-yl)cyclopentanol

Example 10C was prepared according to the procedure described for Example 7B, substituting Example 10B for Example 7A. MS (ESI) m/z 262 [M+H]$^+$.

Example 10D

N-[2-fluoro-5-(trifluoromethyl)phenyl]-N'-{6-[2-(1-hydroxycyclopentyl)-1,3-thiazol-5-yl]pyridin-3-yl}urea Example 10D was prepared according to the procedure described for Example 7C, substituting Example 10C for Example 7B. $^1$H NMR (300 MHz, DMSO-$d_6$) δ ppm 1.74-1.92 (m, 6 H), 2.04-2.12 (m, 2 H), 6.50 (s, 1 H), 7.40-7.42 (m, 1 H), 7.4 (m, 1 H), 7.87 (m, 1 H), 8.07 (m, 1 H), 8.21 (s, 1 H), 8.56-8.58 (m, 2 H), 8.93 (s, 1 H), 9.44 (s, 1 H); MS (ESI) m/z 467 [M+H]$^+$.

Example 11 phenyl 4-[2-(4-hydroxytetrahydro-2H-pyran-4-yl)-1,3-thiazol-5-yl]phehylcarbamate

Example 11A 4-(5-(4-nitrophenyl)thiazol-2-yl)tetrahydro-2H-pyran-4-ol

A solution of Example 1B (1.0 g, 3.2 mmol), 4-nitrophenylboronic acid (0.75 g, 4.5 mmol), KF (0.56 g, 9.6 mmol), and bis(triphenylphosphine)palladium(II) dichloride (0.22 g, 0.32 mmol) in a solvent mixture of dimethoxyethane (5 mL) and methanol (5 mL) was heated to 90° C. for 16 h. The reaction was cooled to room temperature and partitioned between ethyl acetate (10 mL) and $H_2O$ (10 mL). The layers were separated, and the aqueous was extracted with additional ethyl acetate (2×10 mL). The combined organics were dried with anhydrous $Na_2SO_4$, filtered, and concentrated under reduced pressure. The residue was purified by chromatography on $SiO_2$ gel, eluting with 50% ethyl acetate in hexane; to give the title compound. MS (ESI) m/z 307 [M+H]$^+$.

Example 11B 4-(5-(4-aminophenyl)thiazol-2-yl)tetrahydro-2H-pyran-4-ol

Example 11B was prepared according to the procedure described for 7B, substituting Example 11A for Example; 7A. MS (ESI) m/z 277 [M+H]$^+$.

Example 11C phenyl 4-[2-(4-hydroxytetrahydro-2H-pyran-4-yl)-1,3-thiazol-5-yl]phenylcarbamate To an ambient solution of Example 11B (0.040 g, 0.145 mmol) and triethylamine (0.020 mL, 0.145 mmol) in tetrahydrofuran (1 mL) was added phenylchloroformate (0.016 mL, 0.145 mmol). After 16 h, the reaction was concentrated under reduced pressure. The residue was purified by chromatography on $SiO_2$ gel, eluting with ethyl acetate, to yield the title compound. $^1$H NMR (300 MHz, DMSO-$d_6$) δ ppm 1.57-1.77 (m, 2 H), 2.02-2.20 (m, 2 H), 3.64-3.81 (m, 4 H), 6.12-6.18 (m, 1 H), 7.12-7.19 (m, 1 H); 7.22-7.28 (m, 2 H), 7.40-7.48 (m, 2 H), 7.54-7.65 (m, 4 H), 8.00 (s, 1 H); MS (ESI) m/z 397 [M+H]$^+$.

Example 12

N-{4-[2-(4-hydroxytetrahydro-2H-pyran-4-yl)-1,3-thiazol-5-yl]phenyl}piperidine-1-carboxamide To an ambient solution of Example 11B (0.040 g, 0.145 mmol) and triethylamine (0.020 mL, 0.145 mmol) in tetrahydrofuran (1 mL) was added piperidine-1-carbonyl chloride (0.018 mL, 0.145 mmol). After 16 h, the reaction was concentrated under reduced pressure. The residue was purified by chromatography on SiO$_2$ gel, eluting with ethyl acetate, to yield the title compound. $^1$H NMR (300 MHz, DMSO-$d_6$) δ ppm 1.43-1.62 (m, 6 H), 1.68 (d, J=12.2 Hz, 2 H), 2.02-2.21 (m, 2 H), 3.39-3.46 (m, 4 H), 3.64-3.80 (m, 4 H), 6.12 (s, 1 H), 7.45-7.56 (m, 4 H), 7.94 (s, 1 H), 8.56 (s, 1 H); MS (ESI) m/z 388 [M+H]$^+$.

Example 13 tert-butyl 3-(5-{4-[({[2-fluoro-5-(trifluoromethyl)phenyl]amino}carbonyl)amino]phenyl}-1,3-thiazol-2-yl)-3-hydroxypyrrolidine-1-carboxylate Example 13A tert-buty 3-hydroxy-3-(5-iodothiazol-2-yl)pyrrolidine 1-carboxylate To a cold (−78° C.) solution of thiazole (0.382 mL, 5.41 mmol) in tetrahydrofuran (30 mL) was added n-butyllithium (3.38 mL, 5.41 mmol, 1.6 M in hexane) dropwise. After 15 minutes, N-boc-3-pyrrolidinone (0.49 mL, 5.41 mmol) was added in a single portion. After 30 minutes, lithium diisopropylamide (5.41 mL, 5.41 mmol, 1.0 M in tetrahydrofuran) was added dropwise. The reaction was allowed to stir for an additional 30 minutes, after which a solution of I$_2$ (1.37 g, 5.4 mmol) in tetrahydrofuran (10 mL) was added dropwise. After 10 minutes, the reaction was then quenched by the addition of saturated aqueous Na$_2$S$_2$O$_3$ (100 mL) and ethyl acetate (100 mL) and allowed to warm to ambient temperature. The layers were separated, and the aqueous was extracted with additional ethyl acetate (2×100 mL). The combined organics were dried with anhydrous Na$_2$SO$_4$, filtered, and concentrated to give a dark solid. The residue was purified by chromatography on SiO$_2$ gel, eluting with 50% ethyl acetate in hexanes, to give the title product as a solid. MS (ESI) m/z 397 [M+H]$^+$.

Example 13B tert-butyl 3-(5-{4-[({[2-fluoro-5-(trifluoromethyl)phenyl]amino}carbonyl)amino]phenyl}-1,3-thiazol-2-yl)-3-hydroxypyrrolidine-1-carboxylate Example 13B was prepared according to the procedure described for Example 1C, substituting Example 13A for Example 1B. $^1$H NMR (500 MHz, DMSO-$d_6$) δ ppm 1.33-1.49 (m, 9 H), 2.05-2.17 (m, 1 H), 2.28-2.42 (m, 1 H), 3.40-3.53 (m, 1 H), 3.52-3.61 (m, 2 H), 3.62-3.71 (m, 1 H), 6.54 (s, 1 H), 7.34-7.65 (m, 6 H), 8.04 (s, 1 H), 8.56-8.66 (m, 1 H), 8.93 (m, 1 H), 9.28-9.40 (m, 1 H); MS (ESI) m/z 567 [M+H]$^+$.

Example 14

N-[2-fluoro-5-(trifluoromethyl)phenyl]-N'-{4-[2-(3-hydroxypyrrolidin-3-yl)-1,3-thiazol-5-yl]phenyl}urea To an ambient solution of Example 13B (0.30 g, 0.53 mmol) in dichloromethane (2 mL) was added trifluoroacetic acid (2 mL). After 1 h, the solution was concentrated under reduced, pressure. The residue was partitioned between saturated aqueous NaHCO$_3$ (5 mL) and ethyl acetate (5 mL). The layers were separated, and the aqueous was extracted with additional ethyl acetate (2×5 mL). The combined organics were dried with anhydrous Na$_2$SO$_4$, filtered, and concentrated under reduced pressure to yield the title compound. $^1$H NMR (500 MHz, DMSO-$d_6$) δ ppm 1.97-2.11 (m, 1 H), 2.23-2.32 (m, 1 H), 2.91-3.08 (m, 2 H), 3.07-3.19 (m, 2 H), 4.06-4.17 (m, 1 H), 6.17 (s, 1 H), 7.35-7.70 (m, 6 H), 7.99 (s, 1 H), 8.56-8.67 (m, 1 H), 8.95 (s, 1 H), 9.37 (s, 1 H); MS (ESI) m/z 467 [M+H]$^+$.

Example 15

N-[2-fluoro-5-(trifluoromethyl)phenyl]-N'-{4-[2-(3-hydroxy-1-methylpyrrolidin-3-yl)-1,3-thiazol-5-yl]phenyl}urea To an ambient solution of Example 14 (0.050 g, 0.107 mmol) in methanol containing 1% v/v acetic acid 1 mL) was added formaldehyde (0.012 mL, 0.161 mmol, 37 wt % in H$_2$O) and MP-CNBH$_3$ (0.054 g, 0.161 mmol, 3.0 mmol/g). The reaction was heated to 50° C. and shaken for 16 h. The reaction was then filtered and concentrated under reduced pressure. The residue was purified by RP-HPLC (preparative reversed-phase high pressure liquid chromatography) using a Zorbax SB-C18 7M 21.2×250 mm column with UV detection analyzed at 220 and 254 nM (preparative method: water with 0.1% trifluoroacetic acid and CH$_3$CN with 0.1% trifluoroacetic acid gradient 5-95% CH$_3$CN over 30 minutes at 15 mL/min). The fractions containing the desired product were diluted with saturated aqueous NaHCO$_3$ and extracted with ethyl acetate. The organic layer was dried with anhydrous Na$_2$SO$_4$, filtered and concentrated under reduced pressure to give the title compound as a white solid. $^1$H NMR (500 MHz, DMSO-$d_6$) δ ppm 2.01-2.13 (m, 1 H), 2.25-2.33 (m, 3 H), 2.35-2.46 (m, 1 H), 2.51-2.58 (m, 1 H), 2.73-2.94 (m, 3 H), 6.22-6.31 (m, 1 H), 7.37-7.44 (m, 1 H), 7.47-7.56 (m, 3 H), 7.56-7.62 (m, 2 H), 7.98 (s, 1 H), 8.62 (m, 1 H), 8.92 (m, 1 H), 9.32 (s, 1 H); MS (ESI) m/z 481 [M+H]$^+$.

Example 16

N-{4-[2-(1-ethyl-3-hydroxypyrrolidin-3-yl)-1,3-thiazol-5-yl]phenyl}-N'-[2-fluoro-5-(trifluoromethyl)phenyl]urea The title Compound was prepared according to the procedure described for Example 15, substituting acetaldehyde for formaldehyde. $^1$H NMR (300 MHz, DMSO-$d_6$) δ ppm 1.03 (t, J=7.29 Hz, 3 H), 2.00-2.12 (m, 1 H), 2.34-2.43 (m, 1 H), 2.53-2.63 (m, 1 H), 2.83-2.96 (m, 3 H), 4.09 (m, 2 H), 6.24 (s, 1 H), 7.33-7.70 (m, 6 H), 7.98 (s, 1 H), 8.61 (m, 1 H), 8.92 (m, 1 H), 9.32 (s, 1 H); MS (ESI) m/z 495 [M+H]$^+$.

Example 17

N-[2-fluoro-5-(trifluoromethyl)phenyl]-N'-{4-[2-(1-hydroxycyclopentyl)-1,3-thiazol-5-yl]phenyl}urea Example 17 was prepared according to the procedure described for 1C, substituting Example 10A for Example 1B. $^1$H NMR (500 MHz, DMSO-$d_6$) δ ppm 1.69-1.95 (m, 6 H), 2.01-2.16 (m, 2 H), 5.91 (s, 1 H), 7.36-7.43 (m, 1 H), 7.47-7.55 (m, 3 H), 7.55-7.61 (m, 2 H), 7.96 (s, 1 H), 8.62 (m, 1 H), 8.92 (m, 1 H), 9.32 (s, 1 H); MS (ESI) m/z 466 [M+H]$^+$.

Example 18

N-{4-[2-(1-hydroxycyclopentyl)-1,3-thiazol-5-yl]phenyl}-N'-[3-(trifluoromethyl)phenyl]urea

Example 18A

1-[4-(4,4,5,5-Tetramethyl-[1,3,2]dioxaborolan-2-yl)-phenyl]-3-(3-trifluoromethyl-phenyl)-urea Example 18A was prepared according to the procedure described for 1A, substituting 3-trifluoromethylphenyl isocyanate for 2-fluoro-5-trifluoromethylphenyl isocyanate. MS (ESI) m/z 407 [M+H]$^+$.

Example 18B

N-{4-[2-(1-hydroxycyclopentyl)-1,3-thiazol-5-yl]phenyl}-N'-[3-(trifluoromethyl)phenyl]urea Example 18B was prepared according to the procedure described for 1C, substituting Example 10A for Example 1B, and substituting Example 18A for Example 1A. $^1$H NMR (500 MHz, DMSO-$d_6$) δ ppm 1.70-1.96 (m, 6 H), 2.01-2.17 (m, 2 H), 5.80 (s, 1 H), 7.32 (m, 1 H), 7.46-7.65 (m, 6 H), 7.95 (s, 1 H), 8.02 (s, 1 H), 8.96 (s, 1 H), 9.05-9.16 (m, 1 H); MS (ESI) m/z 448 [M+H]$^+$.

Example 19

N-[2-fluoro-5-(trifluoromethyl)phenyl]-N'-{4-[2-(1-hydroxycyclobutyl)-1,3-thiazol-5-yl]phenyl}urea

Example 19A 1-(5-Iodo-thiazol-2-yl)cyclobutanol

Example 19A was prepared according to the procedure described for Example 1B, substituting cyclobutanone for dihydro-2H-pyran-4(3H)-one, MS (ESI) m/z 282 [M+H]$^+$.

Example 19B

N-[2-fluoro-5-(trifluoromethyl)phenyl]-N'-{4-[2-(1-hydroxycyclobutyl)-1,3-thiazol-5-yl]phenyl}urea Example 19B was prepared according to the procedure described for 1C, substituting Example 19A for Example 1B. $^1$H NMR (500 MHz, DMSO-$d_6$) δ ppm 1.77-1.99 (m, 2 H), 2.25-2.39 (m, 2 H), 2.51-2.59 (m, 2 H), 6.49 (s, 1 H), 7.36-7.44 (m, 1 H), 7.47-7.55 (m, 3 H), 7.56-7.62 (m, 2 H), 8.00 (s, 1 H), 8.62 (m, 1 H), 8.92 (m, 1 H), 9.32 (s, 1 H); MS (ESI) m/z 452 [M+H]$^+$.

Example 20

N-{4-[2-(1-hydroxycyclobutyl)-1,3-thiazol-5-yl]phenyl}-N'-[3-(trifluoromethyl)phenyl]urea Example 20 was prepared according to the procedure described for 1C, substituting Example 19A for Example 1B, and substituting Example 18A for Example 1A. $^1$H NMR (500 MHz, DMSO-$d_6$) δ ppm 1.78-1.97 (m, 2 H), 2.26-2.39 (m, 2 H), 2.50-2.58 (m, 2 H), 6.49 (s, 1 H), 7.32 (m, 1 H), 7.45-7.64 (m, 6 H), 7.95-8.07 (m, 2 H), 8.96 (s, 2 H), 9.08 (s, 2 H); MS (ESI) m/z 434 [M+H]$^+$.

Example 21

(±)-Cis-3-hydroxy-3-{4'-[({[3-(trifluoromethyl)phenyl]amino}carbonyl)amino]-1,1'-biphenyl-4-yl}cyclopentanecarboxylic acid

Example 21A (±)-Cis-(1S,3S)-3-(4-Bromo-phenyl)-3-hydroxy-cyclopentanecarboxylic acid To a cold (−78 °C.) solution of 1,4-dibromobenzene (1.0 g, 4.23 mmol) was added n-butyllithium (1.69 mL, 4.23 mmol, 2.5 M in hexane). After 30 minutes, (±)-3-oxo-cyclopentanecarboxylic acid (0.271 g, 2.12 mmol) was added as a solution in tetrahydrofuran (20 mL). The reaction was stirred for 30 minutes and then quenched by the addition of saturated aqueous NH$_4$Cl (50 mL) and ethyl acetate (50 mL). The layers were separated, and the aqueous was extracted with additional ethyl acetate (2×50 mL). The combined organic layers were dried with anhydrous Na$_2$SO$_4$, filtered and concentrated under reduced pressure. The residue was purified by chromatography on SiO$_2$ gel, eluting with ethyl acetate, to give the title compound. MS (ESI) m/z 287 [M+H]$^+$.

Example 21B (±)-Cis-3-hydroxy-3-{4'-[({[3-(trifluoromethyl)phenyl]amino}carbonyl)amino]-1,1'-biphenyl-4-yl}cyclopentanecarboxylic acid A mixture of Example 21A (0.041 g, 0.154 mmol), Example 18A (0.050 g, 0.154 mmol), Na$_2$CO$_3$ (0.049 g, 0.46 mmol), and tetrakis(triphenylphosphine)palladium(0) (0.017 g, 0.015 mmol) in a toluene/dimethoxyethane/ethanol/H$_2$O (10:3:2:1, 1 mL) solvent mixture was heated to 90 PC for 16 h. The reaction was cooled to room temperature and partitioned between 10% HCl (5 mL) and ethyl acetate (5 mL). The layers were, separated, and the aqueous was extracted with additional ethyl acetate (2×5 mL). The combined organic layers were dried with anhydrous Na$_2$SO$_4$, filtered and concentrated under reduced pressure. The residue was purified by RP-HPLC (preparative reversed-phase high pressure liquid chromatography) using a Zorbax SB-C18 7M 21.2×250 mm column with UV detection analyzed at 220 and 254 nM (preparative method: water with 0.1% trifluoroacetic acid and CH$_3$CN with 0.1% trifluoroacetic acid gradient 5-95% CH$_3$CN over 30 minutes at 15 mL/min) to provide the title compound as a white solid. $^1$H NMR (500 MHz, DMSO-$d_6$) δ ppm 1.86-2.03 (m, 3 H), 2.14-2.26 (m, 3 H), 2.92-3.05 (m, 1 H), 4.97 (s, 1 H), 7.32 (m, 1 H), 7.47-7.66 (m, 10 H), 8.03 (s, 1 H), 8.89 (s, 1 H), 9.07 (s, 1 H), 12.0 (s, 1 H); MS (ESI) m/z 484 [M+H]$^+$.

Example 22

N-[2-fluoro-5-(trifluoromethyl)phenyl]-N'-{4-[2-(1-methoxycyclopentyl)-1,3-thiazol-5-yl]phenyl}urea

Example 22A

5-Iodo-2-(1-methoxy-cyclopentyl)-thiazole

To a suspension of NaH (0.176 g, 4.41 mmol, 60 wt % in mineral oil) in N,N-dimethylformamide (10 mL) was added Example 10A (1.0 g, 3.39 mmol). After 0.5 h, iodomethane (0.317 mL, 5.09 mmol) was added, and the reaction was stirred for 16 h. The reaction was partitioned between $H_2O$ (10 mL) and ethyl acetate (10 mL). The layers were separated, and the aqueous was extracted with additional ethyl acetate (2×10 mL). The combined organic layers were dried with anhydrous $Na_2SO_4$, filtered and concentrated under reduced pressure. The residue was purified by chromatography on $SiO_2$ gel, eluting with 5% ethyl acetate in hexane, to give the title compound. MS (ESI) m/z 310 $[M+H]^+$.

Example 22B

N-[2-fluoro-5-(trifluoromethyl)phenyl]-N'-{4-[2-(1-methoxycyclopenyl)-1,3-thiazol-5-yl]phenyl}urea Example 22B was prepared according to the procedure described for Example 1C, substituting Example 22A for Example 1B. $^1$H NMR (300 MHz, DMSO-$d_6$) δ ppm 1.68-1.81 (m, 4 H), 2.03-2.16 (m, 4 H), 3.11-3.15 (m, 3 H), 7.35-7.44 (m, 1 H), 7.46-7.64 (m, 5 H), 8.00 (s, 1 H), 8.61 (m, 1 H), 8.93 (m, 1 H), 9.36 (s, 1 H); MS (ESI) m/z 553 $[M+H]^+$.

Example 23

{[1-(5-{4-[({[2-fluoro-5-(trifluoromethyl)phenyl]amino}carbonyl)amino]phenyl}-1,3-thiazol-2-yl)cyclopentyl]oxy}acetic acid

Example 23A

[1-(5-Iodo-thiazol-2-yl)-cyclopentyloxy]acetic acid ethyl ester

Example 23A was prepared according to the procedure described for Example 22A, substituting bromoethylacetate for iodomethane. MS (ESI) m/z 382 $[M+H]^+$.

Example 23B

{[1-(5-{4-[({[2-fluoro-5-(trifluoromethyl)phenyl]amino}carbonyl)amino]phenyl}-1,3-thiazol-2-yl)cyclopentyl]oxy}acetic acid A solution of Example 23A (0.187 g, 0.491 mmol), Example 1A (0.208 g mL, 0.491 mmol), CsF (0.223 g, 1.47 mmol), and tetrakis(triphenylphosphine)palladium(0) (0.057 g, 0.049 mmol) in a solvent mixture of dimethoxyethane (1 mL) and methanol (1 mL) was heated to 90° C. for 16 h. The reaction was cooled to room temperature and diluted with $H_2O$ (5 mL). The solid was filtered, washed with diethyl ether, and air-dried to give the intermediate ester. The ester was dissolved in methanol (15 mL) and 2N NaOH (2 mL) and stirred for 16 h. The methanol was removed under reduced pressure, and the aqueous was washed with diethyl ether (20 mL). The aqueous was acidified to pH 1 with 10% HCl. The solid was filtered, washed with $CH_3CN$, and air-dried to give the title compound. $^1$H NMR (300 MHz, DMSO-$d_6$) δ ppm 1.66-1.91 (m, 4 H), 2.07-2.17 (m, 4 H), 3.91 (s, 2 H), 7.34-7.66 (m, 6 H), 8.02 (s, 1 H), 8.61 (m, 1 H), 9.02 (m, 1 H), 9.54 (s, 1 H), 10.45 (s, 1 H); MS (ESI) m/z 524 $[M+H]^+$.

Example 24

{[1-(5-{4-[(bicyclo[4.2.0]octa-1,3,5-trien-7-ylcarbonyl)amino]phenyl}-1,3-thiazol-2-yl)cyclobutyl]oxy}acetic acid

Example 24A

Ethyl 2-(1-(5-iodothiazol-2-yl)cyclobutoxy)acetate

To an ambient suspension of NaH (0.390 g, 9.75 mmol) in N,N-dimethylformamide (40 mL) was added Example 19A (2.74 g, 9.75 mmol) as a solution in N,N-dimethylformamide (10 mL). After 1 h, ethyl 2-bromoacetate (1.08 mL, 9.75 mmol) was added in a single portion. After 16 h, the reaction was quenched by the addition of $H_2O$ (50 mL) and ethyl acetate (50 mL). The layers were separated, and the aqueous was extracted with additional ethyl acetate (2×50 mL). The combined organics were dried with anhydrous $Na_2SO_4$, filtered, and concentrated under reduced pressure. The residue was purified by chromatography on $SiO_2$ gel, eluting with a gradient of hexane to 5% ethyl acetate in hexane, to give the title compound. MS (ESI) m/z 368 $[M+H]^+$.

Example 24B

Methyl 2-(1-(5-(4-aminophenyl)thiazol-2-yl)cyclobutoxy)acetate

A solution of Example 24A (0.750 g, 2/04 mmol), CsF (0.930 g, 6.12 mmol), 4-(4,4,5,5-tetramethyl-1,3,2-dioxaborolan-2-yl)aniline (0.447 g, 2.04 mmol), and tetrakis(triphenylphosphine)palladium(0) (0.231 g, 0.200 mmol) in a solvent mixture of dimethoxyethane (5 mL) and methanol (5 mL) was heated to 90° C. for 16 h. The reaction was cooled to room temperature and partitioned between $H_2O$ (10 mL) and ethyl acetate (10 mL). The layers were separated, and the aqueous was extracted with additional ethyl acetate (2×10 mL). The combined organics were dried with anhydrous $Na_2SO_4$, filtered, and concentrated under reduced pressure. The residue was purified by chromatography on $SiO_2$ gel, eluting with a gradient of 10% ethyl acetate in hexane to 50% ethyl acetate in hexane, to give the title compound. MS (ESI) m/z 319 $[M+H]^+$.

Example 24C

{[1-(5-{4-[(bicyclo[4.2.0]octa-1,3,5-trien-7-ylcarbonyl)amino]phenyl}-1,3-thiazol-2-yl)cyclobutyl]oxy}acetic acid To a solution of Example 24B (0.150 g, 0.470 mmol), 1,2-dihydrocyclobutabenzene-1-carboxylic acid (0.070 g, 0.470 mmol), N-methylmorpholine (0.103 mL, 0.940 mmol), and 1-hydroxybenzotriazole hydrate (0.080 g, 0.940 mmol) in N,N-dimethylformamide-(2 mL) was added 1-ethyl-3-[3-(dimethylamino)propyl]-carbodiimide hydrochloride (0.115 g, 0.589 mmol). The solution was heated to 50° C. for 3 h, cooled to room temperature, and partitioned between $H_2O$ (2 mL) and ethyl acetate (2 mL). The layers were separated, and the aqueous was extracted with additional ethyl acetate (2×2 mL). The combined organics were dried with anhydrous Na$_2$SO$_4$, filtered, and concentrated under reduced pressure. The residue was dissolved in methanol (5 mL) and 2 N NaOH (0.50 mL) was added. After 5 h, the methanol was removed under reduced pressure. The aqueous was acidified with 10% HCl to pH 1. The solid was filtered and air-dried. Purification of the residue by RP-HPLC (preparative reversed-phase high pressure liquid chromatography) using a Zorbax SB-C18 7M 21.2×250 mm column with UV detection analyzed at 220 and 254 nM (preparative method: water with 0.1% trifluoroacetic acid and CH$_3$CN with 0.1% trifluoroacetic acid gradient 5-95% CH$_3$CN over 30 minutes at 15 mL/min) provided the title compound as a white solid. $^1$H NMR (300 MHz, DMSO-d$_6$) δ ppm 1.67-1.94 (m, 2 H), 2.39-2.47 (m, 4 H), 3.31-3.40 (m, 2 H), 3.93 (s, 2 H) 4.44 (dd, J=4.9 and 2.9 Hz, 1 H), 7.09-7.31 (m, 4 H), 7.56-7.68 (m, 2 H), 7.67-7.78 (m, 2 H), 8.07 (s, 1 H), 10.37 (s, 1 H); MS (ESI) m/z 435 [M+H]$^+$.

Example 25

({1-[5-(4-{[(2-fluorophenyl)acetyl]amino}phenyl)-1,3-thiazol-2-yl]cyclobutyl}oxy)acetic acid Example 25 was prepared according to the procedure described for Example 24C, substituting 2-(2-fluorophenyl) acetic acid for 1,2-dihydrocyclobutabenzene-1-carboxylic acid. $^1$H NMR (300 MHz, DMSO-d$_6$) δ ppm 1.67-1.96 (m, 2 H), 2.39, 2.47 (m, 4 H), 3.75 (s, 2 H) 3.92 (s, 2 H), 7.10-7.25 (m, 2 H), 7.26-7.45 (m, 2 H), 7.53-7.75 (m, 4 H), 8.06 (s, 1 H), 1037 (s, 1 H), 12.64 (s, 1 H); MS (ESI) m/z 441 [M+H]$^+$.

Example 26

{[1-(5-{4-[(anilinocarbonyl)amino]phenyl}-1,3-thiazol-2-yl)cyclopentyl]oxy}acetic acid Example 26A 1-phenyl-3-(4-(4,4,5,5-tetramethyl-1,3,2-dioxaborolan-2-yl)phenyl)urea Example 26A was prepared according to the procedure described for Example 1A, substituting phenyl isocyanate for 2-fluor-5-trifluoromethylphenyl isocyanate. MS (ESI) m/z 339 [M+H]$^+$.

Example 26B

{[1-(5-{4-[(anilinocarbonyl)amino]phenyl}-1,3-thiazol-2-yl)cyclopentyl]oxy}acetic acid Example 26B was prepared according to the procedure described for Example 23B, substituting Example 26A for Example 1A. $^1$H NMR (300 MHz, DMSO-d$_6$) δ ppm 1.62-1.95 (m, 4 H), 2.01-2.20 (m, 4 H), 3.90 (s, 2 H), 6.98 (m, 1 H), 7.21-7.36 (m, 2 H), 7.40-7.63 (m, 6 H), 8.00 (s, 1 H), 8.73 (s, 1 H), 8.88 (s, 1 H), 12.59 (s, 1 H); MS (ESI) m/z 438 [M+H]$^+$.

Example 27

{[1-(5-{4-[(anilinocarbonyl)amino]phenyl}-1,3-thiazol-2-yl)cyclobutyl]oxy}acetic acid A solution of Example 24A (0.304 g, 0.953 mmol), Example 26A (0.209 g, 0.953 mmol), CsF (0.434 g, 2.86 mmol), and tetrakis(triphenylphosphine)palladium(0) (0.110 g, 0.095 mmol) in a solvent mixture of dimethoxyethane (5 mL) and methanol (5 mL) was heated to 90° C. for 16 h. The reaction was cooled to room temperature and diluted with H$_2$O (10 mL). The solid was filtered, washed with diethyl ether, and air-dried to give the intermediate ester. The ester was dissolved in methanol (50 mL) and 2N NaOH (2 mL) and stirred for 16 h. The methanol was removed under reduced pressure, and the aqueous was washed with diethyl ether (15 mL). The aqueous was acidified to pH 1 with 10% HCl. The solid was filtered, washed with CH$_3$CN, and air-dried to give the title compound. $^1$H NMR (500 MHz, DMSO-d$_6$) δ ppm 1.67-1.97 (m, 2 H), 2.35-2.52 (m, 4 H), 3.93 (s, 2 H), 6.91-7.01 (m, 1 H), 7.23-7.33 (m, 2 H), 7.41-7.50 (m, 2 H), 7.51-7.59 (m, 4 H), 8.04 (s, 1 H), 8.73 (s, 1 H), 8.82 (s, 1 H), 8.97 (s, 1 H); MS (ESI) m/z 424 [M+H]$^+$.

Example 28

{[1-(5-{6-[(anilinocarbonyl)amino]pyridin-3-yl}-1,3-thiazol-2-yl)cyclopentyl]oxy}acetic acid Example 28A 1-phenyl-3-(5-(4,4,5,5-tetramethyl-1,3,2-dioxaborolan-2-yl)pyridin-2-yl)urea To an ambient solution of 5-(4,4,5,5-tetramethyl-1,3,2-dioxaborolan-2-yl)pyridin-2-amine (0.350 g, 1.59 mmol) in tetrahydrofuran (4 mL) was added phenyl isocyanate (0.174 mL, 1.59 mmol). The solution was stirred at room temperature for 1 h and was then concentrated under reduced pressure. The solid was washed with diethyl ether (2 mL) and air-dried to give the title compound. MS (ESI) m/z 221 [M+H]$^+$.

Example 28B

{[1-(5-{6-[(anilinocarbonyl)amino]pyridin-3-yl}-1,3-thiazol-2-yl)cyclopentyl]oxy}acetic acid Example 28B was prepared according to the procedure described for Example 23B, substituting Example 28A for Example 1A. $^1$H NMR (300 MHz, DMSO-d$_6$) δ ppm 1.60-1.96 (m, 4 H), 2.13 (t, J=5.26 Hz, 4 H), 3.92 (s, 2 H), 7.03 (t, J=7.3 Hz, 1 H), 7.26-7.37 (m, 2 H), 7.47-7.58 (m, 2 H), 7.66 (m, 1 H), 7.99-8.14 (m, 2 H), 8.60 (m, 1 H), 9.57 (s, 1 H), 10.14 (s, 1 H), 12.60 (s, 1 H); MS (ESI) m/z 439 [M+H]$^+$.

Example 29

{[1-(5-{6-[({[3-(trifluoromethyl)phenyl]amino}carbonyl)amino]pyridin-3-yl}-1,3-thiazol-2-yl)cyclopentyl]oxy}acetic acid Example 29A 1-(5-(4,4,5,5-tetramethyl-1,3,2-dioxaborolan-2-yl)pyridin-2-yl)-3-(3-(trifluoromethyl)phenyl)urea Example 29A was prepared according to the procedure described for Example 28A, substituting 3-trifluoromethylphenyl isocyanate for phenyl isocyanate. MS (ESI) m/z 408 [M+H]$^+$.

Example 29B

{[1-(5-{6-[({[3-(trifluoromethyl)phenyl]amino}carbonyl)amino]pyridin-3-yl}-1,3-thiazol-2-yl)cyclopentyl]oxy}acetic acid Example 29B was prepared according to the procedure described for Example 23B, substituting Example 29A for Example 1A. $^1$H NMR (300 MHz, DMSO-d$_6$) δ ppm 1.63-1.95 (m, 4 H), 2.13 (t, J=5.1 Hz, 4 H), 3.92 (s, 2 H), 7.38 (d, J=7.8 Hz, 1 H), 7.56 (t, J=13 Hz, 1 H), 7.61-7.75 (m, 2 H), 7.95-8.15 (m, 3 H), 8.63 (m, 1 H), 9.70 (s, 1 H), 10.52 (s, 1 H), 12.61 (s, 1 H); MS (ESI) m/z 507 [M+H]$^+$.

Example 30

{[1-(4-{6-[(anilinocarbonyl)amino]pyridin-3-yl}phenyl)cyclopethyl]oxy}acetic acid Example 30A 1-(4-Bromophenyl)cyclopentanol To a cold (−78 °C.) solution of 1,4-dibromobenzene (33 g, 139.8 mmol) in tetrahydrofuran (200 mL) was added n-butyllithium (59.0 mL, 146.8 mmol, 2.49 M in hexane) dropwise. The viscous solution was stirred at −78° C. for 45 min, and cyclopentanone (13.6 mL, 153.8 mmol) was then added dropwise over 30 min. The resulting solution was stirred at −78° C. for 1 h and was then quenched by the addition of 0.5M HCl (200 mL) and ethyl acetate (200 mL). The layers; were separated, and the organics were washed with water (1×100 mL), brine (1×100 mL), dried over sodium sulfate, filtered, and concentrated under reduced pressure. The residue was purified by chromatography on SiO$_2$ gel, eluting with 5% ethyl acetate in hexane to give the title compound. $^1$H NMR (300 MHz, DMSO-d$_6$) δ ppm 1.71-1.76 (m, 2 H), 1.78-1.88 (m, 6 H), 4.85 (s, 1 H), 7.39-7.43 (m, 2 H), 7.44-7.49 (m, 2 H).

Example 30B 2-(1-(4-Bromophenyl)cyclopentyloxy)acetic acid

To an ambient suspension of NaH (332 mg, 8.30 mmol, 60 wgt % in mineral oil) in N,N-dimethylformamide (2 mL) was added dropwise a solution of Example 30A (1.0 g, 4.15 mmol) in N,N-dimethylformamide (1 mL). After 30 min., bromoacetic acid (577 mg, 4.15 mmol) in N,N-dimethylformamide (13 mL) was added, dropwise. The solution was stirred at room temperature for 16 h and then heated to 50° C. for 3 h. The reaction was cooled to room temperature and was quenched by the addition of water (10 mL). The solution was basicified to pH 10 by the addition of 2.5 M NaOH. The aqueous was extracted with ethyl acetate (2×10 mL), and the organics discarded. The aqueous was acidified to pH 1 with 6 M HCl, and then extracted with ethyl acetate (3×10 mL). The combined organics were washed with water (3×10 mL), brine (1×10 mL), dried over sodium sulfate, filtered, and concentrated, under reduced pressure to give the title compound. $^1$H NMR (300 MHz, DMSO-d$_6$) δ ppm 1.66-1.72 (m, 2 H), 1.74-1.85 (m, 4 H), 2.02-2.15 (m, 2 H), 3.56-3.60 (m, 2 H), 7.33-7.39 (m, 2 H), 7.49-7.56 (m, 2 H), 12.37 (s, 1 H).

Example 30C methyl 2-(1-(4-bromophenyl)cyclopentyloxy)acetate

To an ambient solution of Example 30B (200 mg, 0.668 mmol) in N,N-dimethylformamide (4 mL) was added iodomethahe (0.208 mL. 3.34 mmol) and potassium carbonate (184 mg, 1.34 mmol). The mixture was stirred at room temperature for 40 h, and then diluted with water (10 mL) and ethyl acetate (20 mL). The layers were separated, and the organic was washed with water (3×10 mL), brine (1×10 mL), dried over sodium sulfate, and concentrated under reduced pressure to give the title compound. $^1$H NMR (300 MHz, DMSO-d$_6$) δ ppm 1.67-1.72 (m, 2 H), 1.74-1.84 (m, 4 H), 2.10 (m, 2 H), 3.58 (s, 3 H), 3.67-3.70 (m, 2 H), 7.34-7.40 (m, 2 H), 7.51-7.57 (m, 2 H).

Example 30D

{[1-(4-{6-[(anilinocarbonyl)amino]pyridin-3-yl}phenyl)cyclopentyl]oxy}acetic acid A solution of Example 30C (0.040 g, 0,122 mmol), Example 28A (0.041 g, 0.122 mmol), CsF (0.056 g, 0.366 mmol), and tetrakis(triphenylphosphine)palladium(0) (0.014 g, 0.012 mmol) in dimethoxyethane (0.5 mL) and methanol (0.5 mL) was heated to 90° C. for 16 h. The reaction was diluted with H$_2$O (5 mL) and diethyl ether (5 mL), and the solid filtered. To the solid dissolved in a mixture of tetrahydrofuran (2 mL) and methanol (1 mL) was added 2 N NaOH (0.8 mL). After stirring at room temperature for 16 h, the organics were removed under reduced pressure. The aqueous was extracted with diethyl ether (1×5 mL), and the organics discarded. The aqueous was acidified to pH 1 with 10% HCl, and the solid was filtered. Purification of the solid residue by RP-HPLC (preparative reversed-phase high pressure liquid chromatography) using a Zorbax SB-C18 7M 21.2×250 mm column with UV detection analyzed at 220 and 254 nM (preparative method: water with 0.1% trifluoroacetic acid and CH$_3$CN with 0.1% trifluoroacetic acid gradient 5-95% CH$_3$CN over 30 minutes at 15 mL/min) provided the title compound as a white solid. $^1$H NMR (500 MHz, DMSO-d$_6$) δ ppm 1.60-1.78 (m, 2 H), 1.77-1.91 (m, 4 H), 2.02-2.19 (m, 2 H), 3.53 (s, 2 H), 7.02 (t, J=7.3 Hz, 1 H), 7.31 (t, J=7.9 Hz, 2 H), 7.48-7.59 (m, 4 H), 7.61-7.72 (m, 3 H), 8.07 (m, 1 H), 8.61 (m, 1 H), 9.67 (s, 1 H); MS (ESI) m/z 432 [M+H]$^+$.

Example 31

(±)-Cis-3-(4'-{[(2-fluorophenyl)acetyl]amino}-1,1'-biphenyl-4-yl)-3-hydroxycyclopentanecarboxylic acid Example 31A (±)-Cis-methyl 3-(4-bromophenyl)-3-hydroxycyclopentanecarboxylate To an ambient solution of Example 21A (1.69 g, 5.93 mmol) in methanol (15 mL) was added trimethylsilyldiazomethane (5.0 mL, 10.0 mmol, 2.0 M in tetrahydrofuran). The reaction was quenched by the addition of acetic acid (2 mL) and concentrated under reduced pressure. Purification of the residue by chromatography on SiO$_2$ gel, eluting with 25% ethyl acetate in hexane, gave the title product as an oil. MS (ESI) m/z 299 [M+H]$^+$.

Example 31B (±)-Cis-methyl 3-(4'-aminobiphenyl-4-yl)-3-hydrocyclopentanecarboxylate A solution of Example 31A (0.500 g, 1.67 mmol), 4-(4,4,5,5-tetramethyl-1,3,2-dioxaborolan-2-yl)aniline (0.366 g, 1.67 mmol), CsF (0.761 g, 5.01 mmol), and tetrakis(triphenylphosphine)palladium(0) (0.192 g, 0.167 mmol) in dimethoxyethane (4.0 mL) and methanol (4.0 mL) was heated to 90° C. for 16 h. The reaction was cooled to room temperature and partitioned between H₂O (10 mL) and ethyl acetate (10 mL). The layers were separated, and the aqueous was extracted with additional ethyl acetate (10 mL). The combined organics were dried with anhydrous Na₂SO₄, filtered, and concentrated under reduced pressure. The crude residue was purified by chromatography on SiO₂ gel, eluting with ethyl acetate, to give the title compound. MS (ESI) m/z 312 [M+H]⁺.

Example 31C (±)-Cis-3-(4'-{[(2-fluorophenyl)acetyl]amino}1,1'-biphenyl-4-yl)-3-hydroxycyclopentanecarboxylic acid To a solution of Example 31B (0.100 g, 0.321 mmol), 2-(2'-fluorophenyl)acetic acid (0.0490 g, 0.321 mmol), 1-hydroxybenzotriazole hydrate (0.0540 g, 0.402 mmol), and N-methylmorpholine (0.070 mL, 0.064 mmol) in N,N-dimethylformamide was added 1-ethyl-3-[3-(dimethylamino)propyl]-carbodiimide hydrochloride (0.0770 g, 0.402 mmol). The reaction was heated to 50° C. for 3 h, cooled to room temperature, and partitioned between H₂O (5 mL) and ethyl acetate (5 mL). The layers were separated, and the aqueous was extracted with additional ethyl acetate (2×5 mL). The combined organics were dried with anhydrous Na₂SO₄, filtered, and concentrated under reduced pressure. The crude residue was dissolved in methanol (10 mL), and 2 N NaOH (1 mL) was added. The reaction was stirred at room temperature for 16 h. The methanol was removed under reduced pressure, and the aqueous was acidified to pH 1 with 10% HCl. The solid was filtered, air-dried, and purified by RP-HPLC (preparative reversed-phase high pressure liquid chromatography) using a Zofbax SB-C18 7M 21.2×250 mm column with UV detection analyzed at 220 and 254 nM (preparative method; water with 0.1% trifluoroacetic acid and CH₃CN with 0.1% trifluoroacetic acid gradient 5-95% CH₃CN over 30 minutes at 15 mL/min) to provide the title compound as a white solid. ¹H NMR (300 MHz, DMSO-d₆) δ ppm 1.86-2.03 (m, 3 H), 2.14-2.26 (m, 3 H), 2.92-3.05 (m, 1 H), 4.06 (s, 2 H), 6.27 (s, 1 H), 7.16-7.20 (m, 2 H), 7.31-7.35 (m, 1 H), 7.39-7.42 (m, 1 H), 7.52-7.56 (m, 2 H), 7.62-7.71 (m, 6 H), 10.32 (s, 1 H), 12.0 (s, 1 H); MS (ESI) m/z 434 [M+H]⁺.

Example 32

[(1-{5-[4-({2-[(4-chlorophenyl)amino]-3,4-dioxocyclobut-1-en-1-yl}amino)phenyl]-1,3-thiazol-2-yl}cyclobutyl)oxy]acetic acid Example 32A 3-(4-chlorophenylamino)-4-ethoxycyclobut-3-ene-1,2-dione To a refluxing solution of 3,4-diethoxycyclobut-3-ene-1,2-dione (1.05 g, 6.14 mmol) in ethanol (25 mL) was added an ethanol (10 mL) solution of 4-chloroaniline (0.784 g, 6.14 mmol) by syringe pump over 2 h. The heating bath was removed, and the reaction stirred at room temperature for 16 h. The reaction was concentrated under reduced pressure and purified by chromatography oh SiO₂ gel, eluting with 50% ethyl acetate in hexane to give the title compound. MS (ESI) m/z 252 [M+H]⁺.

Example 32B

[(1-{5-[4-({2-[(4-chlorophenyl)amino]-3,4-dibxocyclobut-1-en-1-yl}amino)phenyl]-1,3-thiazol-2-yl}cyclobutyl)oxy]acetic acid A solution of Example 32A (0.063 g, 0.198 mmol) and Example 24B (0.050 g, 0.198 mmol) was heated to 90° C. for 16 h. The reaction, was cooled to room temperature, and 2 N NaOH (0.5 mL) was added. After 16 h, the ethanol was removed under reduced pressure, and the aqueous acidified to pH 1 by the addition of 10% HCl. The solid was filtered, air-dried, and purified by RP-HPLC (preparative reversed-phase high pressure liquid chromatography) using a Zorbax SB-C18 7M 21.2×250 mm column with UV detection analyzed at 220 and 254 nM (preparative method: water with 0.1% trifluoroacetic acid and CH₃CN with 0.1% trifluoroacetic acid gradient 5-95% CH₃CN over 30 minutes at 15 mL/min) to provide the title compound as a white solid. ¹H NMR (500 MHz, DMSO-d₆) δ ppm 1.72-1.95 (m, 2 H), 2.40-2.49 (m, 4 H), 3.93 (s, 2 H) 7.40-7.47 (m, 2 H), 7.48-7.53 (m, 2 H), 7.55 (m, 2 H), 7.68 (m, 2 H), 8.11 (s, 1 H), 10.12 (m, 2 H), 12.0 (s, 1 H); MS (ESI) m/z 510 [M+H]⁺.

Example 33

{[1-(5-{4-[(anilinocarbonyl)amino]phenyl}-4-methyl-1,3-thiazol-2-yl)cyclopentyl]oxy}acetic acid Example 33A 1-(5-iodo-4-methylthiazol-2-yl)cyclopentanol To a cold (−78° C.) solution of 4-methylthiazole (2.0 mL, 20.2 mmol) in tetrahydrofuran (130 mL) was added n-butyllithium (8.10 mL, 20.2 mmol, 2.48 M in hexane) dropwise. After 15 minutes, cyclopentanone (1.79 mL, 20.2 mmol) was added in a single portion. After 30 minutes, n-butyllithium (8.10 mL, 20.2 mmol, 2.48 M in hexane) was added dropwise. The reaction was allowed to stir for art additional 20 minutes, after which a solution of iodine (5.13 g, 20.2 mmol) in tetrahydrofuran (15 mL) was added dropwise. The reaction was then quenched by the addition of saturated aqueous Na₂S₂O₃ and ethyl acetate (1.0.0 mL) and allowed to warm to ambient temperature. The layers were separated, and the aqueous was extracted with additional ethyl acetate (2×100 mL). The combined organics were dried with anhydrous Na₂SO₄, filtered, and concentrated to give a dark solid. Trituration of the residue with hexane gave the title compound as a beige solid. MS (ESI) m/z 310 [M+H]⁺.

Example 33B ethyl 2-(1-(5-iodo-4-methylthiazol-2-yl)cyclopentyloxy)acetate

To a suspension of NaH (0.808 g, 20.2 mmol, 60 wt % in mineral oil) in N,N-dimethylformamide (40 mL) was added Example 33A (6.24 g, 20.2 mmol). After 0.5 h, ethyl bromoacetate (2.23 mL, 20.2 mmol) was added, and the reaction was stirred for 16 h. The reaction was partitioned between H₂O (50 mL) and ethyl acetate (50 mL). The layers were separated, and the aqueous was extracted with additional ethyl acetate (2×50 mL). The combined organic layers were dried with anhydrous Na₂SO₄, filtered and concentrated under reduced pressure. The residue was purified by chromatography on SiO₂ gel, eluting with 5% ethyl acetate in hexane, to give the title compound. MS (ESI) m/z 396 [M+H]⁺.

Example 33C

{[1-(5-{4-[(anilinocarbonyl)amino]phenyl}-4-methyl-1,3-thiazol-2-yl)cyclopentyl]oxy}acetic acid A solution of Example 33B (0.090 g, 0.228 mmol), Example 26A (0.077 g, 0.228 mmol), CsF (0.104 g, 0.684 mmol), and tetrakis(triphenylphosphine)palladium(0) (0.027 g, 0.023 mmol) in a solvent mixture of dimethoxyethane (1 mL) and methanol (1 mL) was heated to 90° C. for 16 h. The reaction was cooled to warm temperature and diluted with H₂O (2 mL). The solid was filtered, washed with diethyl ether, and air-dried to give the intermediate ester. The ester was dissolved in a mixture of methanol (8 mL) and 2N NaOH (1 mL) and stirred for 16 h. The methanol was removed under reduced pressure, and the aqueous was washed with diethyl ether (5 mL). The aqueous was acidified to pH 1 with 10% HCl. The resulting solid was filtered, washed with CH₃CN, air-dried, and purified by RP-HPLC (preparative reversed-phase high pressure liquid chromatography) using a Zorbax SB-C18 7M 21.2×250 mm column with UV detection analyzed at 220 and 254 nM (preparative method: water with 0.1% trifluoroacetic acid and CH₃CN with 0.1% trifluoroacetic acid gradient 5-95% CH₃CN over 30 minutes at 15 mL/min) to provide the title compound as a white solid: ¹H NMR (500 MHz, DMSO-d₆) δ ppm 1.66-1.90 (m, 4 H), 2.03-2.16 (m, 4 H), 2.40 (s, 3 H), 3.92 (s, 2 H), 6.98 (t, J=7.48 Hz, 1 H) 7.24-7.32 (m, 2 H), 7.40 (m, 2 H), 7.46 (m, 2 H), 7.55 (m, 2 H), 8.71 (s, 1 H), 8.85 (s, 1 H), 12.38-12.80 (s, 1 H); MS (ESI) m/z 452 [M+H]⁺.

Example 34

{[1-(4-methyl-5-{4-[({[3-(trifluoromethyl)phenyl]amino}carbonyl)amino]phenyl}-1,3-thiazol-2-yl)cyclopentyl]oxy}acetic acid Example 34 was prepared according to the procedure described for Example 33C, substituting Example 18A for Example 26A. ¹H NMR (500 MHz, DMSO-d₆) δ ppm 1.69-1.88 (m, 4 H), 2.03-2.14 (m, 4 H), 2.36-2.43 (m, 3 H), 3.92 (s, 2 H), 7.29-7.35 (m, 1 H), 7.39-7.44 (m, 2 H), 7.50-7.55 (m, 2 H), 7.55-7.62 (m, 2 H), 8.02 (s, 1 H), 8.99 (s, 1 H), 9.11 (s, 1 H); MS (ESI) m/z 521 [M+H]⁺.

Example 35

{[1-(5-{6-[(anilinocarbonyl)amino]pyridin-3-yl}-4-methyl-1,3-thiazol-2-yl)cyclopentyl]oxy}acetic acid Example 35 was prepared according to the procedure, described for Example 33C, substituting Example 28A for Example 26A. ¹H NMR (500 MHz, DMSO-d₆) δ ppm 1.64-1.92 (m, 4 H), 2.11 (t, J=5.34 Hz, 4 H), 2.41 (s, 3 H), 3.94 (s, 2 H), 6.91-7.11 (m, 1 H), 7.24-7.37 (m, 2 H), 7.46-7.57 (m, 2 H), 7.60-7.73 (m, 1 H), 7.81-7.93 (m, 1 H), 8.32-8.46 (m, 1 H), 9.56 (s, 1 H), 10.21 (s, 1 H); MS (ESI) m/z 453 [M+H]⁺.

Example 36

{[1-(4-methyl-5-{6-[({[3-(trifluormethyl)phenyl]amino}carbonyl)amino]pyridin-3-yl}-1,3-thiazol-2-yl)cyclopentyl]oxy}acetic acid Example 36 was prepared according to the procedure described for Example 33C, substituting Example 29A for Example 26A. ¹H NMR (500 MHz, DMSO-d₆) δ ppm 1.67-1.91 (m, 4 H), 2.02-2.17 (m, 4 H), 2.33-2.46 (m, 3 H), 3.91-3.97 (m, 2 H), 7.36-7.40 (m, 1 H), 7.49-7.62 (m, 1 H), 7.61-7.75 (m, 2 H), 7.90-7.92 (m, 1 H), 8.09 (s, 1 H), 8.44 (s, 1 H), 9.70 (s, 1 H), 10.60 (s, 1 H); MS (ESI) m/z 521 [M+H]⁺.

Example 37

{[1-(5-{6-[({[2-fluoro-5-(trifluromethyl)phenyl]amino}carbonyl)amino]pyridin-3-yl}-1,3-thiazol-2-yl)cyclopentyl]oxy}acetic acid

Example 37A 1-(2-fluoro-5-(trifluoromethyl)phenyl)-3-(5-(4,4,5,5-tetramethyl-1,3,2-dioxaborolan-2-yl)pyridin-2-yl)urea Example 37A was prepared according to the procedure described for Example 28A, substituting 2-fluoro-5-trifluoromethylphenylisocyanate for phenylisocyanate. MS (ESI) m/z 426 [M+H]⁺.

Example 37B

{[1-(5-{6-[({[2-fluoro-5-(trifluoromethyl)phenyl]amino}carbonyl)amino]pyridin-3-yl}-1,3-thiazol-2-yl)cyclopentyl]oxy}acetic acid Example 37B was prepared according to the procedure described for Example 33C, substituting Example 37A for Example 26A, and substituting Example 23A for Example 33B. ¹H NMR (300 MHz, DMSO-d₆) δ ppm 1.65-1.91 (m, 4 H), 2.06-2.19 (m, 4 H), 3.92 (s, 2 H), 7.43-7.49 (m, 1 H), 7.51-7.59 (m, 1 H), 7.59-7.68 (m, 1 H), 8.08 (m, 1 H), 8.15 (s, 1 H), 8.56-8.63 (m, 1 H), 8.63-8.70 (m, 1 H), 10.09 (s, 1 H), 10.75 (s, 1 H); MS (ESI) m/z 584 [M+H]⁺.

Example 38

2-{[1-(5-{6-[({[3-(trifluoromethyl)phenyl]amino}carbonyl)amino]pyridin-3-yl}-1,3-thiazol-2-yl)cyclopentyl]oxy}propanoic acid

Example 38A ethyl 2-(1-(5-iodothiazol-2-yl)cyclopentyloxy)propanoate

Example 38A was prepared according to the procedure described for Example 22A, substituting ethyl 2-bromopropanoate for iodomethane. MS (ESI) m/z 396 [M+H]⁺.

Example 38B

2-{[1-(5-{6-[({[3-(trifluoromethyl)phenyl]amino}carbonyl)amino]pyridin-3-yl}-1,3-thiazol-2-yl)cyclopentyl]oxy}propanoic acid A solution of Example 38A (0.040 g, 0.101 mmol), Example 29A (0.041 g, 0.101 mmol), CsF (0.046 g, 0.304 mmol), and tetrakis(triphenylphosphine)palladium(0) (0.0120 g, 0.010 mmol) in a solvent mixture of dimethoxyethane (0.5 mL) and methanol (0.5 mL) was heated to 90° C. for 16 h. The reaction was cooled to room temperature and diluted with H₂O (2 mL). The solid was filtered, washed with diethyl ether, and air-dried to give the intermediate ester. The ester was dissolved in methanol (2 mL) and 2N NaOH (0.3 mL) and stirred for 16 h. The methanol was removed under reduced pressure, and the aqueous; was washed with diethyl ether (2 mL). The aqueous was acidified to pH 1 with 10% HCl. The solid was filtered, washed with $CH_3CN$, air-dried and purified by RP-HPLC (preparative reversed-phase high pressure liquid chromatography) using a Zorbax SB-C18 7M 21.2×250 mm column with UV detection analyzed at 220 and 254 nM (preparative method: water with 0.1% trifluoroacetic acid and $CH_3CN$ with 0.1% trifluoroacetic acid gradient 5-95% $CH_3CN$ over 30 minutes at 15 mL/min) to provide the title compound as a white solid. $^1$H NMR (300 MHz, DMSO-$d_6$) δ ppm 1.25 (d, J=6.78 Hz, 3 H), 1.64-1.78 (m, 2 H), 1.80-1.92 (m, 2 H), 1.96-2.18 (m, 3 H), 2.21-2.32 (m, 1 H), 3.84-4.00 (m, 1 H), 7.32-7.42 (m, 1 H), 7.50-7.60 (m, 2 H), 7.64-7.72 (m, 2 H), 8.03-8.12 (m, 2 H), 8.12 (s, 1 H), 8.51-8.70 (m, 1 H), 9.70 (s, 1 H), 10.51 (s, 1 H); MS (ESI) m/z 521 $[M+H]^+$.

Example 39

2-{[1-(5-{6-[(anilinocarbonyl)amino]pyridin-3-yl}-1,3-thiazol-2-yl)cyclopentyl]oxy}propanoic acid Example 39 was prepared according to the procedure described for Example 38B, substituting Example 28A for Example 29A. $^1$H NMR (300 MHz, DMSO-$d_6$) δ ppm 1.25 (d, J=6.78 Hz, 3 H), 1.63-1.78 (m, 2 H), 1.80-1.92 (m, 2 H), 1.93-2.04 (m, 2 H), 2.04-2.18 (m, 2 H), 2.20-2.33 (m, 1 H), 3.90-3.95 (m, 1 H), 7.35-7.41 (m, 1 H), 7.54-7.58 (m, 2 H), 7.63-7.72 (m, 2 H), 8.05-8.11 (m, 2 H), 8.12 (s, 1 H), 8.59-8.66 (m, 1 H), 9.70 (s, 1 H); MS (ESI) m/z 521 $[M+H]^+$.

Example 40

{[1-(5-{4-[(7-methyl-1,3-benzoxazol-2-yl)amino]phenyl}-1,3-thiazol-2-yl)cyclopentyl]oxy}acetic acid A solution of Example 4B (0.20 g, 0.57 mmol), Example 23A (0.19 g, 0.57 mmol), CsF (0.26 g, 1.71 mmol), and tetrakis(triphenylphosphine)palladium(0) (0.066 g, 0.057 mmol) in a solvent mixture of dimethoxyethane (1 mL) and methanol (1 mL) was heated to 90° C. for 16 h. The reaction was cooled to room temperature and diluted with $H_2O$ (5 mL). The solid was filtered, air-dried. The solid was dissolved in tetrahydrofuran (1.0 mL) and methanol (10 mL) and 2 N NaOH (2 mL) was added. After 16 h, the organics were removed under reduced pressure, and the aqueous was acidified to pH 1 with 10% HCl. The solid was filtered, air-dried, and purified, by RP-HPLC (preparative reversed-phase high pressure liquid chromatography) using a Zorbax SB-C18 7M 21.2×250 mm column with UV detection analyzed at 220 and 254 nM (preparative method: water with 0.1% trifluoroacetic acid and $CH_3CN$ with 0.1% trifluoroacetic acid gradient. 5-95% $CH_3CN$ over 30 minutes at 15 mL/min) to provide the title compound as a white solid. $^1$H NMR (500 MHz, DMSO-$d_6$) δ ppm 1.65-1.77 (m, 2 H), 1.76-1.89 (m, 2 H), 2.08-2.20 (m, 4 H), 2.44 (s, 3 H), 3-91 (s, 2 H), 6.85-7.02 (m, 1 H), 7.10-7.19 (m, 1 H), 7.22-7.36 (m, 1 H), 7.59-7.70-7.75 (m, 2 H), 7.77-7.88 (m, 2 H), 7.94-8.05 (m, 1 H), 10.87 (s, 1 H); MS (ESI) m/z 482 $[M+H]^+$.

Example 41

N-{4-[2-(4-hydroxytetrahydro-2H-pyran-4-yl)-1,3-thiazol-5-yl]phenyl}-2-[3-(trifluoromethyl)phenyl]acetamide A solution of Example 11B (0.025 g, 0.091 mmol), 2-(3-(trifluoromethyl)phenyl)acetic acid (0.019 g, 0.091 mmol), 1-ethyl-3-[3-(dimethylamino)propyl]-carbodiimide hydrochloride (0.019 g, 0.10 mmol), 1-hydroxybenzotriazole hydrate (0.013 g, 0.10 mmol), and N-methylmorpholine (0.050 mL, 0.46 mmol) in N,N-dimethylformamide (1 mL) was heated to 55° C. for 16 h. The reaction was cooled to room temperature and diluted with ethyl acetate (2 mL) and $H_2O$ (2×1 mL). The layers were separated, and the organic was washed with brine (1×1 mL), dried with anhydrous $Na_2SO_4$, filtered, and concentrated under reduced pressure. The residue was purified by RP-HPLC (preparative reversed-phase high pressure liquid chromatography) using a Zorbax SB-C18 7M 21.2×250 mm column with UV detection analyzed at 220 and 254 nM (preparative method: water with 0.1% trifluoroacetic acid and $CH_3CN$ with 0.1% trifluoroacetic acid gradient 5-95% $CH_3CN$ over 30 minutes at 15 mL/min) to provide the title compound as a white solid. $^1$H NMR (300 MHz, DMSO-$d_6$) δppm 1.66-1.72 (m, 2 H), 2.09-2.13 (m, 2 H) 3.67-3.78 (m, 5 H), 3.80 (s, 2 H), 7.57-7.71 (m, 8 H), 7.99 (s, 1 H), 10.36 (s, 1 H); MS (ESI) m/z 463 $[M+H]^+$.

Example 42

2-(2,4-difluorophenyl)-N-{4-[2-(4-hydroxytetrahydro-2H-pyran-4-yl)-1,3-thiazol-5-yl]phenyl}acetamide Example 42 was prepared according to that described for Example 41, substituting 2-(2,4-difluorophenyl)acetic acid for 2-(3-(trifluoromethyl)phenyl)acetic acid. $^1$H NMR (300 MHz, DMSO-$d_6$) δ ppm 1.66-1.70 (m, 2 H), 2.09-2.13 (m, 2 H), 3.72-3.76 (m, 7 H), 7.02-7.08 (m, 1 H) 7.20-7.24 (m, 1 H) 7.40-7.48 (m, 1 H), 7.54-7.67 (m, 4 H), 8.00 (s, 1 H), 10.34 (s, 1 H); MS (ESI) m/z 431 $[M+H]^+$.

Example 43

2-(2,5-difluprophenyl)-N-{4-[2-(4-hydroxytetrahydro-2H-pyran-4-yl)-1,3-thiazol-5-yl]phenyl}acetamide Example 43 was prepared according to that described for Example 41, substituting 2-(2,5-difluorophenyl)acetic acid for 2-(3-(trifluoromethyl)phenyl)acetic acid. $^1$H NMR (300 MHz, DMSO-$d_6$) δ ppm 1.66-1.70 (m, 2 H), 2.06-2.16 (m, 2 H), 3.74-3.78 (m, 7 H), 7.15-7.30 (m, 3 H), 7.57-7.67 (m, 4 H), 8.00 (s, 1 H), 10.36 (s, 1 H); MS (ESI) m/z 431 $[M+H]^+$.

Example 44

[(1-{5-[4-(benzoylamino)phenyl]-1,3-thiazol-2-yl}cyclobutyl)oxy]acetic acid

A N,N-dimethylformamide (1 mL) solution of Example 24B (0.025 g, 0.079 mmol), benzoic acid (0.011 g, 0.087 mmol), 1-ethyl-3-[3-(dimethylamino)propyl]-carbodiimide hydrochloride (0.015 g, 0.079 mmol), 1-hydroxybenzotriazole hydrate (0.011 g, 0.079 mmol), and N-methylmorpholine (0.345 mL, 0.314 mmol) was heated to 55° C. for 16 h. The solution was cooled to room temperature and diluted with ethyl acetate (2 mL) and $H_2O$ (2 mL). The layers were separated, and the organic was washed with brine (1×1 mL), dried with anhydrous $Na_2SO_4$, filtered, and concentrated under reduced pressure. The residue was dissolved in methanol (2 mL) and 2.5M NaOH (0.95 mL, 0.237 mmol) was added. The reaction was stirred at room temperature for 16 h, concentrated under reduced pressure, and purified by RP-HPLC (preparative reversed-phase high pressure liquid chromatog-

Example 45

({1-[5-(4-{[(3-fluorophenyl)acetyl]amino}phenyl)-1, 3-thiazol-2-yl]cyclobutyl}oxy)acetic acid Example 45 was prepared according to that described for Example 44, substituting 2-(3-fluorophenyl)acetic acid for benzoic acid. $^1$H NMR (300 MHz, METHANOL-d$_4$) δ ppm 1.81-1.92 (m, 1 H), 1.93-2.05 (m, 1 H), 2.50-2.65 (m, 5 H), 3.71 (s, 2 H), 3.94-3.98 (m, 2 H), 7.00 (m, 1 H), 7.09-7.19 (m, 2 H), 7.34 (m, 1 H), 7.56-7.67 (m, 5 H), 7.93 (s, 1 H); MS (ESI) m/z 441 [M+H]$^+$.

Example 46

({1-[5-(4-{[4-(trifluoromethyl)benzoyl] amino}phenyl)-1,3-thiazol-2-yl]cyclobutyl}oxy) acetic acid Example 46 was prepared according to that described for Example 44, substituting 4-(trifluoromethyl)benzoic acid for benzoic acid. $^1$H NMR (300 MHz, METHANOL-d$_6$) δ ppm 1.88 (m, 1 H), 1.95-2.05 (m, 1 H), 2.51-2.66 (m, 5 H), 3.98 (s, 2 H), 7.66 (m, 2 H), 7.80-7.86 (m, 5 H), 7.98 (s, 1 H), 8.11 (m, 2 H); MS (ESI) m/z 477 [M+H]$^+$.

Example 47

[(1-{5-[4-({[2-fluoro-5-(trifluoromethyl)phenyl] acetyl}amino)phenyl]-1,3-thiazol-2-yl}cyclobutyl) oxy]acetic acid Example 47 was prepared according to that described for Example 44; substituting 2-(2-fluoro-5-(trifluoromethyl) phenyl)acetic acid for benzoic acid. $^1$H NMR (300 MHz, METHANOL-d$_4$) δ ppm 1.87 (m, 1 H), 1.93-2.05 (m, 1 H), 2.49-2.64 (m, 5 H), 3.87 (s, 2 H), 3.97 (s, 2 H), 7.31 (m, 1 H), 7.57-7.68 (m, 6 H), 7.75 (m, 1 H), 7.94 (s, 1 H); MS (ESI) m/z 509 [M+H]$^+$.

Example 48

{[1-(5-{6-[({[3-(trifluoromethyl)phenyl] amino}carbonyl)amino]pyridin-3-yl}-1,3-oxazol-2-yl)cyclopentyl]oxy}acetic acid

Example 48A 1-(oxazol-2-yl)cyclopentanol

An ambient solution of oxazole (1.00 g, 14.5 mmol) and borane●tetrahydrofuran complex (14.5 mL, 14.5 mmol, 1 M in tetrahydrofuran) was stirred for 30 min. The solution was cooled to −78° C., and n-butyllithium (9.5 mL, 15.2 mmol, 1.6 M in hexane) was added dropwise. After 30 minutes, cyclopentanone (1.42 mL, 16.0 mmol) was added dropwise. After 30 minutes, the cold (−78° C.) reaction was quenched by the addition of 5% acetic acid in ethanol (70 mL) and warmed to room temperature. The solution was diluted with diethyl ether (10.0 mL) and saturated NaHCO$_3$ (50 mL). Layers were separated, and the organics were washed with brine (1×50 mL), dried over Na$_2$SO$_4$, concentrated under reduced pressure, and purified by chromatography on SiO$_2$ gel, eluting with 50% ethyl acetate in hexane, to give the title compound. $^1$H NMR (300 MHz, DMSO-d$_6$) δ ppm 1.59-1.71 (m, 2 H), 1.72-1.84 (m, 2 H), 1.84-1.96 (m, 2 H), 1.98-2.09 (m, 2 H), 5.40 (s, 1 H), 7.11 (s, 1 H), 8.02 (s, 1 H).

Example 48B 1-(5-iodooxazol-2-yl)cyclopentanol

To a cold (−78 °C.) solution of Example 48A (500 mg, 3.26 mmol) in tetrahydrofuran (50 mL) was added n-butyllithium (4.08 mL, 6.53 mmol, 1.6M in hexane) dropwise. After stirring for 30 min, a solution of iodine (0.829 g, 3.26 mmol) in tetrahydrofuran (5 mL) was added dropwise. After 2 h, the reaction was quenched by the addition of 10% Na$_2$S$_2$O$_3$ solution (0.10 mL) and ethyl acetate (10 mL) and warmed to room temperature. The layers were separated, and the aqueous was extracted with additional ethyl acetate (2×50 mL). The combined organics were washed with brine (1×50 mL), dried over Na$_2$SO$_4$, concentrated under reduced pressure, and purified by chromatography on SiO$_2$ gel, eluting with 50% ethyl acetate in hexane, to give the title compound. $^1$H NMR (300 MHz, DMSO-d$_6$) δ ppm 1.65 (s, 2 H), 1.79 (s, 2 H), 1.89 (s, 2 H), 2.02 (s, 2 H), 5.50 (s, 1 H), 7.22 (s, 1 H).

Example 48C ethyl 2-(1-(5-iodooxazol-2-yl)cyclopentyloxy)acetate

Example 48C was prepared according to the procedure described for 24A, substituting Example 48B for Example 19A. $^1$H NMR (300 MHz, DMSO-d$_6$) δ ppm 1.14-1.17 (m, 3 H), 1.59-1.68 (m, 2 H), 1.71-1.81 (m, 2 H), 2.03-2.11 (m, 4 H), 3.92 (s, 2 H), 3.99-4.06 (m, 2 H), 7.28 (s, 1 H).

Example 48D

{[1-(5-{6-[({[3-(trifluoromethyl)phenyl] amino}carbonyl)amino]pyridin-3-yl}-1,3-oxazol-2-yl)cyclopentyl]oxy}acetic acid A solution of Example 48C (0.103 g, 0.282 mmol), Example 29A (0.115 g, 0.282 mmol), CsF (0.129 g, 0.847 mmol), and tetrakis(triphenylphosphine)palladium(0) (0.033 g, 0.028 mmol) in dimethoxyethane (2 mL) and ethanol (1 mL) was heated under microwave irradiation to 150 °C. for 5 min. the reaction was then concentrated under reduced pressure. The residue was purified by RP-HPLC (preparative reversed-phase high pressure liquid chromatography) using a Zorbax SB-C18 7M 21.2×250 mm column with UV detection analyzed at 220 and 254 nM (preparative method: water with 0.1% trifluoroacetic acid and CH$_3$CN with 0.1% trifluoroacetic acid gradient 5-95% CH$_3$CN over 30 minutes at 15 mL/min) to provide the intermediate ester. The ester was dissolved in methanol (2 mL) and 2.5M NaOH (0.340 mL) was added. After 16 h, the organics were removed under reduced pressure. The aqueous was acidified to pH 1 with 10% HCl. The solid was filtered, washed with CH$_3$CN, and dried to give the title compound. $^1$H NMR (300 MHz, DMSO-d$_6$) δ ppm 1.67 (m, 2 H), 1.82 (m, 2 H), 2.12-2.22 (m, 4 H), 3.92 (s, 2 H), 7.38 (m, 1 H), 7.52-7.60 (m, 1 H), 7.61 (s, 1 H) 7.69 (m, 2 H), 8.06-8.10 (m, 2 H), 8.69 (m, 1 H), 9.74 (s, 1 H), 10.52 (s, 1 H), 12.45 (s, 1 H); MS (ESI) m/z 491 [M+H]$^+$.

Example 49

({1-[5-(4-{[(2,5-difluorophenyl)acetyl]amino}phenyl)-1,3-thiazol-2-yl]cyclobutyl}oxy)acetic acid Example 49 was prepared according to the procedure described for Example 44, substituting 2-(2,5-difluorophenyl)acetic acid for benzoic acid. $^1$H NMR (300 MHz, DMSO-d$_6$) δ ppm 1.73-1.83 (m, 1 H), 1.83-1.94 (m, 1 H), 2.43-2.48 (m, 4 H), 3.75-3.79 (m, 2 H), 3.93 (s, 2 H), 7.15-7.31 (m, 3 H), 7.59-7.69 (m, 4 H), 8.07 (s, 1 H), 10.37 (s, 1 H), 12.66 (s, 1 H); MS (ESI) m/z 459 [M+H]$^+$.

Example 50

({1-[5-(4-{[(3,5-difluorophenyl)acetyl]amino}phenyl)-1,3-thiazol-2-yl]cyclobutyl}oxy)acetic acid Example 50 was prepared according to the procedure described for Example 44, substituting 2-(3,5-difluorophenyl)acetic acid for benzoic acid. $^1$H NMR (300 MHz, DMSO-d$_6$) δ ppm 1.73-1.84 (m, 1 H), 1.84-1.93 (m, 1 H), 2.41-2.48 (m, 4 H), 3.73 (s, 2 H), 3.93 (s, 2H), 7.03-7.17 (m, 3 H), 7.59-7.69 (m, 5 . H), 8.06 (s, 1 H), 10.34 (s, 1 H); MS (ESI) m/z 459 [M+H]$^+$.

Example 51

({1-[5-(4-{[(3,4-difluorophenyl)acetyl]amino}phenyl)-1,3-thiazol-2-yl]cyclobutyl}oxy)acetic acid Example 51 was prepared according to the procedure described for Example 44, substituting 2-(3,4-difluorophenyl)acetic acid for benzoic acid. $^1$H NMR (300 MHz, DMSO-d$_6$) δ ppm 1.73-1.83 (m, 1 H), 1.83-1.94 (m, 1 H), 2.41-2.48 (m, 4 H), 3.69 (s, 2 H), 3.93 (s, 2 H), 7.17 (m, 1 H), 7.34-7.43 (m, 2 H), 7.59-7.69 (m, 5 H), 8.06 (s, 1 H) 10.32 (s, 1 H); MS (ESI) m/z 459 [M+H]$^+$.

Example 52

{[1-(4-{6-[({[3-(trifluoromethyl)phenyl]amino}carbonyl)amino]pyridin-3-yl}phenyl)cyclopentyl]oxy}acetic acid Example 52 was prepared according to the procedure described for Example 30D, substituting Example 29A for Example 28A. $^1$H NMR (300 MHz, DMSO-d$_6$) δ ppm 1.71 (s, 2 H), 1.79-1.91 (m, 4 H), 2.08-2.18 (m, 2 H), 3.63 (s, 2 H), 7.36-7.40 (m, 1 H), 7.50-7.55 (m, 2 H), 7.55-7.60 (m, 1 H) 7.62-7.65 (m, 1 H), 7.67-7.71 (m, 3 H), 8.07-8.13 (m, 2 H), 8.64-8.68 (m, 1 H), 9.64 (s, 1 H), 10.72 (s, 1 H), 12.42 (s, 1 H); MS (ESI) m/z 500 [M+H]$^+$.

Example 53

2-(1-(2-fluoro-4-(6-(3-(3-(trifluoromethyl)phenyl)ureido)pyridin-3-yl)phenyl)cyclobutoxy)acetic acid Example 53A methyl 4-bromo-2-fluorobenzoate An ambient suspension of 4-bromo-2-fluorobenzoic acid (15.0 g, 68.5 mmol), iodomethane (21.0 mL, 342.5 mmol), and potassium carbonate (19.0 g, 137 mmol) in N,N-dimethylformamide (200 mL) was stirred at room temperature for 16 h, after which it was diluted with ethyl acetate (200 mL) and water (100 mL). The layers were separated, and the organics were washed with water (3×100 mL) and brine (1×100 mL), dried over sodium sulfate, and concentrated under reduced pressure. The residue was passed through a plug of SiO$_2$ gel, eluting with 50% ethyl acetate in hexane, to give the title compound as a solid. MS (ESI) m/z 233 [M+H]$^+$.

Example 53B 1-(4-bromo-2-fluorophenyl)cyclopentanol

A 100 mL 3N round-bottom flask was charged with magnesium (0.700 mg, 23.8 mmol) and tetrahydrofuran (30 mL). The suspension was stirred and cooled to 0° C. 1,4-Dibromobutane (1.65 mL, 13.94 mmol) was slowly added, and the solution was allowed to warm to room temperature. After 30 min, the solution was cooled to 0° C., and Example 53A (1.00 g, 4.29 mmol) in tetrahydrofuran (10 mL) was added dropwise. After 30 min, the solution was allowed to warm to room temperature and was stirred for an additional 1 h. The solution was quenched by the careful addition of saturated NH$_4$Cl and ethyl acetate (50 mL). The layers were separated, and the organics were washed with water (2×50 mL) and brine (1×50 mL), dried over anhydrous Na$_2$SO$_4$, filtered, and Concentrated under reduced pressure. The residue was purified by chromatography on SiO$_2$ gel, eluting with 3% ethyl acetate in hexane, to give the title compound. MS (ESI) m/z 259 [M+H]$^+$.

Example 53C 2-(1-(4-bromo-2-fluorophenyl)cyclopentyloxy)acetic acid

Example 53C was prepared according to the procedure described for Example 30B, substituting Example 53B for Example 3A. MS (ESI) m/z 317 [M+H]$^+$.

Example 53D 2-(1-(2-fluoro-4-(6-(3-(3-(trifluoromethyl)phenyl)ureido)pyridin-3-yl)phenyl)cyclobutoxy)acetic acid A mixture of Example 29A (0.37 g, 0.31 mmol), Example 53C (0.29 g, 0.31 mmol), potassium phosphate (0.474 g, 2.73 mmol), and 1,1'-bis(di-tert-butylphosphino)ferrocene palladium(II)dichloride (0.03 g, 0.05 mmol), in a solvent mixture of 2:2:1 N,N-dimethylformamide/ethanol/water (10 mL) was heated to 90° C. for 1 h. The reaction was cooled to room temperature, and stirred for 16 h. The resulting suspension was poured into water (200 mL) and acidified with 1M HCl to pH 1. The solid was filtered, washed with water, dried, and purified by RP-HPLC (preparative reversed-phase high pressure liquid chromatography) using a Zorbax SB-C18 7M 21.2×250 mm column with UV detection analyzed at 220 and 254 nM (preparative method: water with 0.1% trifluoroacetic acid and $CH_3CN$ with 0.1% trifluoroacetic acid gradient 5-95% $CH_3CN$ over 30 minutes at 15 mL/min) to provide the title compound. $^1H$ NMR (300 MHz, DMSO-$d_6$) δ ppm 1.63-1.75 (m, 2 H), 1.77-1.97 (m, 4 H), 2.25-2.40 (m, 2 H), 3.67 (s, 2 H), 7.32-7.42 (m, 1 H), 7.49-7.63 (m, 4 H), 7.63-7.72 (m, 2 H), 8.02-8.11 (m, 1 H), 8.12-8.22 (m, 1 H), 8.64-8.75 (m, 1 H), 9.69 (s, 1 H), 10.68 (s, 1 H); MS (ESI) m/z 518 [M+H]$^+$.

Example 54

1-(5-(4-(4-oxa-1-azabicyclo[3.2.1]octan-5-yl)phenyl)pyridin-2-yl)-3-phenylurea

Example 54A tert-butyl 3-(4-bromphenyl)-3-hydroxypyrrolidine-1-carboxylate

To a cold (−78° C.) solution of 1,4-dibromobenzene (3.89 g, 16.49 mmol) in tetrahydrofuran (80 mL) was added n-butyllithium (10.3 mL, 16.5 mmol, 1.6 M in hexane) dropwise. After 15 minutes, a solution of tert-butyl 3-oxopyrrolidine-1-carboxylate (3.05 g, 16.49, mmol) in tetrahydrofuran (10 mL) was added over 5 minutes. The reaction continued to stir at −78 °C. for 15 minutes and was then quenched by the addition of saturated $NH_4Cl$ (150 mL) and diethyl ether (150 mL). After warming to room temperature, the layers were separated, and the aqueous was extracted with additional diethyl ether (2×100 mL). The combined organic layers were dried with anhydrous $Na_2SO_4$, filtered, and concentrated under reduced pressure. The residue was purified by MPLC (10% ethyl acetate in hexane to 50% ethyl acetate in hexane) to give the title product. MS (ESI) m/z 342 [M+H]$^+$.

Example 54B tert-butyl 3-(4-bromophenyl)-3-(2-ethoxy-2-oxoethoxy)pyrrolidine-1-carboxylate Example 51B was prepared according to the procedure described for Example 33B, substituting Example 54A for Example 33A. MS (ESI) m/z 428 [M+H]$^+$.

Example 54C tert-butyl 3-(4-bromophenyl)-3-(2-hydroxyethoxy)pyrrolidine-1-carboxylate To an ambient solution of Example 54B (0.530 g, 1.24 mmol) in methanol (5 mL) was added $NaBH_4$ (0.188 g, 4.96 mmol). The reaction was stirred for 1 h and was then quenched by the addition of water (20 mL) and ethyl acetate (20 mL). The layers were separated, and the aqueous was extracted with additional ethyl acetate (2×20 mL). The combined organic layers were dried with anhydrous $Na_2SO_4$, filtered, and Concentrated under reduced pressure to give the title compound, which was used in the subsequent step without further purification. MS (ESI) m/z 386 [M+H]$^+$.

Example 54D tert-butyl 3-(4-bromophenyl)-3-(2-(tosyloxy)ethoxy)pyrrolidine-1-carboxylate To an ambient solution of Example 54C (0.450 g, 1.17 mmol), triethylamine (0.178 mL, 1.28 mmol), and 4-dimethylaminopyridine (0.005 g, 0.041 mmol) in dichloromethane (3 mL) was added p-toluenesulfonate chloride (0.224 g, 1.17 mmol). The reaction was stirred at room temperature for 8 h and was then partitioned between water (10 mL) and diethyl ether (10 mL). The layers were separated, and the aqueous was extracted with additional diethyl ether (2×10 mL). The combined organic layers were dried with anhydrous $Na_2SO_4$, filtered, and concentrated under reduced pressure. The residue was purified by MPLC (10% ethyl acetate in hexane to 25% ethyl acetate in hexane) to give the title product. MS (ESI) m/z 541 [M+H]$^+$.

Example 54E 5-(4-bromophenyl)-4-oxa-1-azabicyclo[3.2.1]octane

To an ambient solution of Example 54D (0.100 g, 0.186 mmol) in dichloromethane (1 mL) was added trifluoroacetic acid (0.5 ml). The reaction was stirred for 0.5 h, and the solution was then carefully added to a slurry of $K_2CO_3$ (3.0 g, 21.7 mmol) 1 h dichloromethane (10 mL). After the evolution of gas ceased, the mixture was heated to 40° C. for 1 h. The mixture was cooled to room temperature and was diluted with water (10 mL). The layers were separated, and the aqueous was extracted with additional dichloromethane (2×10 mL). The combined organic layers were dried with anhydrous $Na_2SO_4$, filtered, and concentrated under reduced pressure to give the title product, which was used in the subsequent step without further purification. MS (ESI) m/z 268 [M+H]$^+$.

Example 54F 1-(5-(4-(4-oxa-1-azabicyclo[3.2.1]octan-5-yl)phenyl)pyridin-2-yl)-3-phenylurea A solution of Example 54E (0.048 g, 0.18 mmol), Example 28A (0.063 g, 0.18 mmol), CsF (0.085 g, 0.559 mmol), and tetrakis(triphenylphosphine)palladium(0) (0.020 g, 0.017 mmol) in a solvent mixture of dimethoxyethane (0.5 mL) and methanol (0.5 mL) was heated to 90° C. for 16 h. The reaction was cooled to room temperature and diluted with $H_2O$ (2 mL) and ethyl acetate (2 mL). The layers were separated, and the aqueous was extracted with additional ethyl acetate (2×2 mL). The combined organic layers were dried with anhydrous $Na_2SO_4$, filtered, and concentrated under reduced pressure. The residue was purified by RP-HPLC (preparative reversed-phase high pressure liquid chromatography) using a Zorbax SB-C18 7M 21.2×250 mm column with UV detection analyzed at 220 and 254 nM (preparative method: water with 0.1% trifluoroacetic acid and $CH_3CN$ with 0.1% trifluoroacetic acid gradient 5-95% $CH_3CN$ over 30 minutes at 15 mL/min). The fractions containing the desired product were diluted with saturated aqueous $NaHCO_3$ and extracted with ethyl acetate. The organic layer was dried with anhydrous $Na_2SO_4$, filtered and concentrated under reduced pressure to give the title compound as a white solid. $^1H$ NMR (500 MHz, DMSO-$d_6$) δ ppm 2.09-2.17 (m, 1 H), 2.27-2.38 (m, 1 H), 2.53-2.61 (m, 1 H), 2.81-2.88 (m, 1 H), 2.91-2.98 (m, 2 H), 3.02-3.09 (m, 1 H), 3.10-3.18 (m, 1 H), 3.69-3.79 (m, 1 H), 3.94-4.03 (m, 1 H), 6.99-7.07 (m, 1 H), 7.28-7.38 (m, 2 H), 7.48-7.57 (m, 4 H), 7.60-7.69 (m, 3 H), 8.02-8.12 (m, 1 H), 8.53-8.67 (m, 1 H), 9.45-9.58 (m, 1 H), 10.31-10.44 (m, 1 H); MS (ESI) m/z 401 [M+H]$^+$.

Example 55

2-(1-(3-fluoro-4-(6-(3-(3-(trifluoromethyl)phenyl)
ureido)pyridin-3-yl)phenyl)cyclopentyloxy)acetic
acid

Example 55A 1-(4-chloro-3-fluorophenyl)cyclopentanol

Example 58A was prepared according to the procedure described for Example 3A, substituting 1-bromo-3-fluoro-4-chlorobenzene for 1,4-dibromobenzene. MS (ESI) m/z 215 [M+H]$^+$.

Example 55B 2-(1-(4-chloro-3-fluorophenyl)cyclopentyloxy)acetic
acid

Example 55B was prepared according to the procedure described for Example 3B, substituting Example 55A for Example 3A. MS (ESI) m/z 273 [M+H]$^+$.

Example 55C 2-(1-(3-fluoro-4-(6-(3-(3-(trifluoromethyl)phenyl)
ureido)pyridin-3-yl)phenyl)cyclopentyloxy)acetic
acid A mixture of Example 55B (0.094 g, 0.346 mmol), Example 29A (0.141 g, 0.346 mmol), $K_3PO_4$ (0.220 g, 1.04 mmol), dicyclohexyl(2',6'-dimethoxybiphenyl-2-yl)phosphine (0.019 g, 0.046 mmol), and tris(dibenzylideneacetone)dipalladium(0) (0.011 g, 0.012 mmol) in a solvent mixture of N,N-dimethylformamide/1-butanol/$H_2O$ (2/2/1, 1 mL) was heated to 90° C. for 15 h. The solution was cooled to room temperature and diluted with 10% HCl (1 mL) and ethyl acetate (1 mL). The layers were separated, and the aqueous was extracted with additional ethyl acetate (2×2 mL). The combined organics were dried with anhydrous $Na_2SO_4$, filtered, and concentrated under reduced pressure. The residue was purified by RP-HPLC (preparative reversed-phase high pressure liquid chromatography) using a Zorbax SB-C18 7M 21.2×250 mm column with UV detection analyzed at 220 and 254 nM (preparative method: water with 0.1% trifluoroacetic acid and $CH_3CN$ with 0.1% trifluoroacetic acid gradient 5-95% $CH_3CN$ Over 30 minutes at 15 mL/min) to provide the title compound as a white solid. $^1$H NMR (300 MHz, DMSO-d$_6$) δ ppm 1.66-1.77 (m, 2 H), 1.80-1.91 (m, 4 H), 2.05-2.18 (m, 2 H), 3.69 (s, 2 H), 7.30-7.41 (m, 3 H), 7.50-7.64 (m, 2 H), 7.64-7.73 (m, 2 H), 7.94-8.03 (m, 1 H), 8.09 (s, 1 H), 8.47-8.56 (m, 1 H), 9.69 (s, 1 H), 10.65 (s, 1 H); MS (ESI) m/z 518 [M+H]$^+$.

Example 56

2-(1-(3-fluoro-4-(6-(3-(3-(trifluoromethyl)phenyl)
ureido)pyridine-3-yl)phenyl)cyclobutoxy)acetic acid

Example 56A 1-(4-chloro-3-fluorophenyl)cyclobutanol

To a cold (−78° C.) solution of 4-bromo-1-chloro-2-fluorobenzene (2.99 g, 14.27 mmol) in tetrahydrofuran (50 mL) was added n-butyllithium (5.71 mL, 14.27 mmol, 2.5 m in hexane) over 5 minutes. The reaction was stirred at −78° C. for 15 min, and cybutanone (1.0 g, 14.27 mmol) was added dropwise. After 15 minutes, the reaction mixture was quenched by the addition of saturated aqueous of $NH_4Cl$ (50 mL) and diethyl ether (50 mL). The layers were separated, and the aqueous was extracted with additional diethyl ether (2×50 mL). The combined organic layers were dried with anhydrous $Na_2SO_4$, filtered concentrated under reduced pressure. The residue was purified by RP-HPLC (preparative reversed-phase high pressure liquid Chromatography) using a Zorbax SB-C18 7M 21.2×250 mm column with UV detection analyzed at 220 and 254 nM (preparative method: water with 0.1% trifluoroacetic acid and $CH_3CN$ with 0.1% trifluoroacetic acid gradient 5-95% $CH_3CN$ over 30 minutes at 15 mL/min) to provide the title compound as a solid. MS (ESI) m/z 201 [M+H]$^+$.

Example 56B 2-(1-(4-chloro-3-fluorophenyl)cyclobutoxy)acetic
acid

TO an ambient suspension of NaH (0.341 g, 8.52 mmol, 60% dispersion in mineral oil) in N,N-dimethylformamide (7 mL) was added a solution of Example 56A (0.342 g, 1.71 mmol) in N,N-dimethylformamide (1 mL) dropwise. The reaction was stirred for 0.5 h, and 2-bromoacetic acid (0.474 g, 3.41 mmol) was added as a solution in N,N-dimethylformamide (2 mL) dropwise. The reaction was stirred at room temperature for 24 h and was then quenched by the slow addition of $H_2O$ (10 mL) and diethyl ether (15 mL). The layers were separated, and the organic discarded. The aqueous was acidified to pH ~4-5 with 10% HCl and was extracted with diethyl ether (3×15 mL). The combined organics were dried with anhydrous sodium sulfate, filtered and concentrated under reduced pressure to give a yellow oil, which was used without further purification in the subsequent step, MS (ESI)m/z 2.59 [M+H]$^+$.

Example 56C 2-(1-(3-fluoro-4-(6-(3-(3-(trifluoromethyl)phenyl)
ureido)pyridin-3-yl)phenyl)cyclobutoxy)acetic acid Example 56C was prepared according to the procedure described for Example 55C, substituting Example 56B for Example 55B. $^1$H NMR (300 MHz, DMSO-d$_6$) δ ppm 1.56-1.74 (m, 1 H), 1.84-2.01 (m, 1 H), 2.33-2.45 (m, 4 H), 3.68 (s, 2 H), 7.34-7.44 (m, 3 H), 7.52-7.64 (m, 2 H), 7.64-7.73 (m, 2 H), 7.95-8.05 (m, 1 H), 8.09 (s, 1 H), 8.52-8.57 (m, 1 H), 9.67 (s, 1 H), 10.64 (s, 1 H); MS (ESI) m/z 504 [M+H]$^+$.

Example 57

[(1-{5-[4-({[(2-fluorophenyl)amino]
carbonyl}amino)phenyl]pyridin-2-yl}cyclopentyl)
oxy]acetic acid

Example 57A 1-(5-(4-Nitrophenyl)pyridin-2-yl)cyclopentanol

To a cold (−20° C.) solution of 5-bromo-2-iodopyridine (10 g, 35.22 mmol) in tetrahydrofuran (50 mL) was added isopropylmagnesium chloride (20 mL, 38.74 mmol, 2 M solution in tetrahydrofuran) dropwise over 10 minutes. The reaction was allowed to warm to 0° C. over 1 hour and then cooled to −15° C. A solution of cyclopentanone (2.7 mL, 30 mmol) in tetrahydrofuran (25 mL) was added dropwise, and the reaction was warmed to 15° C. over 3 hours. The reaction was then quenched by the dropwise addition of saturated aqueous NH$_4$Cl. The layers were separated, and the aqueous was extracted with ethyl acetate (3×30 mL). The combined organic layers were washed with water, brine, dried with anhydrous MgSO$_4$, filtered and concentrated under reduced pressure to provide a crude alcohol, which was used in the subsequent step without further purification.

A mixture of the crude alcohol (1.05 g, 4.34 mmol), 4-nitrophenyl boronic acid pinacol ester (1.4 g, 5.64 mmol), potassium fluoride (0.76 g, 13 mmol) and tetrakis(triphenylphosphine) palladium (0.87 g, 0.43 mmol) in a solvent mixture (dimethoxyemane:ethanol:water:toluene, 10:6:3:1,50 mL) was heated to 9.0° C. for 10 hours. The reaction was cooled to room temperature, diluted with water, and extracted with ethyl acetate (3×50 mL). The combined of organic layers were washed with water, brine, dried with anhydrous MgSO$_4$, filtered and concentrated under reduced pressure. The residue was purified by chromatography on SiO$_2$ (30% ethyl acetate in hexane) to afford the title compound. $^1$H NMR (300 MHz, DMSO-d$_6$) δ ppm 1.70-1.82 (m, 4 H), 1.84-1.93 (m, 2 H), 2.08-2.18 (m, 2 H), 5.15 (s, 1 H), 7.81 (m, 1 H), 8.02 (m, 2 H), 8.17 (m, 1 H), 8.32 (m, 2 H), 8.91 (m, 1 H).

Example 57B

Methyl 2-(1-(5-(4-nitrophenyl)pyridin-2-yl)cyclopentyloxy)acetate

To an ambient suspension of sodium hydride (0.2 g, 60% suspension in mineral oil, 4.85 mmol) in N,N-dimethylformamide (3 mL) was added a solution of Example 57A (0.46 g, 1.6 mmol) in N,N-dimethylformamide (4 mL) at room temperature. After 20 minutes, allyl bromide (0.42 mL, 4.85 mmol) was added, and the reaction was stirred at room temperature for 3 hours. The reaction was then quenched by the addition of saturated aqueous NH$_4$Cl. The layers were separated, and the aqueous was extracted with ethyl acetate (3×50 mL). The combined organic layers were washed with water, brine, dried with anhydrous MgSO$_4$, filtered and concentrated under reduced pressure to provide a crude allyl ether, which was used in the next step without further purification.

The crude product from the previous step was dissolved in glacial acetic acid (20 mL) and added to a cold (0° C.) solution of potassium permanganate (1 g, 6.44 mmol) in water (20 mL). The reaction was warmed to room temperature over 20 minutes and was then quenched by the addition of benzene (25 mL) and solid sodium sulfite (15 g). The biphasic mixture was acidified to pH 3 by the addition of 3N HCl and extracted with ethyl acetate (3×50 mL). The combined organic layers were washed with water, brine, dried with anhydrous MgSO$_4$, filtered and concentrated under reduced pressure to provide a crude acid, which was used in the next step without further purification.

The crude acid was dissolved in benzene (25 mL) and methanol (15 mL), and a solution of (trimethylsilyl)diazomethane (1.61 mL, 2M solution in hexanes) was added dropwise at room temperature over 10 minutes. The reaction was then quenched by the drop wise addition of acetic acid, and the solvents were removed under reduced pressure. The residue was treated with saturated aqueous sodium bicarbonate and extracted with ethyl acetate (3×30 mL). The combined organic layers were washed with water, brine, dried with anhydrous MgSO$_4$, filtered and concentrated under reduced pressure. The residue was purified by chromatography on SiO$_2$ (30% ethyl acetate in hexane) to afford the title compound as an oil, $^1$H NMR (400 MHz, DMSO-d$_6$) δ ppm 1.70-1.79 (m, 2 H), 1.81-1.91 (m, 2 H), 2.03-2.15 (m, 4 H), 3.62 (s, 3 H), 3.91 (s, 2 H), 7.69 (m, 1 H), 8.05 (m, 2 H), 8.24 (m, 1 H), 8.33 (m, 2 H), 8.97 (broad s, 1 H); MS (ESI) m/z 357 [M+H]$^+$.

Example 57C

[(1-{5-[4-({[(2-fluorophenyl)amino]carbonyl}amino)phenyl]pyridin-2-yl}cyclopentyl)oxy]acetic acid A suspension of Example 57B (0.15 g, 0.42 mmol), iron powder (0.047 g, 0.84 mmol) and ammonium chloride (0.026 g, 0.46 mmol) in ethanol (10 mL) and water (5 mL) was heated to reflux for 1 h. The reaction was cooled and filtered through a pad of wet celite. The filtrate was diluted with ethyl acetate, and the layers were separated. The combined organic layers were washed with water, brine, dried with anhydrous MgSO$_4$, filtered and concentrated under reduced pressure to provide a crude ester, which was used in the next step without further purification.

To an ambient solution of the crude ester (0.05 g, 0.15 mmol) from the previous step in tetrahydrofuran (5 mL) was added 2-fluorophenyl isocyanate (0.034 mL, 0.3 mmol). The reaction was stirred at room temperature for 15 hours, diluted with water and extracted with ethyl acetate (3×25 mL). The combined organic layers were washed with water, brine, dried with anhydrous MgSO$_4$ filtered and concentrated under reduced pressure to provide a residue, which was used in the next step without further, purification.

Lithium hydroxide monohydrate (0.02 g) was added to the solution of the crude product in tetrahydrofuran (10 mL) and water (5 mL) and stirred at room temperature for 12 hours. The reaction was acidified (pH 1) by the addition of 3N HCl and extracted with ethyl acetate (3×25 mL). The combined organic layers were washed with water, brine, dried with anhydrous MgSO$_4$, filtered and concentrated under-reduced pressure to provide a yellow solid. This solid was recrystallized using methanol/ethylacetate to afford the title Compound as a pale yellow solid. $^1$H NMR (400 MHz, DMSO-d$_6$) δ ppm 1.68-1.78 (m, 2 H), 1.81-1.90 (m, 2 H), 2.01-2.15 (m, 4 H), 3.77 (s, 2 H), 7.00-7.04 (m, 1 H), 7.15 (m, 1 H), 7.24 (m, 1 H), 7.59 (d, J=8.55 Hz, 2 H), 7.62 (m, 1 H), 7.70 (m, 2 H), 8.07 (m, 1 H), 8.16 (m, 1 H), 8.60 (m, 1 H), 8.81 (m, 1 H), 12.62 (broad s, 1 H); MS (ESI) m/z 450.1 [M+H]$^+$.

Example 58

[1-(4-{6-[({[3-(trifluoromethyl)phenyl]amino}carbonyl)amino]pyridin-3-yl}phenyl)cyclopentyl]acetic acid Example 58A ethyl 2-cyano-2-cyclopentylideneacetate To an ambient solution of hexamethyldisilazane (17.7 mL, 84.0 mmol) in acetic acid (56 mL) was added sequentially cyclopentanone (5.0 mL, 56.3 mmol) and ethyl 2-cyanoacetate (12.0 mL, 113 mmol). The solution was heated to 70° C. for 15 hours. The reaction was cooled to room temperature and diluted with water (100 mL) and ethyl acetate (100 mL). The layers were separated, and the aqueous was extracted with additional ethyl acetate (2×100 mL). The combined organics were dried with anhydrous Na$_2$SO$_4$, filtered, and concentrated under reduced pressure. The residue was purified by chromatography on SiO$_2$ gel, eluting with 100% hexane to 5% ethyl acetate in hexane, to give the title product as a white, solid. MS (ESI) m/z 180 [M+H]$^+$.

Example 58B 2-(1-(4-chlorophenyl)cyclopentyl)-2-cyanoacetic acid

To an ambient suspension of magnesium turnings (0.43 g, 17.7 mmol) in tetrahydrofuran (20 mL) was added 4-bromo-1-chloro-benzene (0.4 g, 2.08 mmol) and a few crystals of iodine. The reaction was gently warmed with a heat gun. After the purple color dissipated, the remainder of the 4-bromo-1-chloro-benzene (2.0 g, 15.6 mmol) was added to the reaction dropwise as a solution in tetrahydrofuran (20 mL) at such a rate to maintain a gentle reflux. After 1 h, the solution of the Grignard of 4-bromo-1-Chloro-benzene was cooled to ambient temperature and added dropwise to a cold (0° C.) mixture of CuI (0.237 g, 1.24 mmol) and Example 58A (3.18 g, 17.7 mmol) in tetrahydrofuran (20 mL). The reaction was stirred at 0° C. for 0.5 h. The cooling bath was removed, and the reaction was stirred at ambient temperature for 15 h. The reaction was then quenched by the addition of saturated aqueous NH$_4$Cl (100 mL) and ethyl acetate (100 mL). The layers were separated, and the aqueous was extracted with additional ethyl acetate (2×50 mL). The combined organic layers were dried with anhydrous Na$_2$SO$_4$, filtered and concentrated under reduced pressure. The residue was purified by chromatography on SiO$_2$ gel, eluting with 100% hexane to 10% ethyl acetate in hexane, to give the title compound. MS (ESI) m/z 293 [M+H]$^+$.

Example 58C 2-(1-(4-chlorophenyl)cyclopentyl)acetic acid

Example 58B (3.0 g, 10.3 mmol) was dissolved in a 15% w/w solution of KOH in ethylene glycol (50 mL) and heated to 190° C. for 4 hours. The reaction was cooled to room temperature; diluted with water (100 mL), and the pH adjusted to ~3 with concentrated HCl. The aqueous was extracted with dichloromethane (3×50 mL). The combined organic layers were dried with anhydrous Na$_2$SO$_4$, filtered and concentrated under reduced pressure. The residue was purified by RP-HPLC (preparative reversed-phase high pressure liquid chromatography) using a Zorbax SB-C18 7M 21.2×250 mm column with UV detection analyzed at 220 and 254 nM (preparative method: water with 0.1% trifluoroacetic acid and CH$_3$CN with 0.1% trifluoroacetic acid gradient 5-95% CH$_3$CN over 30 minutes at 15 mL/min) to give the title compound as a beije solid. MS (ESI) m/z 238 [M–H]$^-$.

Example 58D

[1-(4-{6-[({[3-(trifluoromethyl)phenyl]
amino}carbonyl)amino]pyridin-3-yl}phenyl)cyclopentyl]acetic acid Example 58D was prepared according to the procedure described for Example 55C, substituting Example 58C for Example 55B. $^1$H NMR (300 MHz, DMSO-d$_6$) δ ppm 1.52-1.84 (m, 4 H), 1.85-2.14 (m, 4 H), 2.56-2.67 (m, 2 H), 7.35-7.51 (m, 3 H), 7.53-7.65 (m, 3 H), 7.67-7.73 (m, 1 H), 7.76-7.85 (m, 1 H), 8.05-8.16 (m, 2 H), 8.63 (m, 1 H), 9.56-9.68 (m, 1 H), 10.66-10.81 (m, 1 H), 11.80 (s, 1 H); MS (ESI) m/z 484 [M+H]$^+$.

Example 59

(1-{4-[6-({[(2-fluorophenyl)amino]carbonyl}amino)
pyridin-3-yl]phenyl}cyclopentyl)acetic acid Example 59A 1-(2-fluorophenyl)-3-(5-(4,4,5,5-tetramethyl-1,3,2-
dioxaborolan-2-yl)pyridin-2-yl)urea Example 59A was prepared according to the procedure described for Example 28A, substituting 2-fluorophenyl isocyanate for phenyl isocyanate. MS (ESI) m/z 358 [M+H]$^+$.

Example 59B (1-{4-[6-({[(2-fluorophenyl)amino]carbonyl}amino)
pyridin-3-yl]phenyl}cyclopentyl)acetic acid Example 59B was prepared according to the procedure described for Example 55C, substituting Example 58C for Example 55B and substituting Example 59A for Example 29A. $^1$H NMR (300 MHz, DMSO-d$_6$) δ ppm 1.46-1.83 (m, 4 H), 1.85-2.11 (m, 4 H), 2.54-2.69 (m, 2 H), 7.00-7.11 (m, 1 H), 7.17 (m, 1 H), 7.23-7.32 (m, 1 H), 7.43 (m, 2 H), 7.54 (m, 1 H), 7.61 (m, 2 H) 8.09 (m, 1 H) 8.16-8.33 (m, 1 H), 8.58 (m, 1 H), 9.89 (s, 1 H), 10.76 (s, 1 H), 11.82 (s, 1 H); MS (ESI) m/z 434 [M+H]$^+$.

Compound 60

{[1-(2-fluoro-4-{6-[({[3-(trifluoromethyl)phenyl]
amino}carbonyl)amino]pyridin-3-yl}phenyl)cyclobutyl]oxy}acetic acid Example 60A 1-(4-bromo-2-fluorophenyl)cyclobutanol A 100 mL 3-neck round bottom flask was charged with 4-bromo-2-fluoro-1-iodobenzene (1000 mg, 3.32 mmol) and diethyl ether (30 mL). The solution was cooled to −78 °C., and n-butyllithium (1.329 mL, 3.32 mmol) was added dropwise, keeping the temperature below −68° C. After stirring for 15 min, cyclobutanone (0.249 mL, 3.32 mmol) was added dropwise, keeping temperature; below −68° C. The solution was stirred at −78° C. for 15 min. The reaction was then quenched by the addition of saturated ammonium chloride (25 mL). The layers were separated, and the organic was washed with water (1×10 mL) and brine (1×10 mL). The organic layer was dried with anhydrous sodium sulfate and concentrated under reduced pressure. The residue was purified by flash chromatography (SiO$_2$ gel), eluting with 3% ethylacetate/hexanes to give the desired product. $^1$H NMR (300 MHz, DMSO-d$_6$) δ ppm 1.55-1.69 (m, 1 H), 1.91-2.05 (m, 1 H), 2.19-2.28 (m, 2 H), 2.46-2.55 (m, 2 H), 5.59 (s, 1 H), 7.33-7.40 (m, 2 H), 7.44-7.48 (m, 2 H).

Example 60B

{[1-(4-bromo-2-fluorophenyl)cyclobutyl]oxy}acetic acid

A 50 mL round-bottomed flask was charged with NaH (361 mg, 9.04 mmol) and N,N-dimethylacetamide (5 mL). A solution of the product from Example 60A (443 mg; 1.808 mmol) in N,N-dimethylacetamide (5 mL) was added dropwise, and the reaction was stirred at 22° C. for 30 min. A solution of 2-bromoacetic acid (502 mg, 3.62 mmol) in N,N-dimethylacetamide (5 mL) was added dropwise. The reaction was stirred at 22° C. for 16 hours and was then quenched by the slow addition of water (15 mL). The aqueous was extracted with 1:1 diethyl ether/hexanes (2×20 mL), and the organics discarded. The aqueous layer was acidified to pH 1 with 1M HCl and extracted with ethyl acetate (2×75 mL). The combined organics were washed with water (4×20 mL) and brine (1×20 mL), dried with anhydrous sodium sulfate, filtered, and concentrated under reduced pressure to give the title product. $^1$H NMR (300 MHz, DMSO-$d_6$) δ ppm 1.54-1.70 (m, 1 H), 1.91-2.10 (m, 1 H), 2.34-2.47 (m, 4 H), 3.65 (s, 2 H), 7.34-7.43 (m, 2 H), 7.49-7.53 (m, 1 H), 12.45 (s, 1 H).

Example 60C

N-[5-(4,4,5,5-tetramethyl-1,3,2-dioxaborolan-2-yl)pyridin-2-yl]-N'-[3-(trifluoromethyl)phenyl]urea To an ambient solution of 5-(4,4,5,5-tetramethyl-1,3,2-dioxaborolan-2-yl)pyridin-2-amine (0.350 g, 1.59 mmol) in tetrahydrofuran (4 mL) was added 3-trifluoromethylphenyl isocyanate (1.59 mmol). The solution was stirred at room temperature for 1 hour and was then concentrated under reduced pressure. The solid was washed with diethyl ether (2 mL) and air-dried to give the title compound MS (ESI) m/z 408 [M+H]$^+$.

Example 60D

{[1-(2-fluoro-4-{6-[({[3-(trifluoromethyl)phenyl]amino}carbonyl)amino]pyridin-3-yl}phenyl)cyclobutyl]oxy}acetic acid A 25 mL vial was charged with the product from Example 60C (459 mg, 1.128 mmol), the product from Example 60B (342 mg, 1.128 mmol), dibasic potassium phosphate (590 mg, 3.38 mmol), and 1,1'-bis(di-tert-butylphosphino)ferrocene palladium (II) dichloride (7.38 mg, 0.011 mmol), N,N-dimethylacetamide (4 mL), ethanol (4.00 ml) and water (2 mL). The suspension was stirred and heated to 90° C., whereupon the reaction became homogenous. After heating at 90° C. for 1 hour; the reaction was cooled to room temperature. The resulting suspension was poured into water (200 mL). The mixture was acidified to pH 1 with 1 M HCl. The solid was filtered, washed with water, and air-dried to give the title product. $^1$H NMR (300 MHz, DMSO-$d_6$) δ ppm 1.62-1.71 (m, 1 H), 1.96-2.07 (m, 1 H), 2.39-2.49 (m, 4 H), 3.69 (s, 2 H), 7.38 (d, J=7.12Hz, 1 H), 7.47-7.61 (m, 4 H), 7.65-7.71 (m, 2 H), 8.07 (s, 1 H), 8.17 (dd, J=2.7 and 8.8 Hz, 1 H), 8.71 (d, J=2.7 Hz, 1 H), 9.68 (s, 1 H), 10.65 (s, 1 H), 12.5 (br s, 1 H). MS (ESI) m/z 504 [M+H]$^+$.

Example 61

[(1-{2-fluoro-4-[6-({[3-(trifluoromethyl)phenyl]acetyl}amino)pyridin-3-yl]phenyl}cyclobutyl)oxy]acetic acid Example 61A 6-({[3-(trifluoromethyl)phenyl]acetyl}amino)pyridin-3-ylboronic acid A 250 mL round-bottomed flask was charged with 2-(3-(trifluoromethyl)phenyl)acetic acid (2.319 g, 11.36 mmol), 5-(4,4,5,5-tetramethyl-1,3,2-dioxaborolan-2-yl)pyridin-2-amine (2.5 g, 11.36 mmol), 1-ethyl-3-[3-(dimethylamino)propyl]-carbodiimide hydrochloride (2.178 g, 11.36 mmol), 1-hydroxybenzotriazole hydrate (1.740 g, 11.36 mmol), N-methylmorpholine (5.00 mL, 45.4 mmol) and N,N-dimethylacetamide (50 mL). The reaction was stirred at 50 °C. for 16 hours. The reaction was then quenched by the addition of ethyl acetate (50 mL) and water (50 mL). The layers were separated, and the organic was Washed with water (3×50 mL) and brine (1×50 mL). The organic was dried with anhydrous sodium sulfate and concentrated under reduced pressure. The residue was purified by reverse-phase HPLC using a 15% water (0.1% trifluoroacetic acid) to 95% acetonitrile (0.1% trifluoroacetic acid) gradient to give the boronic acid as a white solid. $^1$H NMR (300 MHz, DMSO-$d_6$) δ ppm 3.88 (s, 2 H), 7.54-7.66 (m, 3 H), 7.72 (s, 1 H), 7.96 (d, J=8.5 Hz, 1 H), 8.12 (dd, J=1.7 and 8.1 Hz, 1 H), 8.4 (br s, 1 H), 10.94 (s, 1 H).

Example 61B

[(1-{2-fluoro-4-[6-({[3-(trifluoromethyl)phenyl]acetyl}amino)pyridin-3-yl]phenyl}cyclobutyl)oxy]acetic acid A 4 mL vial was charged with the product from Example 61A (17.7 mg, 0.055 mmol) and the product from Example 60B (16.56 mg, 0.055 mmol), dibasic potassium phosphate (28.5 mg, 0.164 mmol), 1,1'-bis(di-tert-butylphosphino)ferrocene palladium (II) dichloride (0.357 mg, 0.546 μmol), N,N-dimethylacetamide (1 ml), ethanol (1.000 mL), and water (0.500 mL). The suspension was stirred and heated to 90° C., whereupon the reaction became homogenous. After heating at 90° C. for 1 hour, the reaction was cooled to room temperature. The reaction was then partitioned between with ethyl acetate (2 mL) and water (2 mL). The layers were separated, and the organic was dried over anhydrous sodium sulfate, filtered, and concentrated under reduced pressure. The residue was purified by reverse-phase HPLC (mobile phase: 10%-100% acetonitrile in 0.1% trifluoroacetic acid aqueous solution during 60 min, C18 column) to give the title product, $^1$H NMR (300 MHz, DMSO-$d_6$) δ ppm 1.59-1.72 (m, 1 H), 1.95-2.07 (m, 1 H), 2.38-2.45 (m, 4 H), 3.65 (s, 2 H), 3.89 (s, 2 H), 7.46-7.52 (m, 1 H), 7.55-7.67 (m, 5 H), 7.73 (s, 1 H), 8.11-8.18 (m, 2 H), 8.73 (br s, 1 H), 10.94 (s, 1 H). MS (ESI) m/z 503 [M+H]$^+$.

It is understood that the foregoing detailed description and accompanying examples are merely illustrative and are not to be taken as limitations upon the scope of the invention. Various, changes and modifications including, but not limited to, those relating to the chemical structures, substituents, derivatives, intermediates, syntheses, formulations and/or methods of use of the invention, can be made without departing from the spirit of the present invention and scope thereof.

We claim:

1. A method for treating a disorder selected from the group consisting of type 2 diabetes, obesity, elevated plasma triglycerides, metabolic syndrome, non-alcoholic steatohepatitis, and non-alcoholic fatty liver disease, said method comprising the step of administering to a subject in need thereof a compound of formula (I),

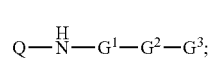

(I)

or a pharmaceutically acceptable salt, prodrug, salt of a prodrug, or a combination thereof, wherein:
$G^1$ is phenyl or monocyclic heteroaryl, each of which is optionally further substituted with 1, 2, 3, or 4 substituents as represented by T;

G² is phenyl or monocyclic heteroaryl, each of which is optionally further substituted with 1, 2, 3, or 4 substituents as represented by T, wherein the monocyclic heteroaryl is furanyl, imidazolyl, isoxazolyl, isothiazolyl, oxadiazolyl, 1,3-oxazolyl, pyridinyl, pyridazinyl, pyrimidinyl, pyrazinyl, pyrazolyl, pyrrolyl, tetrazolyl, thiadiazolyl, 1,3-thiazolyl, triazolyl, or triazinyl;

T, at each occurrence, is independently selected from the group consisting of alkyl, alkenyl, alkynyl, halogen, —CN, —NO₂, —OR¹, —OC(O)(R²), —N(Rʷ)(R¹), —N(Rʷ)—C(O)(R¹), —N(Rʷ)—C(O)O(R¹), —N(Rʷ)—C(O)N(Rʷ)(R¹), —N(Rʷ)—S(O)₂(R²), —C(O)O(R¹), —C(O)N(Rʷ)(R¹), —C(O)R¹, —SR¹, —S(O)R², —S(O)₂R², —S(O)₂N(Rʷ)(R¹), —(CRᵃRᵇ)ᵣ—CN, —(CRᵃRᵇ)ᵣ—NO₂, —(CRᵃRᵇ)ᵣ—OR¹, —(CRᵃRᵇ)ᵣ—OC(O)(R²), —(CRᵃRᵇ)ᵣ—N(Rʷ)(R¹), —(CRᵃRᵇ)ᵣ—N(Rʷ)C(O)(R¹), —(CRᵃRᵇ)ᵣ—N(Rʷ)—C(O)O(R¹), —(CRᵃRᵇ)ᵣ—N(Rʷ)—C(O)N(Rʷ)(R¹), —(CRᵃRᵇ)ᵣ—N(Rʷ)—S(O)₂(R²), —(CRᵃRᵇ)ᵣ—C(O)O(R¹), —(CRᵃRᵇ)ᵣ—C(O)N(Rʷ)(R¹), —(CRᵃRᵇ)ᵣ—C(O)R¹, —(CRᵃRᵇ)ᵣSR¹, —(CRᵃRᵇ)ᵣ—S(O)R², —(CRᵃRᵇ)ᵣS(O)₂R², —(CRᵃRᵇ)ᵣ—S(O)₂N(Rʷ)(R¹), and haloalkyl; or two of the adjacent substituents T, together with the carbon atoms to which they are attached, form a monocyclic ring selected from the group consisting of phenyl, heterocycle and heteroaryl, wherein each ring is optionally further substituted with 1, 2 or 3 substituents selected from the group consisting of oxo, alkyl, alkenyl, alkynyl, halogen, —CN, —NO₂, —OR¹, —OC(O)(R²), —N(Rʷ)(R¹), —N(Rʷ)C(O)(R¹), —N(Rʷ)—C(O)O (R¹), —N(Rʷ)—C(O)N(Rʷ)(R¹), —N(Rʷ)—S(O)₂ (R²), —C(O)O(R¹), —C(O)N(Rʷ)(R¹), —C(O)R¹, —SR¹, —S(O)R², —S(O)₂R², —S(O)₂N(Rʷ)(R¹), —(CRᵃRᵇ)ᵣ—CN, —(CRᵃRᵇ)ᵣ—NO₂, —(CRᵍRʰ)ᵣ—OR¹, —(CRᵃRᵇ)ᵣ—OC(O)(R²), —(CRᵃRᵇ)ᵣ—N(Rʷ)(R¹), —(CRᵃRᵇ)ᵣ—N(Rʷ)C(O)(R¹), —(CRᵃRᵇ)ᵣ—N(Rʷ)—C(O)O(R¹), —(CRᵃRᵇ)ᵣ—N(Rʷ)—C(O)N(Rʷ)(R¹), —(CRᵃRᵇ)ᵣ—N(Rʷ)—S(O)₂(R²), —(CRᵃRᵇ)ᵣ—C(O)O(R¹), —(CRᵃRᵇ)ᵣ—C(O)N(Rʷ)(R¹), —(CRᵃRᵇ)ᵣ—C(O)R¹, —(CRᵃRᵇ)ᵣSR¹, —(CRᵃRᵇ)ᵣ—S(O)R², —(CRᵃRᵇ)ᵣ—S(O)₂R², —(CRᵃRᵇ)ᵣ—S(O)₂N(Rʷ) (R¹), and haloalkyl;

G³ is formula (a) or formula (b)

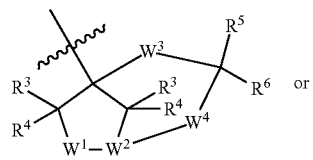

(a)

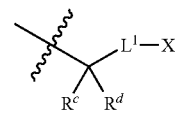

(b)

W¹ is —C(R³)(R⁴)— or —C(R³)(R⁴)—C(R³)(R⁴)—, and W² is —C(R⁷)— of N; or

W¹ is N(H), N(alkyl), O, S(O), or S(O)₂, and W² is —C(R⁷)—;

W³ is N(H), N(alkyl), or O;

W⁴ is —C(R³)(R⁴)— or —C(R³)(R⁴)—C(R³)(R⁴)—;

R³ and R⁴, at each occurrence, are independently hydrogen or $C_{1-6}$ alkyl;

R⁵ and R⁶ are independently hydrogen or $C_{1-6}$ alkyl; or R⁵ and R⁶, together with the carbon to which they are attached, is C(=O);

R⁷, at each occurrence, is independently hydrogen, $C_{1-6}$ alkyl or —C(O)OH;

Rᶜ and Rᵈ, together with the carbon atom to which they are attached, is a 3- to 6-membered cycloalkyl or a monocyclic heterocycle of formula (c);

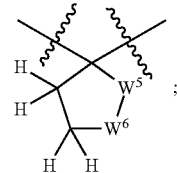

(c)

wherein 1, 2, 3, or 4 hydrogen atoms attached to the ring carbon of the cycloalkyl and the monocyclic heterocycle are optionally replaced with radicals selected from the group consisting of alkyl, halogen, —CN, haloalkyl, —C(O)O(R⁸), —C(O)N(R⁸)(R⁹), —(CRᵉRᶠ)ₜ—C(O)O (R⁸), and —(CRᵉRᶠ)ₜ—C(O)N(R⁸)(R⁹);

W⁵ is —CH₂— or —CH₂—CH₂—;

W⁶ is O, S, S(O), S(O)₂, N(Rˣ), —C(O)N(Rʸ)— or —N(Rʸ)C(O)—; wherein Rˣ is hydrogen, alkyl, haloalkyl, cycloalkyl, cycloalkenyl, aryl, heteroaryl, heterocycle, cycloalkylalkyl, cycloalkenylalkyl, arylalkyl, heteroarylalkyl, heterocyclealkyl, —C(O)O(Rᶻ), —C(O)Rᶻ, or —C(O)N(Rʷ)(Rᵐ);

Rʸ and Rᵐ, at each occurrence, are each independently hydrogen, alkyl, haloalkyl, aryl, cycloalkyl, cycloalkenyl, heteroaryl, heterocycle, arylalkyl, cycloalkylalkyl, cycloalkenylalkyl, heteroarylalkyl or heterocyclealkyl;

Rᶻ, at each occurrence, is independently alkyl, haloalkyl, aryl, cycloalkyl, cycloalkenyl, heteroaryl, heterocycle, arylalkyl, cycloalkylalkyl, cycloalkenylalkyl, heteroarylalkyl, or heterocyclealkyl;

R⁸ and R⁹, at each occurrence, are independently hydrogen, alkyl, aryl, cycloalkyl, cycloalkenyl, heteroaryl, heterocycle, haloalkyl, arylalkyl, cycloalkylalkyl, cycloalkenylalkyl, heteroarylalkyl, or heterocyclealkyl; or R⁸ and R⁹, together with the nitrogen atom to which they are attached, form a heterocycle ring, optionally further substituted with 1, 2 or 3 substituents selected from the group consisting of alkyl, halogen, and haloalkyl;

L¹ is O, N(H), or N(alkyl); and X is —(CRᵍRʰ)ᵤ-tetrazolyl, heterocyclealkyl, heteroarylalkyl, hydrogen, alkyl, haloalkyl, —C(O)O(R¹⁰), —C(O)N(R¹⁰)(R¹¹), —(CRᵍRʰ)ᵤ—OR¹⁰, —(CRᵍRʰ)ᵤ—N(R¹⁰)(R¹¹), —(CRᵍRʰ)ᵤ—CN, —(CRᵍRʰ)ᵤ—C(O)O(R¹⁰), or —(CRᵍRʰ)ᵤ—C(O)N (R¹⁰)(R¹¹); or L¹ is —(CRᵖRᵠ)ₛ— and X is —C(O)OH or tetrazolyl;

R¹⁰ and R¹¹, at each occurrence, are independently hydrogen, alkyl, cycloalkyl, cycloalkenyl, heteroaryl, aryl, heterocycle, cycloalkylalkyl, cycloalkenylalkyl, heteroarylalkyl, arylalkyl, heterocyclealkyl, or haloalkyl; or R¹⁰ and R¹¹, together with the nitrogen atom to which they are attached, form a heterocycle ring which is optionally further substituted with 1, 2 or 3 substituents selected from the group consisting of alkyl, halogen and haloalkyl;

Q is alkyl, alkenyl, alkynyl, haloalkyl, G$^4$, —Y$^1$—Y$^3$, or —Y$^1$—(CR$^j$R$^k$)$_v$—Y$^2$—Y$^4$; or Q is formula (d)

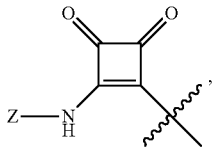

wherein
Z is alkyl, alkenyl, alkynyl, haloalkyl, G$^4$, Y$^1$—Y$^3$, or —Y$^1$—(CR$^j$R$^k$)$_v$—Y$^2$—Y$^4$; G$^4$ is cycloalkyl, cycloalkenyl, heterocycle, heteroaryl, aryl, cycloalkylalkyl, cycloalkenylalkyl, heterocyclealkyl, heteroarylalkyl, of arylalkyl;
Y$^1$, at each occurrence, is independently —C(O)—, —C(O)O—, —C(O)N(R$^w$)—, —S(O)$_2$—, —S(O)$_2$—N(R$^w$)—, wherein the right side of the —C(O)O—, —C(O)N(R$^w$)—, and —S(O)$_2$—N(R$^w$)—moieties are attached to Y$^3$ or (CR$^j$R$^k$)$_v$;
Y$^2$ at each occurrence is independently O, N(R$^w$), or C(O);
Y$^3$ at each occurrence is independently alkyl, haloalkyl, cycloalkyl, cycloalkenyl, heterocycle, heteroaryl, aryl, cycloalkylalkyl, cycloalkenylalkyl, heterocyclealkyl, heteroarylalkyl or arylalkyl;
Y$^4$ at each occurrence is independently hydrogen, alkyl, haloalkyl, cycloalkyl, cycloalkenyl, heterocycle, heteroaryl, aryl, cycloalkylalkyl, cycloalkenylalkyl, heterocyclealkyl, heteroarylalkyl, or arylalkyl;
wherein the cycloalkenyl, cycloalkyl, heterocycle, heteroaryl, aryl, the aryl moiety of the arylalkyl, the heteroaryl moiety of the heteroarylalkyl, the cycloalkyl moiety of the cycloalkylalkyl, the heterocycle moiety of the heterocyclealkylalkyl, and the cycloalkenyl moiety of the cycloalkenylalkyl as represented by X, G$^4$, Y$^3$, Y$^4$, R$^x$, R$^y$, R$^z$, R$^m$, R$^8$, R$^9$, R$^{10}$, and R$^{11}$, are each optionally further substituted with 1, 2, 3, 4 or 5 substituents selected from the group consisting of alkyl, alkenyl, alkynyl, halogen, oxo, ethylenedioxy, methylenedioxy, —CN, —NO$_2$, —OR$^1$, —OC(O)(R$^2$), —N(R$^w$)(R$^1$), —N(R$^w$)C(O)(R$^1$), —N(R$^w$)—C(O)O(R$^1$), —N(R$^w$)—C(O)N(R$^w$)(R$^1$), —N(R$^w$)—S(O)$_2$(R$^2$), —C(O)O(R$^1$), —C(O)N(R$^w$)(R$^1$), —C(O)R$^1$, —SR$^1$, —S(O)R$^2$, —S(O)$_2$R$^2$, —S(O)$_2$N(R$^w$)(R$^1$), haloalkyl, —(CR$^a$R$^b$)$_r$—CN, —(CR$^a$R$^b$)$_r$—NO$_2$, —(CR$^a$R$^b$)$_r$—OR$^1$, —(CR$^a$R$^b$)$_r$—OC(O)(R$^2$), —(CR$^a$R$^b$)$_r$—N(R$^w$)(R$^1$), —(CR$^a$R$^b$)$_r$—N(R$^w$)C(O)(R$^1$), —(CR$^a$R$^b$)$_r$—N(R$^w$)—C(O)O(R$^1$), —(CR$^a$R$^b$)$_r$N(R$^w$)—C(O)N(R$^w$)(R$^1$), —(CR$^a$R$^b$)$_r$—N(R$^w$)—S(O)$_2$(R$^2$), —(CR$^a$R$^b$)$_r$C(O)O(R$^1$), —(CR$^a$R$^b$)$_r$—C(O)N(R$^w$)(R$^1$), —(CR$^a$R$^b$)$_r$—C(O)R$^1$, —(CR$^a$R$^b$)$_r$—SR$^1$, —(CR$^a$R$^b$)$_r$—S(O)R$^2$, —(CR$^a$R$^b$)$_r$—S(O)$_2$R$^2$, —(CR$^a$R$^b$)$_r$—S(O)$_2$N(R$^w$)(R$^1$), and haloalkyl;
R$^a$, R$^b$, R$^e$, R$^f$, R$^g$, R$^h$, R$^j$, R$^k$, R$^p$, and R$^q$, at each occurrence, are independently hydrogen, halogen, alkyl, or haloalkyl;
R$^1$ and R$^w$, at each occurrence, are independently hydrogen, alkyl, or haloalkyl;
R$^2$, at each occurrence, is independently alkyl or haloalkyl; and
r, s, t, u, and v, at each occurrence, is independently 1, 2, 3, 4, 5 or 6.

2. The method of claim 1 further comprising the step of co-administering with one or more pharmaceutical agents selected from the group consisting of DPPIV inhibitor, incretin mimetic, metformin, fenofibrate, rimonabant, sibutramine, orlistat, nicotinic acid, and a statin.

3. The method of claim 1, wherein the compound is a compound of formula (II),

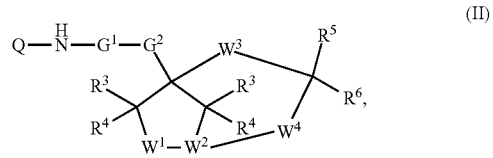

or a pharmaceutically acceptable salt, prodrug, salt of a prodrug, or a combination thereof.

4. The method of claim 3, wherein W$^2$ is N, or a pharmaceutically acceptable salt, prodrug, salt of a prodrug, or a combination thereof.

5. The method of claim 1, wherein the compound is a compound of formula (III),

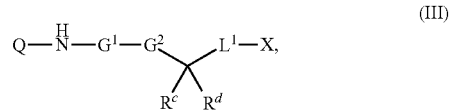

or a pharmaceutically acceptable salt, prodrug, salt of a prodrug, or a combination thereof.

6. The method of claim 5, wherein L$^1$ is O and X is hydrogen or alkyl, or a pharmaceutically acceptable salt, prodrug, salt of a prodrug, or a combination thereof.

7. The method of claim 5, wherein L$^1$ is O and X is —(CR$^g$R$^h$)$_u$—C(O)O(R$^{10}$), or a pharmaceutically acceptable salt, prodrug, salt of a prodrug, or a combination thereof.

8. The method of claim 7, wherein R$^g$ and R$^d$ are each independently hydrogen or alkyl, u is 1 and R$^{10}$ is hydrogen, or a pharmaceutically acceptable salt, prodrug, salt of a prodrug or a combination thereof.

9. The method of claim 7, wherein R$^c$ and R$^d$, together with the carbon atom to which they are attached, is a 3-6 membered cycloalkyl wherein 1, 2, 3, or 4 hydrogen atoms attached to the ring carbon of the cycloalkyl ring are optionally replaced with radicals selected from the group consisting of alkyl, halogen, —CN, haloalkyl, —C(O)O(R$^8$), —C(O)N(R$^8$)(R$^9$), —(CR$^e$R$^f$)$_t$—C(O)O(R$^8$), and —(CR$^e$R$^f$)$_t$—C(O)N(R$^8$)(R$^9$), or a pharmaceutically acceptable salt, prodrug, salt of a prodrug, or a combination thereof.

10. The method of claim 7, wherein R$^c$ and R$^d$, together with the carbon atom to which they are attached, is a monocyclic heterocycle of formula (c) wherein 1, 2, 3, or 4 hydrogen atoms attached to the ring carbon of the monocyclic heterocycle ring are optionally replaced with radicals selected from the group consisting of alkyl, halogen, —CN, haloalkyl, —C(O)O(R$^8$), —C(O)N(R$^8$)(R$^9$), —(CR$^e$R$^f$)$_t$—C(O)O(R$^8$), and —(CR$^e$R$^f$)$_t$—C(O)N(R$^8$)(R$^9$), or a pharmaceutically acceptable salt, prodrug, salt of a prodrug, or a combination thereof.

11. The method of claim 10, wherein W$^6$ is O or N(R$^x$), or a pharmaceutically acceptable salt, prodrug, salt of a prodrug, or a combination thereof.

12. The method of claim 5, wherein L$^1$ is —(CR$^p$R$^q$)$_s$— and X is —C(O)OH, or a pharmaceutically acceptable salt, prodrug, salt of a prodrug, or a combination thereof.

13. The method of claim 1, wherein the compound of formula (I) is selected from the group consisting of:

N-[2-fluoro-5-(trifluoromethyl)phenyl]-N'-{4-[2-(4-hydroxytetrahydro-2H-pyran-4-yl)-1,3-thiazol-5-yl]phenyl}urea;
N-{4-[2-(1-ethyl-4-hydroxypiperidin-4-yl)-1,3-thiazol-5-yl]phenyl}-N'-[2-fluoro-5-(trifluoromethyl)phenyl]urea;
4-(5-{4-[(5,7-dimethyl-1,3-benzoxazol-2-yl)amino]-3-fluorophenyl}-1,3-thiazol-2-yl)tetrahydro-2H-pyran-4-ol;
4-(5-{4-[(7-methyl-1,3-benzoxazol-2-yl)amino]phenyl}-1,3-thiazol-2-yl)tetrahydro-2H-pyran-4-ol;
4-(5-{2-chloro-4-[(7-chloro-1,3-benzoxazol-2-yl)amino]phenyl}1,3-thiazol-2-yl)tetrahydro-2H-pyran-4-ol;
4-(5-{4-[(7-chloro-1,3-benzoxazol-2-yl)amino]-2-methylphenyl}-1,3-thiazol-2-yl)tetrahydro-2H-pyran-4-ol;
N-[2-fluoro-5-(trifluoromethyl)phenyl]-N'-(6-[2-(4-hydroxytetrahydro-2H-pyran-4-yl)-1,3-thiazol-5-yl]pyridin-3-yl}urea;
N-{4-[2-(1-ethyl-4-hydroxypiperidin-4-yl)-1,3-thiazol-5-yl]-2-fluoropheny-1}-N'-[2-fluoro-5-(trifluoromethyl)phenyl]urea;
N-(2,5-difluorophenyl)-N'-{4-[2-(1-ethyl-4-hydroxypiperidin-4-yl)-1,3-thiazol-5-yl]-2-fluorophenyl}urea;
N-[2-fluoro-5-(trifluoromethyl)phenyl]-N'-{6-[2-(1-hydroxycyclopentyl)-1,3-thiazol-5-yl]pyridin-3-yl}urea;
phenyl 4-[2-(4-hydroxytetrahydro-2H-pyran-4-yl)-1,3-thiazol-5-yl]phenylcarbamate;
N-{4-[2-(4-hydroxytetrahydro-2H-pyran-4-yl)-1,3-thiazol-5-yl]phenyl}piperidine-1-carboxamide;
tert-butyl 3-(5-{4[({[2-fluoro-5-(trifluoromethyl)phenyl]amino}carbonyl)amino]phenyl}-1,3-thiazol-2-yl)-3-hydroxypyrrolidine-1-carboxylate;
N-[2-fluoro-5-(trifluoromethyl)phenyl]-N'-{4-[2-(3-hydroxypyrrolidin-3-yl)-1,3-thiazol-5-yl]phenyl}urea;
N-[2-fluoro-5-(trifluoromethyl)phenyl]-N'-{4-[2-(3-hydroxy-1-methylpyrrolidin-3-yl)-1,3-thiazol-5-yl]phenyl}urea;
N-{4-[2-(1-ethyl-3-hydroxypyrrolidin-3-yl)-1,3-thiazol-5-yl]phenyl}-N'-[2-fluoro-5-(trifluoromethyl)phenyl]urea;
N-[2-fluoro-5-(trifluoromethyl)phenyl]-N'-{4-[2-(1-hydroxycyclopentyl)-1,3-thiazol-5-yl]phenyl}urea;
N-{4-[2-(1-hydroxycyclopentyl)-1,3-thiazol-5-yl]phenyl}-N'-[3-(trifluoromethyl)phenyl]urea;
N-[2-fluoro-5-(trifluoromethyl)phenyl]-N'-{4-[2-(1-hydroxycyclobutyl)-1,3-thiazol-5-yl]phenyl}urea;
N-{4-[2-(1-hydroxycyclobutyl)-1,3-thiazol-5-yl]phenyl}-N'-[3-(trifluoromethyl)phenyl]urea;
(±)-Cis-3-hydroxy-3-{4'-[({[3-(trifluoromethyl)phenyl]amino}carbonyl)amino]-1,1'-biphenyl-4-yl}cyclopentanecarboxylic acid;
N-[2-fluoro-5-(trifluoromethyl)phenyl]-N'-{4-[2-(1-methoxycyclopentyl)-1,3-thiazol-5-yl]phenyl}urea;
{[1-(5-{4-[({[2-fluoro-5-(trifluoromethyl)phenyl]amino}carbonyl)amino]phenyl}-1,3-thiazol-2-yl)cyclopentyl]oxy}acetic acid;
{[1-(5-{4-[(bicyclo[4.2.0]octa-1,3,5-trien-7-ylcarbonyl)amino]phenyl}-1,3-thiazol-2-yl)cyclobutyl]oxy}acetic acid;
({1-[5-(4-{[(2-fluorophenyl)acetyl]amino}phenyl)-1,3-thiazol-2-yl]cyclobutyl}oxy)acetic acid;
{[1-(5-{4-[(anilinocarbonyl)amino]phenyl}-1,3-thiazol-2-yl)cyclobutyl]oxy}acetic acid;
{[1-(5-{4-[(anilinocarbonyl)amino]phenyl}-1,3-thiazol-2-yl)cyclobutyl]oxy}acetic acid;
{[1-(5-{6-[(anilinocarbonyl)amino]pyridin-3-yl}-1,3-thiazol-2-yl)cyclopentyl]oxy}acetic acid;
{[1-(5-{6-[({[3-(trifluoromethyl)phenyl]amino}carbonyl)amino]pyridin-3-yl}-1,3-thiazol-2-yl)cyclopentyl]oxy}acetic acid;
{[1-(4-{6-[(anilinocarbonyl)amino]pyridin-3-yl}phenyl)cyclopentyl]oxy}acetic acid;
(±)-Cis-3-(4'-{[(2-fluorophenyl)acetyl]amino}-1,1'-biphenyl-4-yl)-3-hydroxycyclopentanecarboxylic acid;
[(1-{5-[4-({2-[(4-chlorophenyl)amino]-3,4-dioxocyclobut-1-en-1-yl}amino)phenyl]-1,3-thiazol-2-yl}cyclobutyl)oxy]acetic acid;
{[1-(5-{4-[(anilinocarbonyl)amino]phenyl}-4-methyl-1,3-thiazol-2-yl)cyclopentyl]oxy}acetic acid;
{[1-(4-methyl-5-{4-[({[3-(trifluoromethyl)phenyl]amino}carbonyl)amino]phenyl}-1,3-thiazol-2-yl)cyclopentyl]oxy}acetic acid;
{[1-(5-{6-[(anilinocarbonyl)amino]pyridin-3-yl}-4-methyl-1,3-thiazol-2-yl)cyclopentyl]oxy}acetic acid;
{[1-(4-methyl-5-{6-[({[3-(trifluoromethyl)phenyl]amino}carbonyl)amino]pyridin-3-yl}-1,3-thiazol-2-yl)cyclopentyl]oxy}acetic acid;
{[1-(5-{6-[{[2-fluor-5-(trifluoromethyl)phenyl]amino}carbonyl)amino]pyridin-3-yl}-1,3-thiazol-2-yl)cyclopentyl]oxy}acetic acid;
2-{[1-(5-{6-[{[3-(trifluoromethyl)phenyl]amino}carbonyl)amino]pyridin-3-yl}-1,3-thiazol-2-yl)cyclopentyl]oxy}propanoic acid;
2-{[1-(5-{6-[(anilinocarbonyl)amino]pyridin-3-yl}-1,3-thiazol-2-yl)cyclopentyl]oxy}propanoic acid;
{[1-(5-{4-[(7-methyl-1,3-benzoxazol-2-yl)amino]phenyl}-1,3-thiazol-2-yl)cyclopentyl]oxy}acetic acid;
N-{4-[2-(4-hydroxytetrahydro-2H-pyran-4-yl)-1,3-thiazol-5-yl]phenyl}-2-[3-(trifluoromethyl)phenyl]acetamide;
2-(2,4-difluorophenyl)-N-{4-[2-(4-hydroxytetrahydro-2H-pyran-4-yl)-1,3-thiazol-5-yl]phenyl}acetamide;
2-(2,5-difluorophenyl)-N-{4-[2-(4-hydroxytetrahydro-2H-pyran-4-yl)-1,3-thiazol-5-yl]phenyl}acetamide;
[(1-{5-[4-(benzoylamino)phenyl]-1,3-thiazol-2-yl}cyclobutyl)oxy]acetic acid;
({1-[5-(4-{[(3-fluorophenyl)acetyl]amino}phenyl)-1,3-thiazol-2-yl]cyclobutyl}oxy) acetic acid;
({1-[5-(4-{[4-(trifluoromethyl)benzoyl]amino}phenyl)-1,3-thiazol-2-yl]cyclobutyl}oxy) acetic acid;
[(1-{5-[4-({[2-fluoro-5-(trifluoromethyl)phenyl]acetyl}amino)phenyl]-1,3-thiazol-2-yl}cyclobutyl)oxy]acetic acid;
{[1-(5-{6-[{[3-(trifluoromethyl)phenyl]amino}carbonyl)amino]pyridin-3-yl-}-1,3-oxazol-2-yl)cyclopentyl]oxy}acetic acid;
({1-[5-(4-{[(2,5-difluorophenyl)acetyl]amino}phenyl)-1,3-thiazol-2-yl]cyclobutyl}oxy) acetic acid;
({1-[5-(4-{[(3,5-difluorophenyl)acetyl]amino}phenyl)-1,3-thiazol-2-yl]cyclobutyl}oxy) acetic acid;
({1-[5-(4-{[(3,4-difluorophenyl)acetyl]amino}phenyl)-1,3-thiazol-2-yl]cyclobutyl}oxy) acetic acid;
{[1-(4-{6-[{[3-(trifluoromethyl)phenyl]amino}carbonyl)amino]pyridin-3-yl}phenyl)cyclopentyl]oxy}acetic acid;
2-(1-(2-fluoro-4-(6-(3-(3-(trifluoromethyl)phenyl)ureido)pyridin-3-yl)phenyl)cyclopentyloxy)acetic acid;
1-(5-(4-(4-oxa-1-azabicyclo[3.2.1]octan-5-yl)phenyl)pyridin-2-yl)-3-phenylurea;
2-(1-(3-fluoro-4-(6-(3-(3-(trifluoromethyl)phenyl)ureido)pyridin-3-yl)phenyl)cyclopentyloxy) acetic acid;

2-(1-(3-fluoro-4-(6-(3-(3-(trifluoromethyl)phenyl)ureido)pyridin-3-yl)phenyl)cyclobutoxy)acetic acid;

[(1-{5-[4-({[(2-fluorophenyl)amino]carbonyl}amino)phenyl]pyridin-2-yl}cyclopentyl)oxy]acetic acid;

[1-(4-{6-[{[3-(trifluoromethyl)phenyl]amino}carbonyl)amino]pyridin-3-yl}phenyl)cyclopentyl]acetic acid;

(1-{4-[6-({[(2-fluorophenyl)amino]carbonyl}amino)pyridin-3-yl]phenyl}cyclopentyl)acetic acid;

{[1-(2-fluoro-4-{6-[({[3-(trifluoromethyl)phenyl]amino}carbonyl)amino]pyridin-3-yl}phenyl)cyclobutyl]oxy}acetic acid;

[(1-{2-fluoro-4-[6-({[3-(trifluoromethyl)phenyl]acetyl}amino)pyridin-3-yl]phenyl}cyclobutyl)oxy]acetic acid; and {[1-(3-fluoro-4'-{[6-(trifluoromethoxy)-1,3-benzothiazol-2-yl]amino}-1,1'-biphenyl-4-yl)cyclobutyl]oxy}acetic acid;

or a pharmaceutically acceptable salt, prodrug, salt of a prodrug, or a combination thereof.

14. The method of claim 1, wherein a pharmaceutical composition comprises the compound of formula (I).

15. The method of claim 1, wherein a pharmaceutical composition comprises the compound of formula (I), and one or more additional pharmaceutical agents selected from the group consisting of DPPIV inhibitor, incretin mimetic, metformin, fenofibrate, rimonabant, sibutramine, orlistat, a statin, and nicotinic acid.

* * * * *